United States Patent [19]

Itoh et al.

[11] Patent Number: 5,466,820

[45] Date of Patent: Nov. 14, 1995

[54] PRODUCTION OF DI OR TRI-AZOLYL SUBSTITUTED 5-KETO AZOLE COMPOUNDS

[75] Inventors: Katsumi Itoh, Toyono; Kenji Okonogi, Mishima; Norikazu Tamura, Kobe, all of Japan

[73] Assignee: Takeda Chemical Industries, Ltd., Osaka, Japan

[21] Appl. No.: 293,066

[22] Filed: Aug. 19, 1994

Related U.S. Application Data

[62] Division of Ser. No. 53,239, Apr. 28, 1993, Pat. No. 5,371,181.

[30] Foreign Application Priority Data

Apr. 28, 1992 [JP] Japan ................................. 4-110400
Feb. 10, 1993 [JP] Japan ................................. 5-022623

[51] Int. Cl.⁶ ................................................. C07D 403/06
[52] U.S. Cl. ................... 548/263.2; 548/251; 548/266.2
[58] Field of Search ................................. 548/263.2, 251, 548/266.2

Primary Examiner—David B. Springer
Attorney, Agent, or Firm—Foley & Lardner

[57] ABSTRACT

An azole compound represented by the formula (I):

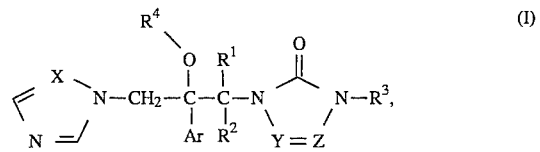

wherein Ar is a substituted phenyl group; $R^1$ and $R^2$ independently are a hydrogen atom or a lower alkyl group, or $R^1$ and $R^2$ may combine together to form a lower alkylene group; $R^3$ is a group bonded through a carbon atom; $R^4$ is a hydrogen atom or an acyl group; X is a nitrogen atom or a methine group; and Y and Z independently are a nitrogen atom or a methine group which may optionally be substituted with a lower alkyl group, or a salt thereof, which is useful for prevention and therapy of fungal infections of mammals as antifungal agent.

2 Claims, No Drawings

PRODUCTION OF DI OR TRI-AZOLYL SUBSTITUTED 5-KETO AZOLE COMPOUNDS

This application is a divisional of Ser. No. 08/053,239 filed Apr. 28, 1993, now U.S. Pat. No. 5,371,181.

DESCRIPTION OF THE PRESENT INVENTION

1. Field of the Invention

The present invention relates to azole compounds useful as antifungal therapeutic agents and their use.

2. Prior Art

Various compounds have been reported already as antifungal agents (for example, EPA-122,693, EPA-122,056 and EPA-332,387). These compounds are, however, not satisfactory in their therapeutic effects from the viewpoint of antifungal activity, antifungal spectrum, side effect and pharmacokinetics.

Conventional antifungal agents do not exhibit sufficient therapeutic effect and, in addition, there are many problems on side effects, pharmacokinetics, superinfection and acquisition of drug-resistance.

For solving such problems, it would be clear that compounds having higher safety, better absorption in vivo and more potent antifungal activity are desired as therapeutic agents.

SUMMARY OF THE INVENTION

The present invention is to provide an azole compound of formula (I):

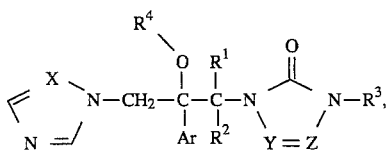

wherein Ar is a substituted phenyl group; $R^1$ and $R^2$ independently are a hydrogen atom or a lower alkyl group, or $R^1$ and $R^2$ may combine together to form a lower alkylene group; $R^3$ is a group bonded through a carbon atom; $R^4$ is a hydrogen atom or an acyl group; X is a nitrogen atom or a methine group; and Y and Z independently are a nitrogen atom or a methine group which may optionally be substituted with a lower alkyl group, or a salt thereof.

Further, the present invention is to provide an antifungal agent which comprises an azole compound represented by the formula (I) or a salt thereof.

DETAILED DESCRIPTION OF THE PREFERRED EMBODIMENT

Examples of the substituted phenyl groups represented by Ar in the formula (I) is a phenyl group having one to three substituents independently selected from a halogen (e.g., fluorine, chlorine, bromine or iodine), halogenated lower $(C_{1-3})$ alkyl group and halogenated lower $(C_{1-3})$ alkoxy group such as 2,4-difluorophenyl, 2,4-dichlorophenyl, 4-chlorophenyl, 4-fluorophenyl, 2-chlorophenyl, 2-fluorophenyl, 4-trifluoromethylphenyl, 2-fluoro-4-chlorophenyl, 2-chloro-4-fluorophenyl, 4-trifluoromethoxyphenyl, 2,4,6-trifluorophenyl, 4-bromophenyl, among which a phenyl group substituted with one to two fluorine atoms is particularly preferred.

Examples of the lower alkyl groups represented by $R^1$ or $R^2$ are straight or branched alkyl groups having 1 to 3 carbon atoms such as methyl, ethyl, propyl or isopropyl, among which methyl is particularly preferred. Preferred combinations of $R^1$ and $R^2$ are hydrogen and hydrogen; hydrogen and methyl; and methyl and methyl. Examples of the lower alkylene groups formed by connection of $R^1$ and $R^2$ are straight lower $(C_{2-4})$ alkylene groups such as ethylene, propylene or butylene, among which ethylene is preferred.

Examples of the groups bonded through a carbon atom represented by $R^3$ are optionally substituted aliphatic or aromatic hydrocarbon residues and optionally substituted aromatic heterocyclic groups.

Examples of the optionally substituted aliphatic hydrocarbon residues are alkyl, cycloalkyl, alkenyl and alkynyl, each of which may be substituted. Examples of such alkyl groups are straight or branched alkyl groups having 1 to 12 carbon atoms such as methyl, ethyl, propyl, butyl, heptyl, octyl, nonyl, decyl or dodecyl, among which lower alkyl groups having 1 to 4 carbon atoms (e.g., methyl, ethyl, propyl or butyl) are preferred. Examples of the cycloalkyl groups are cycloalkyl groups having 3 to 8 carbon atoms such as cyclopropyl, cyclobutyl, cyclopentyl, cyclohexyl, cycloheptyl or cyclooctyl, among which cycloalkyl groups having 3 to 6 carbon atoms (e.g., cyclopropyl, cyclobutyl, cyclopentyl or cyclohexyl) are preferred. Examples of the alkenyl groups are alkenyl group having 2 to 4 carbon atoms such as vinyl, propenyl and butenyl, among which alkenyl group having 2 to 3 carbon atoms (e.g., vinyl or propenyl) are preferred. Examples of the alkynyl groups are alkynyl groups having 2 to 4 carbon atoms such as ethynyl, propynyl or butynyl, among which alkynyl groups having 2 to 3 carbon atoms (e.g., ethynyl, propynyl) are preferred.

Examples of the optionally substituted aromatic hydrocarbon residues are optionally substituted aryl groups having 6 to 14 carbon atoms. Examples of the aryl groups are phenyl, naphthyl, biphenylyl, anthryl or indenyl, among which aryl groups having 6 to 10 carbon atoms (e.g., phenyl or naphthyl) are preferred.

Examples of the optionally substituted aromatic heterocyclic groups are optionally substituted fused or nonfused aromatic heterocyclic groups having at least one hetero atom selected from a nitrogen atom, sulfur atom and oxygen atom. Examples of the heterocyclic groups are imidazolyl, triazolyl, tetrazolyl, pyrazolyl, pyridyl, thiazolyl, thiadiazolyl, thienyl, furyl, pyrrolyl, pyrazinyl, pyrimidinyl, oxazolyt, isoxazolyl, benzimidazolyl, imidazopyrimidinyl, imidazopyridinyl, imidazopyrazinyl, imidazopyridazinyl, benzothiazolyl, quinolyl, isoquinolyl, quinazolinyl or indolyl, among which optionally substituted five- or six-membered aromatic heterocyclic groups having 1 to 3 hereto atoms selected from a nitrogen atom, sulfur atom and oxygen atom (e.g., imidazolyl, triazolyl, thiazolyl, thiadiazolyl, thienyl, furyl, pyridyl or pyrimidinyl) are preferred.

Examples of the substituents for the optionally substituted aliphatic or aromatic hydrocarbon residues and the optionally substituted aromatic heterocyclic groups shown by $R^3$ in the compound of formula (I) are hydroxy group, optionally esterified carboxy group (e.g., carboxy, methoxycarbonyl, ethoxycarbonyl or butoxycarbonyl), nitro group, amino group, acylamino group (e.g., alkanoyl amino group such as acetylamino, propionylamino and butyrylamino), alkylamino group (e.g., methylamino, dimethylamino, diethylamino or dibutylamino), optionally substituted cyclic amino group (e.g., pyrrolidinyl, morpholino, piperidino, piperazinyl, N-benzylpiperazinyl, N-acetylpiperazinyl, N-(p-methoxyphenyl)piperazinyl, N-[p-(2,2,3,3-tetrafluoropropoxy)phenyl]piperazinyl, pyrazolizinyl or perhydroazepinyl), alkoxy group (e.g., methoxy, ethoxy or butoxy), halogen (e.g., fluorine, chlorine or bromine), haloalkyl group (e.g., trifluoromethyl, dichloromethyl or trifluoroethyl), haloalkoxy group (e.g., trifluoromethoxy, 1,1,2,2-tetrafluoroethoxy, 2,2,2-trifluoroethoxy, 2,2,3,3-tetrafluoropropoxy, 2,2,3,3,3-pentafluoropropoxy, 2,2,3,3,4,4,5,5-octafluoropentory or 2-fluoroethoxy), oxo group, thioxo group, mercapto group, alkylthio group (e.g., methylthio, ethylthio or butylthio), alkylsulfonyl group (e.g., methanesulfonyl, ethanesulfonyl or butanesulfonyl) and alkanoyl group (e.g., acetyl, formyl, propionyl or butyryl). The substituents also includes the optionally substituted alkyl, cycloalkyl, alkenyl or alkynyl groups, the optionally substituted aryl and the optionally substituted fused or nonfused aromatic heterocyclic group as exemplified for $R^3$.

The acyl groups represented by $R^4$ in the compound of formula (I) include acyl groups derived from organic carboxylic acids such as alkanoyl group, preferably that with 1–7 carbon atoms (e.g., formyl, acetyl, propionyl, butyryl, isobutyryl, pentanoyl, hexanoyl or heptanoyl), particularly preferably that with 1–3 carbon atoms; arylcarbonyl group, preferably that with 7–15 carbon atoms (e.g., benzoyl or naphthalenecarbonyl), particularly preferably that with 7–11 carbon atoms; alkoxycarbonyl group, preferably that with 2–7 carbon atoms (e.g., methoxycarbonyl, ethoxycarbonyl, propoxycarbonyl, isopropoxycarbonyl, butoxycarbonyl, isobutoxycarbonyt, sec-butoxycarbonyl or tert-butoxycarbonyl), particularly preferably that with 2–4 carbon atoms; aryloxycarbonyl group, preferably that with 7–15 carbon atoms (e.g., phenoxycarbonyl), particularly preferably that with 7–11 carbon atoms; aralkylcarbonyl group, preferably that with 8–20 carbon atoms (e.g., benzylcarbonyl, phenethylcarbonyl, phenylpropylcarbonyl or naphthylethylcarbonyl), particularly preferably that with 8 to 14 carbon atoms; etc. Those may be substituted with suitable one to three substituent(s). Examples of suitable substituents are optionally-halogenated lower alkyl group, aryl group and halogen as referred to in the above-mentioned nitrogen-containing heterocyclic group.

Preferably, the above acyl groups are those which can be hydrolyzed in vivo. Specific examples thereof are formyl, acetyl, benzoyl and benzylcarbonyl.

The compound of formula (I) or salt thereof of the present invention has one or more asymmetric carbon(s) in its molecule and, therefore, there are two or more stereoisomers. Any of such stereoisomers as well as a mixture thereof is within a scope of the present invention. With respect to the optical isomers, it is preferred that when $R^1$ is hydrogen and $R^2$ is methyl, both of the carbon to which the substituted phenyl represented by Ar is bonded and another carbon to which $R^2$ is bonded are in R-configurations.

The compound of formula (I) or salt thereof of the present invention wherein $R^4$ is hydrogen can be manufactured by, for example, reacting a compound of formula (II):

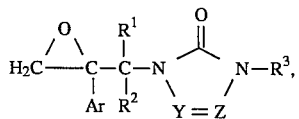
(II)

wherein the symbols have the same meanings as defined above, with a compound of formula (III):

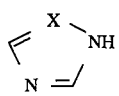
(III)

wherein the symbols have the same meanings as defined above, or salt thereof.

The above reaction can be usually conducted in a solvent which does not impede the reaction. Examples of such solvents are water; ketones such as acetone; sulfoxides such as dimethyl sulfoxide; ethers such as diethyl ether, tetrahydrofuran or dioxane; nitriles such as acetonitrile; aromatic hydrocarbons such as benzene, toluene or xylene; halogenated hydrocarbons such as dichloromethane, chloroform or 1,2-dichloroethane; esters such as ethyl acetate; amides such as dimethylformamide, acetamide or dimethylacetamide; ureylenes such as 1,3-dimethyl-2-imidazolidinone; and the like. They may be used either singly or as a mixture thereof in a suitable mixing ratio.

Further, it is preferred that the above reaction is conducted in the presence of a base such as an alkali metal hydroxide (e.g., lithium hydroxide, potassium hydroxide or sodium hydroxide), alkali metal hydride (e.g., potassium hydride or sodium hydride), alkali metal carbonate (e.g., lithium carbonate, sodium bicarbonate, cesium carbonate, potassium carbonate or sodium carbonate), organic acid salt (e.g., sodium acetate), alkali metal alcoholate (e.g., sodium methylate or potassium tert-butylate), tetrabutylammonium fluoride, bis(tri-n-butylstannyl) oxide, and the like.

In place of the compound of formula (III), its salt with metal (e.g., alkali metal such as sodium and potassium) may be used and the reaction is conducted in the above-given solvent whereby the desired compound can be prepared. The amount of the base used is usually about 0.001 to 100 equivalents, preferably about 0.01–50 equivalents, to the compound of formula (II).

The amount of the compound of formula (III) or salt thereof is about 1 to 100 equivalents, preferably about 1 to 50 equivalents, to the compound of formula (II).

The reaction temperature is not particularly limited but ranges usually about 0° to 150° C., preferably about 10 to 120° C.

The reaction time is usually about several minutes to several ten hours (e.g., five minutes to fifty hours).

The compound of formula (I) of the present invention wherein $R^4$ is a hydrogen atom or salt thereof can be manufactured by, for example, reacting a compound of formula (IV):

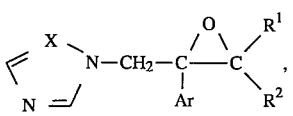
(IV)

wherein the symbols have the same meanings as defined above, or salt thereof with the compound of formula (V):

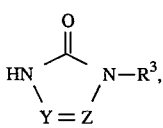
(V)

wherein the symbols have the same meanings as defined above, or salt thereof.

The above reaction can be usually conducted in a solvent which does not impede the reaction. Examples of such solvents are water; ketones such as acetone; sulfoxides such as dimethyl sulfoxide; ethers such as diethyl ether, tetrahydrofuran or dioxane; nitriles such as acetonitrile; aromatic hydrocarbons such as benzene, toluene or xylene; halogenated hydrocarbons such as dichloromethane, chloroform or 1,2-dichloroethane; esters such as ethyl acetate; amides such as dimethylformamide, acetamide or dimethylacetamide; ureylenes such as 1,3-dimethyl-2-imidazolidinone; and the like. They may be used either singly or as a mixture thereof in a suitable mixing ratio.

Further, it is preferred that the above reaction is conducted in the presence of a base such as alkali metal hydroxides (e.g., lithium hydroxide, potassium hydroxide or sodium hydroxide), alkali metal hydrides (e.g., potassium hydride or sodium hydride), alkali metal carbonates (e.g., lithium carbonate, sodium bicarbonate, cesium carbonate, potassium carbonate or sodium carbonate), organic acid salt (e.g., sodium acetate), alkali metal alcoholates (e.g., sodium methylate or potassium tert-butylate), tetrabutylammonium fluoride, and the like.

The amount of the base is usually about 0.01–100 equivalents, preferably about 0.01–50 equivalents, to the compound of formula (IV).

The amount of the compound of formula (V) or salt thereof to the compound of formula (IV) or salt thereof is about 1–100 equivalents, preferably, about 1–50 equivalents.

The reaction temperature is not particularly limited but ranges usually about 0°–150° C., preferably about 10°–120° C.

The reaction time is usually about several minutes to several ten hours (e.g., five minutes to 50 hours).

The compound of formula (I) wherein $R^4$ is a hydrogen atom or salt thereof can be manufactured by, for example, reacting a compound of formula (IV):

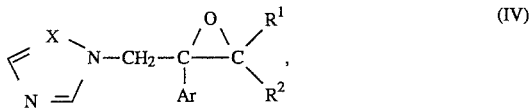

wherein the symbols have the same meanings as defined above, or salt thereof with a compound of formula (VI):

wherein the symbols have the same meanings as defined above, to give a compound of formula (VII):

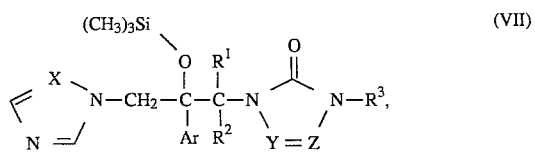

wherein the symbols have the same meanings as defined above, followed by hydrolyzing the compound of formula (VII).

The reaction of the compound of formula (IV) with (VI) is usually conducted in the absence or presence of a solvent which does not impede the reaction. Examples of such solvents are halogenated hydrocarbons (e.g., dichloromethane, chloroform or carbon tetrachloride), aromatic hydrocarbons (e.g., benzene, toluene or xylene), ethers (e.g., diethyl ether, tetrahydrofuran or dioxane) and the like. The reaction temperature is not particularly limited but ranges usually about 20°–200° C., preferably about 150°–190° C. The reaction time is about 30 minutes to 4 hours.

Hydrolysis of the compound of formula (VII) can be usually conducted in the presence of water or an organic solvent (e.g., alcohols such as methanol and ethanol; ethers such as diethyl ether, tetrahydrofuran and dioxane) which may be used either singly or as a mixture thereof at a temperature in the range of about 0° to about +40° C. For acceleration of the reaction rate, a base (e.g., sodium hydroxide, potassium carbonate, tetrabutylammonium fluoride, potassium fluoride and cesium fluoride) or an acid (e.g., hydrochloric acid, acetic acid, boron trifluoride, titanium tetrachloride, tin tetrachloride and Dowex 50W) can be added to the reaction system. The reaction temperature is usually about 0°–20° C. while the reaction time is usually about 30 minutes to 2 hours.

Alternatively, the compound of formula (I) of the present invention or salt thereof can be manufactured by, for example, reacting a compound of formula (VIII):

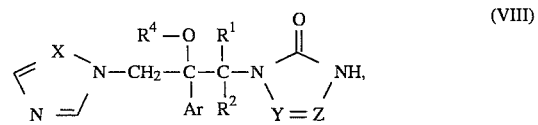

wherein the symbols have the same meanings as defined above, or salt thereof with a compound of formula (IX)

wherein $R^3$ has the same meanings as above and W is a halogen atom (e.g., chlorine, bromine or iodine) or a group represented by the formula $R^5SO_3$— wherein $R^5$ is a lower ($C_{1-4}$) alkyl group, trifluoromethyl, phenyl or tolyl.

The reaction is usually conducted in the presence of water or an organic solvent (e.g., alcohols such as methanol, ethanol, isopropyl alcohol; ethers such as tetrahydrofuran and dioxane; amides such as dimethylformamide; sulfoxides such as dimethyl sulfoxide; aromatic hydrocarbons such as benzene and toluene) which may be used either singly or as a mixuture thereof keeping at the temperature range from about −20° C. to +100° C. For acceleration of the reaction rate, a base such as alkali metal alcoholate (e.g., sodium methylate or sodium ethylate), alkali metal hydroxides (e.g., sodium hydroxide or potassium hydroxide), alkali metal carbonates (e.g., sodium carbonate or potassium carbonate), etc. can be added to the reaction system.

The compound of formula (I) (wherein $R^4$ is an acyl group) or salt thereof can also be prepared by acylating a compound of formula (I) (whierein $R^4$ is hydrogen atom) or salt thereof. This acylation can be carried out, for example, by reacting the compound of formula (X):

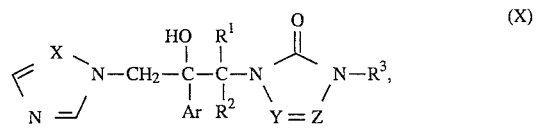

wherein the symbols have the same meanings as defined above, or salt thereof with a compound of formula (XI):

wherein $R^6$ is the same as an acyl group shown as $R^4$ above and W' is a halogen atom (e.g., chlorine or bromine) or OR⁷ [wherein R⁷ is acyl group derived from organic carboxylic acid (preferably alkanoyl group such as acetyl or propionyl)], or salt thereof.

The reaction is usually conducted in the absence or presence of a solvent which does not impede the reaction. Examples of such solvents are ketones such as acetone; sulfoxides such as dimethyl sulfoxide; ethers such as diethyl ether, tetrahydrofuran or dioxane; nitriles such as acetonitrile; aromatic hydrocarbons such as benzene, toluene or xylene; halogenated hydrocarbons such as dichloromethane, chloroform or 1,2-dichloroethane; esters such as ethyl acetate; amides such as dimethylformamide, acetamide or dimethylacetamide; ureylenes such as 1,3-dimethyl-2-imidazolidinone and the like. For acceleration of the reaction rate, a base (e.g., dimethylaminopyridin, pyridin, picolin, triethylamine) can be added to the reaction system.

The compound of formula (I) can also be used as a salt and examples of such salts are pharmacologically-acceptable salts such as inorganic salts (e.g., hydrochloride, hydrobromide, sulfate, nitrate or phosphate) and organic salts (e.g., acetate, tartrate, citrate, fumarate, maleate, toluenesulfonate or methanesulfonate).

Examples of the salts of the starting compounds including the above-mentioned compounds of formula (III), (IV), (VII), (VIII) and (X) are the same as those for the compound of formula (I).

The compound of formula (I) or salt thereof can be isolated from the reaction mixture by known isolation and purification procedure such as extraction, concentration, neutralization, filtration, recrystallization, column chromatography and thin layer chromatography.

The compound of formula (I) or salt thereof can have at least two stereoisomers. Each of such isomers and each of mixtures thereof is included in the concept of the present invention but, if desired, such an isomer can be manufactured separately. For example, a single isomer of the compound of formula (I) can be obtained by the above reaction starting from each single isomer of the starting compound of formula (II), (IV), (VII), (VIII) and (X). When the product is a mixture of two or more isomers, they may be separated into each isomer by conventional separating methods such as a method of producing salt with an optically-active acid (e.g., camphorsulfonic acid or tartaric acid) or by means of various types of chromatographies, fractional recrystallization and so on.

The salt of the compound of formula (I) can also be manufactured by a method such as by adding the above-mentioned inorganic or organic acid to the compound of the formula (I).

The compound of formula (XV) or salt thereof which is an intermediate compound of formula (II) in the present invention wherein R¹ is hydrogen, R² is methyl, the carbon to which Ar is bonded is in S-configuration and the carbon to which R² is bonded is in R-configuration can be manufactured by a method as given in the following scheme.

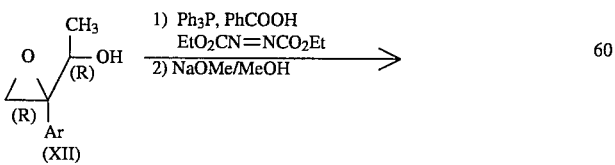

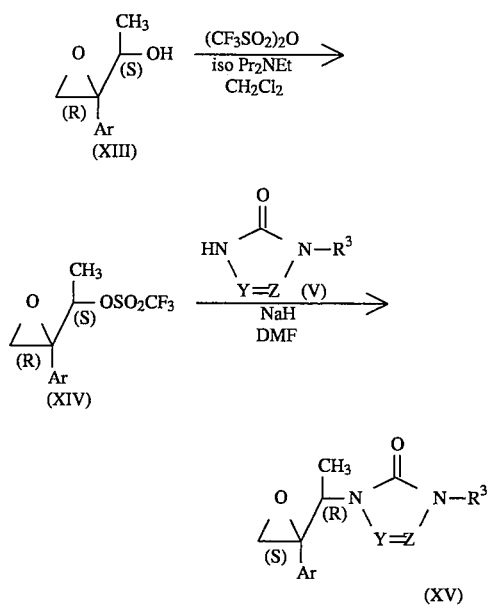

wherein Me is methyl group, Et is ethyl group, Pr is propyl group, Ph is phenyl group while the other symbols have the same meanings as defined above.

The starting compound of formula (XII) in the present invention can be manufactured by a method as given in the following scheme.

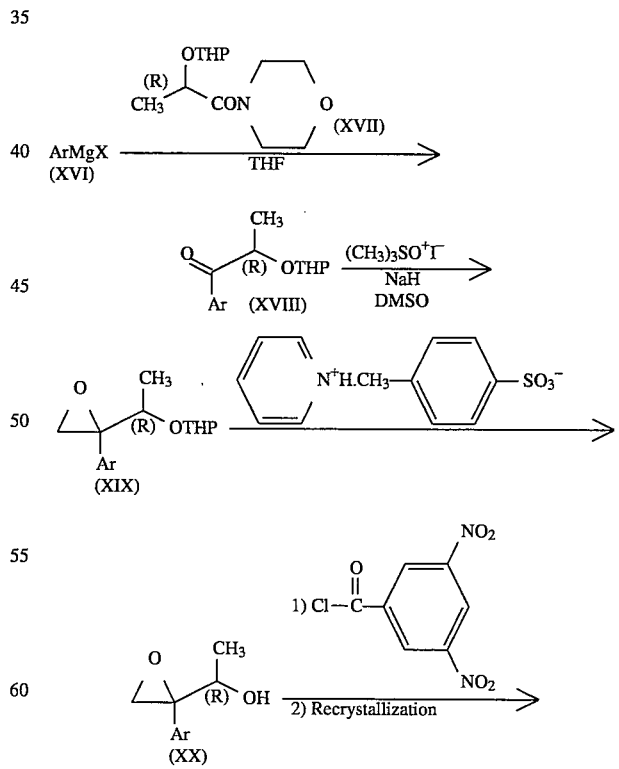

-continued

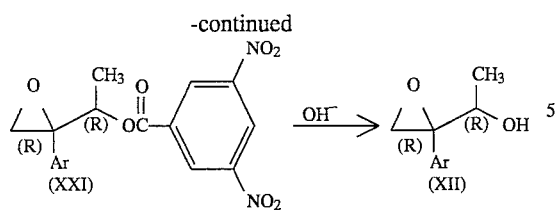

wherein THP is tetrahydropyranyl while the other symbols have the same meanings as defined above.

The compound of formula (XXIII) which is an intermediate compound of formula (IV) in the present invention wherein $R^1$ is hydrogen, $R^2$ is methyl, the carbon to which Ar is bonded is in R-configuration and the carbon to which $R^2$ is bonded is in S-configuration can be synthesized by a method as given in the following scheme.

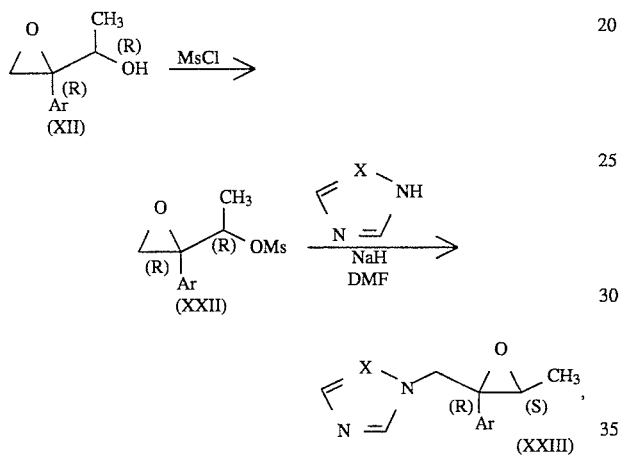

wherein Ms is methanesulfonyl group and the other symbols have the same meanings as defined above.

The compound of formula (XXIII) can also be manufactured by a method as given in the following scheme.

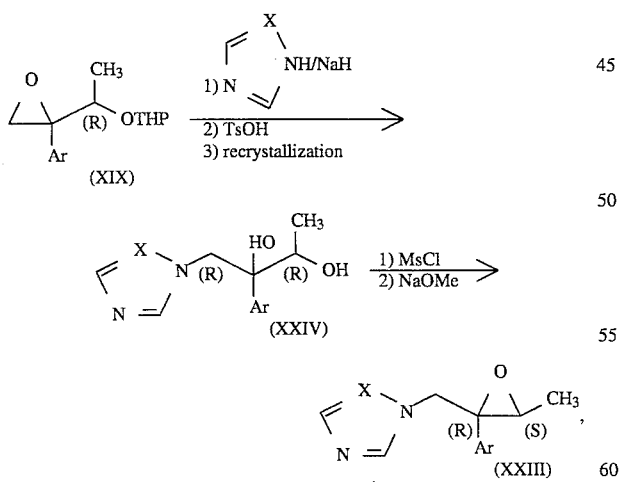

wherein the symbols have the same meanings as defined above.

The compound of formula (XXVI) which is an intermediate compound of formula (VIII) in the present invention wherein $R^1$ and $R^4$ are hydrogen, $R^2$ is methyl, the carbon to which Ar is bonded is in R-configuration and the carbon to which $R^2$ is bonded is in R-configuration can be synthesized by a method as given in the following scheme.

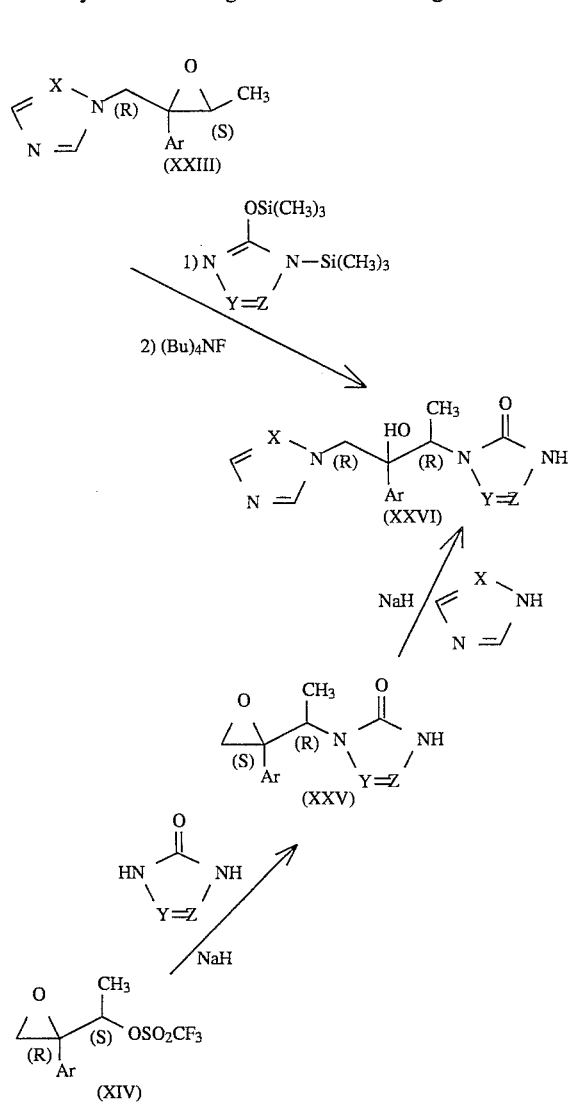

wherein Bu is butyl and the other symbols have the same meanings as defined above.

The compound of formula (XXVI) thus obtained can be made into a compound of formula (VIII) wherein $R^4$ is an acyl group by using the same reaction as the acylation reaction of the compound of formula (X).

The compound of formula (XXVIII) which is an intermediate compound of formula (V) in the present invention wherein both Y and Z are methine group can be manufactured by a method as given in the following scheme.

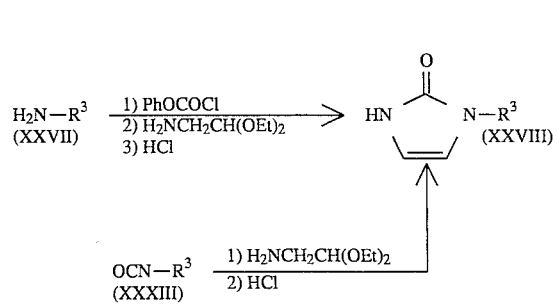

wherein the symbols have the same meanings as defined above.

The compound of formula (XXX) which is a compound of formula (V) wherein Y is nitrogen and Z is methine can be manufactured by a method given in the following scheme.

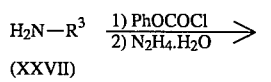

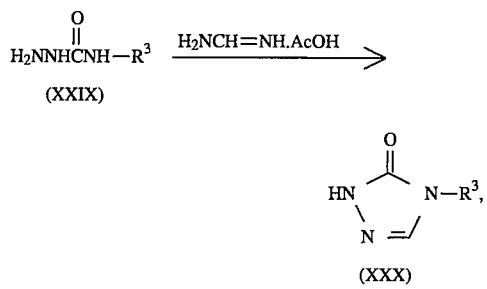

wherein Ac is acetyl group and the other symbols have the same meanings as defined above.

The compound of formula (XXXII) which is a compound of formula (V) wherein Y is methine and Z is nitrogen can be manufactured by a method as given in the following scheme.

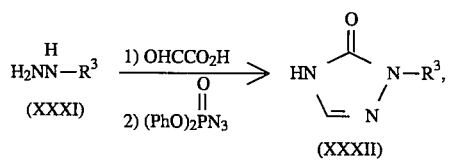

wherein the symbols have the same meanings as defined above.

The compound of formula (XXXIV) which is a compound of formula (V) wherein both Y and Z are nitrogen can be manufactured by a method given in the following scheme.

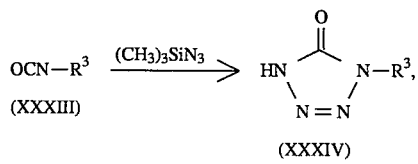

wherein the symbols have the same meanings as defined above.

The compound of formula (VI) in the present invention can be manufactured by the methods which are known per se.

The starting compounds described above can be isolated from the reaction mixture by known isolation and purification procedure such as extraction, concentration, neutralization, filtration, recrystallization, column chromatography and thin layer chromatography.

The compound of formula (I) or salt thereof having low toxicity and potent antifungal activities with broad antifungal spectrum (e.g., effective to Candida, Aspergillus or Cryptococcus) can be used for prevention and therapy of fungal infections (e.g., candidosis, aspergillosis or cryptococcosis) of mammals (e.g., human beings, domestic animals or fowls). The compound of formula (I) or salt thereof can also be used as antifungal preparations for agricultural use.

The compound of formula (I) or salt thereof can be safely administered, either orally or parenterally, to human beings in the form of pharmaceutical compositions such as oral administration preparations (e.g., powder, granules, tablets or capsules), parental preparations [e.g., injections, external preparations (e.g., nasal or dermatological ones), suppositories (e.g., rectal or vaginal ones) and so on] in per se or by mixing with suitable pharmacologically acceptable carriers, fillers or diluents.

Those preparations can be manufactured by the methods which are known per se and commonly used in the manufacture of pharmaceutical preparations.

For example, the compound of formula (I) or salt thereof of the present invention can be made into injections such as aqueous injection together with dispersing agent (e.g., Tween 80 [Atlas Powder, U.S. A.], HCO 60 [Nikko Chemicals, Japan], carboxymethylcellulose and sodium alginate), preservative (e.g., methylparaben, propylparaben, benzyl alcohol or chlorobutanol), isotonic agent (e.g., sodium chloride, glycerin, sorbitol or glucose) and the like, or as oily injection by dissolving, suspending or emulsifying in plant oil (e.g., olive oil, sesame oil, peanut oil, cotton seed oil or corn oil), propylene glycol and the like.

In the manufacture of preparations for oral administraion, the compound of formula (I) or salt thereof of the present invention is molded with pressure together, for example, with fillers (e.g., lactose, sugar or starch), disintegrating agents (e.g., starch or calcium carbonate), binders (e.g., starch, arabic gum, carboxymethylcellulose, polyvinylpyrrolidone or hydroxypropylcellulose), lubricants (e.g., talc, magnesium stearate or polyethyleneglycol 6000) and the like followed, if necessary, by coating in accordance with a known method per se with an object of taste-masking or of providing the preparation with enteric or sustained release property. Examples of the coating agents are, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (Rob/n, West Germany; a copolymer of methacrylic acid with acrylic acid) and pigments such as titanium oxide and red iron oxide.

In the case of preparation for external use, the compound of formula (I) or salt thereof of the present invention can be, for example, made into solid, semisolid or liquid preparation by a known method per se. For example, in the case of solid preparation, the compound of formula (I) or salt thereof is used as it is or mixed with fillers (e.g., glucose, mannitol, starch or microcrystalline cellulose), thickeners (e.g., natural gums, cellulose derivatives or acrylic acid polymers), etc. to give powdered composition. In the case of liquid preparation, the procedures are nearly the same as those in the case of injections to give oily or aqueous suspension. In the case of semisolid preparation, aqueous or oily gel or ointment is preferred. All of those can be added with pH adjusting agents (e.g., carbonic acid, phosphoric acid, citric acid, hydrochloric acid or sodium hydroxide), antiseptics (e.g., p-hydroxybenzoates, chlorobutanol or benzalkonium chloride) and the like. For example, it can be used for sterilization or disinfection of skin or mucous membrane as an ointment preparation containing about 0.1 to 100 mg of it per gram using vaselin or lanoline as a base material.

In the case of suppositories, the compound of the present invention (I) or salt thereof can be made, by a known method per se, into oily or aqueous suppositories in solid, semisolid or liquid. Examples of the oily base materials used therefor are higher fatty acid glycerides (e.g., cacao butter, Witepsols [Dynamite-Nobel], medium fatty acids (e.g., Migriol [Dynamite-Nobel]), plant oil (e.g., sesame oil, soybean oil or cotton seed oil) and the like. Examples of the aqueous base materials are polyethylene glycol and propylene glycol while examples of aqueous gel base materials are natural gums, cellulose derivatives, vinyl polymers and acrylic acid polymers.

Dose may vary depending upon the state of infection and the administering route and, in giving to adult patient (body weight: 50 kg) for therapy of candidosis by oral route, it is about 0.01 to 100 mg/kg/day, preferably about 0.1 to 50 mg/kg/day and, more preferably, about 0.1 to 20 mg/kg/day.

When it is used as an antifugal agent for agricultural purposes, the compound of formula (I) or salt thereof is dissolved or dispersed in a suitable liquid carrier (e.g., solvent) or mixed or adsorbed with a suitable solid carrier (e.g., diluent or filler) followed, if necessary, by adding emulsifier, suspending agent, spreader, penetrating agent, moisturizing agent, thickening agent, stabilizer, etc. to afford the preparation such as emulsion, hydrated agent, powder, granules. Such preparations can be prepared by known method per se. The amount of the compound of the formula (I) or salt thereof used is, for example in the case of rice blast disease, about 25 to 150 g, preferably about 40 to 80 g, per are of irrigated rice field.

Examples of the liquid carrier used are water, alcohols (e.g., methyl alcohol, ethyl alcohol, n-propyl alcohol, isopropyl alcohol or ethylene glycol), ethers (e.g., dioxane or tetrahydrofuran), aliphatic hydrocarbons (e.g., kerosene, lamp oil or fuel oil), aromatic hydrocarbons (e.g., benzene or toluene), halogenated hydrocarbons (e.g., methylene chloride or chloroform), acid amides (e.g., dimethylformamide or dimethylacetamide), esters (e.g., ethyl acetate or butyl acetate), nitriles (e.g., acetonitrile or propionitrile) and the like. They may be used either singly or as a mixture thereof in a suitable mixing ratio.

Examples of the solid carrier are plant powder (e.g., soybean powder, tobacco powder or wheat flour), mineral powder (e.g., kaolin or bentonite), alumina, sulfur powder, activated charcoal, etc. They may be used either singly or as a mixture thereof by mixing in a suitable ratio.

EXAMPLES

The present invention will be further illustrated by way of the following reference examples and working examples.

$^1$H-NMR spectra were measured by a spectrometer of Varian Gemini 200 type (200 MHz) using tetramethylsilane as an internal standard. All $\delta$ values are given by ppm. In the mixing solvents, the figures given in () are mixing ratio of each of the solvents by volume. The symbol "%" means that by weight unless otherwise specified.

Symbols in the examples have the following meanings. Thus, s: singlet; d: doublet; t: triplet; q: quartet; dd: double doublet; m: multipier; br: broad; J: coupling constant.

REFERENCE EXAMPLE 1

2-[(1R)-1-(3,4,5,6-Tetrahydro-2H-pyran-2-yl)oxyethyl]-2-(2,4-difluorophenyl)oxirane (82 g; manufactured by a method disclosed in Japanese Laid Open Application Hei 04/074168-A) and 6.3 g of pyridinium p-toluenesulfonate were dissolved in 600 ml of ethanol and the solution was stirred at 55° C. for 1 hour. The reaction solution was concentrated under reduced pressure. The residue was dissolved in 1 liter of ethyl acetate and the resulting solution was washed with water (2×200 ml). The aqueous layer was extracted with ethyl acetate (2×100 ml). The organic layers were combined, washed with saturated aqueous solution of sodium chloride, dried over magnesium sulfate and distilled off under reduced pressure. The residue was purified by silica gel chromatography (eluate ; hexane:ethyl acetate= 10:1 to 8:1 to 3:1) to give 31.5 g of (1R)-1-[2-(2,4-difluorophenyl)-2-oxiranyl]ethanol as a pale yellow oil.

$^1$H-NMR (CDCl$_3$) $\delta$:1.14–1.23 (3H,m), 1.77, 2.22 (1H), 2.80, 2.92 (1H), 3.27–3.32 (1H), 4.00–4.20 (1H,m), 6.75–6.94 (2H,m), 7.36–7.48 (1H,m).

REFERENCE EXAMPLE 2

(1R)-1-[2-(2,4-Difluorophenyl)-2-oxiranyl]ethanol (31.5 g) and 40 g of 3,5-dinitrobenzoyl chloride were dissolved in 500 ml of methylene chloride and, with ice cooling, 24.1 ml of triethylamine was added dropwise thereinto. The reaction solution was stirred at room temperature for 3.5 hours, washed with 150 ml of water and then with 150 ml of 5% aqueous solution of sodium bicarbonate, dried over magnesium sulfate and concentrated under reduced pressure. The crystals separated out were collected by filtration and washed with methylene chloride. The mother liquor and the washing were combined and distilled off under reduced pressure, then 25 ml of ethyl acetate and 300 ml of methanol were added to the residue and the mixture was cooled with ice. The crystals separated out were collected by filtration and recrystallized from a mixture of 25 ml of ethyl acetate and 250 ml of methanol to give 28.7 g of [(1R)-1-[(2R)-2-(2,4-difluorophenyl)-2-oxiranyl]ethyl]3,5-dinitrobenzoate as colorless needles.

m.p. 104°–107° C. (recrystallized from ethyl acetatehexane).

$^1$H-NMR (CDCl$_3$) $\delta$: 1.46 (3H,dd,J=6.6 Hz, J=1.2 Hz), 3.01 (1H,d,J=4.6 Hz), 3.23 (1H,d,J=4.6 Hz), 5.33 (1H,q,J= 6.6 Hz), 6.85–7.07 (2H,m), 7.54 (1H,m), 9.13 (2H,d,J=2.2 Hz), 9.25 (1H,t,J=2.2 Hz).

REFERENCE EXAMPLE 3

[(1R)-1-[(2R)-2-(2,4-Difluorophenyl)-2-oxiranyl]ethyl]3, 5-dinitorbenzoate (50 g) was dissolved in 2 liters of methanol and, at room temperature, 255 ml of 1N sodium hydroxide was added dropwise. The reaction solution was stirred at room temperature for 1 hour and neutralized with 127 ml of 1N hydrochloric acid. Methanol was removed under reduced pressure, then 1 liter of ethyl acetate and 200 ml of water were added to the residue, and the mixture was extracted with ethyl acetate. The organic extract was washed with 200 ml of saturated aqueous solution of sodium chloride, dried over magnesium sulfate and distilled off under reduced pressure. The residue was purified by silica gel chromatography (eluate; ethyl acetate:hexane=1:3) to give 25 g of (1R)-1-[(2R)-2-(2,4-difluorophenyl)-2-oxiranyl]ethanol as a pale yellow oil.

$^1$H-NMR (CDCl$_3$) $\delta$: 1.17 (3H,dd,J=6.6 Hz, 1.2 Hz), 2.05 (1H,br), 2.80 (1H,d,J=5.2 Hz), 3.30 (1H,d,J=5.2 Hz), 4.01–4.17 (1H,m), 6.75–6.93 (2H,m), 7.36–7.48 (1H,m).

REFERENCE EXAMPLE 4

To a solution of 16.1 g of (1R)-1-[(2R)-2-(2,4-difluorophenyl)- 2-oxiranyl]ethanol in 320 ml of tetrahydrofuran were added, with ice cooling, 63.3 g of triphenylphosphine, 29.5 g of benzoic acid and 42.0 g of diethyl azodicarboxylate and the mixture was stirred in an argon atmosphere at room temperature for 6 hours. To the reaction solution were added 800 ml of ethyl acetate and 500 ml of water to fractionate and the aqueous layer was extracted with 200 ml of ethyl acetate. The organic layers were combined, washed with water and saturated aqueous solution of sodium chloride, dried over magnesium sulfate and concentrated. The residue was purified by silica gel chromatography (eluate; hexane:ethyl acetate=15:1 to 7:1) to give 19.2 g of [(1S)-1-[(2R)-2-(2,4-difluorophenyl)-2-oxiranyl]ethyl]benzoate as a colorless oil.

$^1$H-NMR (CDCl$_3$) δ:1.37 (3H,d,J=6.6 Hz), 2.90 (1H,d,J= 5.2 Hz), 3.28 (1H,d,J=5.2 Hz), 5.36 (1H,q,J=6.6 Hz), 6.74–6.94 (2H,m), 7.38–7.60 (4H,m), 7.94–8.01 (2H,m).

IR$\gamma_{max}^{neat}$ cm$^{-1}$; 1725, 1615, 1600, 1505, 1450, 1425.

[(1S)-1-[(2R)-2-(2,4-Difluorophenyl)-2-oxiranyl]ethyl]benzoate (15.9 g) was dissolved in 800 ml of methanol. 28% Methanolic solution (12.9 ml) of sodium methylate was added with ice cooling and the reaction solution was stirred at room temperature for 6 hours. To the reaction solution was added 63.2 ml of 1N hydrochloric acid and the solvent was distilled off under reduced pressure. The residue was purified by silica gel chromatography (eluate; hexane:ethyl acetate=6:1 to 2:1) to give 9.7 g of (1S)-1-[(2R)-2-(2,4-difluorophenyl)- 2-oxiranyl]ethanol as a colorless oil.

$^1$H-NMR (CDCl$_3$) δ: 1.20 (3H,dd,J=6.4 Hz, 2.2 Hz), 2.24 (1H,d,J=1 Hz), 2.92 (1H,d,J=5 Hz), 3.28 (1H,d,J=5 Hz), 4.12 (1H,q,J=6.4 Hz), 6.77–6.95 (2H,m), 7.34 (1H,m).

IRδ$_{max}^{neat}$ cm$^{-1}$: 3420, 2980, 1615, 1600, 1500, 1425.

REFERENCE EXAMPLE 5

To a solution of 535 mg of (1S)-1-[(2R)-2-(2,4-difluorophenyl)-2-oxiranyl]ethanol in 15 ml of dichloromethane was added, in a nitrogen atmosphere, 0.51 ml of diisopropylethylantine at −78° C. and then 0.49 ml of trifluoromethanesulfonic acid anhydride was added dropwise during 3 minutes. The mixture was stirred at −78° C. for 20 minutes, then at −20° C. for 20 minutes and concentrated to about 9 ml at −10° C. The concentrate was subjected to a flash column chromatography using silica gel (3.2×4cm) and eluted with dichloromethane-hexane (1:1). The desired fraction was concentrated to about 3 ml, the residue was added to a solution of sodium salt of 1-(4-trifluoromethylphenyl)-2(1H,3H)-imidazolone [obtained from 606 mg of 1-(4-trifluoromethylphenyl)-2(1H,3H)-imidazolone, 3 ml of dimethylformamide and 85 mg of 60% sodium hydride in oil] at −10° C. and stirred for 10 minutes. The reaction solution was further stirred for 20 minutes at 0° C. Water (30 ml) was added to the reaction solution and the mixture was extracted with 30 ml each of ethyl acetate for four times. The ethyl acetate layer was washed with 20 ml of water twice and then with saturated aqueous solution of sodium chloride once, dried over anhydrous magnesium sulfate and distilled off under reduced pressure to give a colorless oil. This was purified by silica gel chromatography (eluate; hexane:ethyl acetate =3:1 to 2:1 to 1:1) to give 362 mg of 1-[(1R,2S)-2-(2,4-difluorophenyl)-2,3-epoxy-1-methylpropyl]-3-(4-trifluoromethylphenyl)-2(1H,3H)-imidazolone and 209 mg of (2R)-2-(2,4-difluorophenyl)-2-[(1R)-1-[1-(4-trifluoromethylphenyl)-2-imidazolyloxy]ethyl]oxirane.

1-[(1R,2S)-2-(2,4-Difluorophenyl)-2,3-epoxy-1-methylpropyl]-3-(4-trifluoromethylphenyl)-2(1H,3H)-imidazolone, colorless prisms.

m.p. 135°–136° C.

$^1$H-NMR (CDCl$_3$) δ:1.37 (3H,d,J=7.2 Hz), 2.72 (1H,d,J= 4.4 Hz), 2.82 (1H,d,J=4.4 Hz), 5.09 (1H,q,J=7.2 Hz), 6.50 (1H, d, J=3.2 Hz), 6.64 (1H,d,J=3.2 Hz), 6.80–6.97 (2H,m), 7.35–7.50 (1H,m), 7.69 (2H,d,J=8.4 Hz), 7.82 (2H,d,J=8.4 Hz).

IRδ$_{max}^{KBr}$ cm$^{-1}$: 3010, 1684, 1616, 1523.

Elemental analysis for C$_{20}$H$_{15}$F$_5$N$_2$O$_2$ Calcd: C 58.54, H 3.68, N 6.83 Found: C 58.80, H 3.90, N 6.81

(2R)-2-(2,4-Difluorophenyl)-2-[(1R)-1-[1-(4-trifluoromethylphenyl)-2-imidazolyloxy]ethyl]oxirane, colorless oil.

$^1$H-NMR (CDCl$_3$) δ: 1.46 (3H,dd,J=6.6, 1.6 Hz), 2.89 (1H, d,J=4.8 Hz), 3.16 (1H,d,J=4.8 Hz), 5.24 (1H,q,J=6.6 Hz), 6.70–6.91 (4H,m), 7.22–7.40 (1H,m), 7.50 (2H,d,J=8.4 Hz), 7.70 (2H,d,J=8.4 Hz).

IR$\gamma_{max}^{neat}$ cm$^{-1}$: 3010, 1620, 1616, 1599, 1547. SIMS (m/z): 411 (M+H)$^+$

REFERENCE EXAMPLE 6

In the same manner as in Reference Example 5, starting from 423 mg of (1S)-1-[(2R)-2-(2,4-difluorophenyl)-2oxiranyl]ethanol and 207 mg of 1-methyl-2(1H,3H)-imidazolone prepared by a method described in Journal of American Chemical Society vol. 98, page 8218 (1976), 102 mg of 1-[(1R,2S)-2-(2,4-difluorophenyl)-2,3-epoxy-1-methylpropyl]-3-methyl-2(1H,3H)-imidazolone was obtained as a colorless oil.

$^1$H-NMR (CDCl$_3$) δ: 1.40 (3H, dd, J=6.4, 1.4 Hz), 2.90 (1H, d,J=5.4 Hz), 3.23 (1H,d,J=5.4 Hz), 3.37 (3H,s), 5.18 (1H,q,J=6.4 Hz), 6.48 (1H,d,J=1.6 Hz), 6.59 (1H,d,J=1.6 Hz), 6.75–6.98 (2H,m), 7.41–7.59 (1H,m).

IR$\gamma_{max}^{neat}$ cm$^{-1}$: 2980, 1734, 1616, 1600, 1539, 1506. SIMS (m/z): 281 (M+H)$^+$

REFERENCE EXAMPLE 7

In the same manner as in Reference Example 5, starting from 1.95 g of (1S)-1-[(2R)-2-(2,4-difluorophenyl)-2-oxiranyl]ethanol and 1.39 g of 1-(4-fluorophenyl)-2(1H,3H)-imidazolone, 1.10 g of 1-[(1R,2S)-2-(2,4-difluorophenyl)-2,3-epoxy-1-methylpropyl]-3-(4-fluorophenyl)-2(1H,3H)-imidazolone and 0.88 g of (2R)-2-(2,4-difluorophenyl)-2-[(1R)-1-[1-(4-fluorophenyl)-2-imidazolyloxy]ethyl]oxirane were obtained.

1-[(1R,2S)-2-(2,4-Difluorophenyl)-2,3-epoxy-1-methylpropyl]-3-(4-fluorophenyl)-2(1H,3H)-imidazolone, colorless oil.

$^1$H-NMR (CDCl$_3$) δ: 1.37 (3H,d,J=7.2 Hz), 2.70 (1H,d, J=4.8 Hz), 2.81 (1H,d,J=4.8 Hz), 5.07 (1H,q,J=7.2 Hz), 6.44 (1H, d,J=3.2 Hz), 6.52 (1H,d,J=3.2 Hz); 6.79–6.98 (2H,m), 7.02–7.20 (2H,m), 7.35–7.50 (1H,m), 7.50–7.68 (2H,m).

IR$\gamma_{max}^{neat}$ cm$^{-1}$: 3130, 3050, 2985, 1736, 1693, 1618, 1600, 1512.

SIMS (m/z): 361 (M+H)$^+$ (2R)-2-(2,4-Difluorophenyl)-2-[(1R)-1-[1-(4-fluorophenyl)-2-imidazolyloxy]ethyl]oxirane, colorless oil.

$^1$H-NMR (CDCl$_3$) δ:1.44 (3H,dd,J=6.4, 1.6 Hz), 2.88 (1H, d,J=4.8 Hz), 3.14 (1H,d,J=4.8 Hz), 5.16 (1H,q,J=6.4 Hz), 6.65–6.80 (4H,m), 7.01–7.19 (2H,m), 7.20–7.38 (3H, m).

IR$\gamma_{max}^{neat}$ cm$^{-1}$: 3060, 2980, 1698, 1618, 1601, 1539, 1514, 1462.

SIMS (m/z): 361 (M+H)$^+$

REFERENCE EXAMPLE 8

In the same manner as in Reference Example 5, starting from 1.36 g of (1S)-1-[(2R)-2-(2,4-difluorophenyl)-2-oxiranyl]ethanol and 1.06 g of 1-(2,4-difluorophenyl)-2(1H,3H)-imidazolone, 0.53 g of 1-[(1R,2S)-2-(2,4-difluorophenyl)-2,3-epoxy-1-methylpropyl]-3-(2,4-difluorophenyl)-2(1H, 3H)-imidazolone and 0.56 g of (2R)-2-(2,4-difluorophenyl)-2-[(1R)-1-[1-(2,4-difluorophenyl)-2-imidazolyloxy]ethyl]oxirane were obtained.

1-[(1R,2S)-2-(2,4-Difluorophenyl)-2,3-epoxy-1methylpropyl]-3-(2,4-difluorophenyl)-2(1H,3H)-imidazolone, pale yellow oil.

$^1$H-NMR (CDCl$_3$) δ: 1.38 (3H,d,J=7.2 Hz), 2.72 (1H,d, J=4.6 Hz), 2.83 (1H,d,J=4.6 Hz), 5.06 (1H,q,J=7.2 Hz), 6.44 (2H, s), 6.78–7.03 (4H,m), 7.42 (1H,m), 7.60 (1H,m).

IRγ$_{max}^{neat}$ cm$^{-1}$: 1699, 1616, 1519, 1430, 1267.

(2R)-2-(2,4-Difluorophenyl)-2-[(1R)-1-[1-(2,4-difluorophenyl)-2-imidazolyloxy]ethyl]oxirane, pale yellow oil.

$^1$H-NMR (CDCl$_3$) δ: 1.39 (3H,d,J=6.5 Hz), 2.87 (1H,d, J=5 Hz), 3.13 (1H,d,J=5 Hz), 5.14 (1H,q,J=6.5 Hz), 6.62–7, 05 (6H, m), 7.15–7.45 (2H,m).

IRγ$_{max}^{neat}$ cm$^{-1}$: 1705, 1616, 1549, 1520, 1462, 1435.

REFERENCE EXAMPLE 9

In the same manner as in Reference Example 5, starting from 1.35 g of (1S)-1-[(2R)-2-(2,4-difluorophenyl)-2-oxiranyl]ethanol and 963 mg of 4-(4-fluorophenyl)-3(2H,4H)-1,2,4-triazolone, 583 mg of 2-[(1R,2S)-2-(2,4-difluorophenyl)-2,3-epoxy-1-methylpropyl]-4-(4-fluorophenyl)-3(2H,4H)-1,2,4-triazolone was obtained as colorless needles.

m.p. 100°–101° C.

$^1$H-NMR (CDCl$_3$) δ: 1.47 (3H,d,J=7.2 Hz), 2.88 (1H,d, J=4.6 Hz), 3.16 (1H,d,J=4.6 Hz), 4.94 (1H,q,J=7.2 Hz), 6.70–6.91 (2H,m), 7.08–7.22 (2H,m), 7.25–7.51 (3H,m), 7.63 (1H,s).

IRγ$_{max}^{KBr}$ cm$^{-1}$: 3128, 3068, 2995, 1693, 1618, 1514, 1502, 1396.

Elemental analysis for C$_{18}$H$_{14}$F$_3$N$_3$O$_2$ Calcd: C 59.84, H 3.91, N 11.63 Found: C 59.85, H 3.93, N 11.74

REFERENCE EXAMPLE 10

In the same manner as in Reference Example 5, starting from 1.66 g of (1S)-1-[(2R)-2-(2,4-difluorophenyl)-2-oxiranyl]ethanol and 1.26 g of 1-(4-methoxyphenyl)-2(1H,3H)-imidazolone, 1-[(1R,2S)-2-(2,4-difluorophenyl)-2,3-epoxy-1-methylpropyl]-3-(4-methoxyphenyl)-2(1H,3H)-imidazolone (617 mg) was obtained as colorless prisms.

m.p. 150°–151° C.

$^1$H-NMR (CDCl$_3$) δ: 1.36 (3H,d,J=7.2 Hz), 2.70 (1H,d, J=4.8 Hz), 2.81 (1H,d,J=4.8 Hz), 3.82 (3H,s), 5.07 (1H,q, J=7.2 Hz), 6.41 (1H,d,J=3 Hz), 6.49 (1H,d,J=3 Hz), 6.78–6.95 (2H, m), 6.94 (2H,d,J=9 Hz), 7.35–7.50 (1H,m), 7.49 (2H,d,J=9 Hz).

IR γ$_{max}^{KBr}$ cm$^{-1}$: 3250, 3010, 1693, 1620, 1514, 1504, 1441.

Elemental analysis for C$_{20}$H$_{18}$F$_2$N$_2$O$_3$ Calcd: C 64.51, H 4.87, N 7.52 Found: C 64.26, H 4.97, N 7.46

REFERENCE EXAMPLE 11

In the same manner as in Reference Example 5, starting from 1.73 g of (1S)-1-[(2R)-2-(2,4-difluorophenyl)-2-oxiranyl] ethanol and 1.32 g of 4-(4 -methoxyphenyl)-(3-(2H, 4H)-1,2,4-triazolone, 2-[(1R,2S)-2-(2,4-difluorophenyl)-2,3-epoxy-1-methylpropyl]-4-(4-methoxyphenyl)-(3-(2H, 4H)-1,2,4-triazolone (869 mg) was obtained as a colorless oil.

$^1$H-NMR (CDCl$_3$) δ: 1.46 (3H,d,J=7 Hz), 2.88 (1H,d,J= 4.6 Hz), 3.16 (1H,d,J=4.6 Hz), 3.83 (3H,s), 4.95 (1H,q,J=7 Hz), 6.74–6.90 (2H,m), 6.96 (2H,d,J=9.2 Hz), 7.28–7.42 (1H,m), 7.36 (2H,d,J=9.2 Hz), 7.59 (1H,s).

IR$_{max}^{neat}$ cm$^{-1}$: 3100, 3005, 2920, 1699, 1616, 1601, 1556, 1519.

SIMS (m/z): 374 (M+H)$^+$

REFERENCE EXAMPLE 12

In the same manner as in Reference Example 5, starting from 1.36 g of (1S)-1-[(2R)-2-(2,4-difluorophenyl)-2-oxiranyl]ethanol and 1.32 g of 1-(4-trifluoromethoxyphenyl)-2-(1H,3H)-imidazolone, 1-[(1R,2S)-2-(2,4-difluorophenyl)-2,3-epoxy-1-methylpropyl]-3-(4-trifluoromethoxyphenyl)-(2(1H,3H)-imidazolone (0.60 g) and 0.46 g of (2R)-2-(2,4-difluorophenyl)-2-[(1R)-1-[1-(4-trifluoromethoxyphenyl)-2-imidazolyloxy]ethyl]oxirane were obtained.

1-[(1R,2S)-2-(2,4-Difluorophenyl)-2,3-epoxy-1-methylpropyl]-3-(4-trifluoromethoxyphenyl)-2(1H,3H)-imidazolone, colorless crystals.

m.p. 99°–100° C.

$^1$H-NMR (CDCl$_3$) δ: 1.37 (3H,d,J=7.2 Hz), 2.71 (1H,d,J= 4.8 Hz), 2.80 (1H, d, J=4.8 Hz), 5.07 (1H, q, J=7.2 Hz), 6.46 (1H, d,J=3.2 Hz), 6.56 (1H,d,J=3.2 Hz), 6.80–6.96 (2H,m), 7.28 (2H, d,J=9 Hz), 7.40 (1H,m), 7.67 (2H,d,J=9 Hz).

IR γ$_{max}^{KBr}$ cm$^{-1}$: 1682, 1620, 1606, 1516, 1433, 1253

(2R)-2-(2,4-Difluorophenyl)-2-[(1R)-1-[1-(4-trifluoromethoxyphenyl)-2-imidazolyloxy]ethyl]oxirane, pale yellow oil.

$^1$H-NMR (CDCl$_3$) δ: 1.45 (3H,dd,J=6.6 Hz, J=1.6 Hz), 2.90 (1H,d,J=5 Hz), 3.14 (1H,d,J=5 Hz), 5.19 (1H,q,J=6.6 Hz), 6.70–6.90 (4H,m), 7.18–7.50 (5H,m).

IRγ$_{max}^{neat}$ cm$^{-1}$: 1616, 1558, 1541, 1516, 1458, 1261.

REFERENCE EXAMPLE 13

In the same manner as in Reference Example 5, starting from 1.64 g of (1S)-1-[(2R)-2-(2,4-difluorophenyl)-2-oxiranyl]ethanol and 1.87 g of 4-(4-trifluoromethylphenyl)-3(2H, 4H)-1,2,4-triazolone, 2-[(1R,2S)-2-(2,4-difluorophenyl)-2,3-epoxy-1-methylpropyl]-4-(4-trifluoromethylphenyl)-3(2H,4H)-1,2,4-triazolone (1.26 g) was obtained as colorless crystals.

$^1$H-NMR (CDCl$_3$) δ: 1.48 (3H,d,J=7.4 Hz), 2.89 (1H,d, J=4.6 Hz), 3.16 (1H,d,J=4.6 Hz), 4.95 (1H,q,J=7.2 Hz), 6.74–6.90 (2H,m), 7.28–7.42 (1H,m), 7.64–7.86 (5H,m).

IRγ$_{max}^{KBr}$ cm$^{-1}$: 1620, 1390, 1320, 1110.

Elemental analysis for C$_{19}$H$_{14}$F$_5$N$_3$O$_2$ Calcd: C 55.48, H 3.43, N 10.22 Found: C 55.56, H 3.43, N 10.15

REFERENCE EXAMPLE 14

In the same manner as in Reference Example 5, starting from 2.49 g of (1S)-1-[(2R)-2-(2,4-difluorophenyl)-2-oxiranyl]ethanol and 2.52 g of 2-(4-trifluoromethylphenyl)-3(2H, 4H)-1,2,4-triazolone, 4-[(1R,2S)-2-(2,4-difluorophenyl)-2,3-epoxy-1-methylpropyl]-2-(4-trifluoromethylphenyl)-3(2H,4H)-1,2,4-triazolone (1.13 g) and 618 mg of (2R)-2-(2,4-difluorophenyl)-2-[(1R}-1-[1-(4-trifluoromethylphenyl)-1H-1,2,4-triazol-5-yloxy]ethyl]

oxirane were obtained.

4-[(1R,2S)-2-(2,4-difluorophenyl)-2,3-epoxy-1-methylpropyl]-2-(4-trifluoromethylphenyl)-3(2H,4H)-1,2,4-triazolone, colorless prisms.

m.p. 164°–165° C.

$^1$H-NMR (CDCl$_3$) δ: 1.44 (3H,d,J=7.2 Hz), 2.74 (1H,d, J=4.2 Hz), 2.78 (1H,d,J=4.2 Hz), 5.02 (1H,q,J=7.2 Hz), 6.80–7.01 (2H,m), 7.35–7.51 (1H,m), 7.64 (1H,s), 7.70 (2H,d,J=8.8 Hz), 8.18 (2H,d,J=8.8 Hz).

IRγ$_{max}^{KBr}$ cm$^{-1}$: 3060, 1722, 1619, 1601, 1564, 1524.

Elemental analysis for C$_{19}$H$_{14}$F$_5$N$_3$O$_2$ Calcd: C 55.48, H 3.43, N 10.22 Found: C 55.17, H 3.39, N 10.19

(2R)-2-(2,4-Difluorophenyl)-2-[(1R)-1-[(1-(4-trifluoromethylphenyl)-1H-1,2,4-triazol-5-yloxy]ethyl]oxirane, colorless oil.

$^1$H-NMR (CDCl$_3$) δ: 1.53 (3H,dd,J=6.6, 1.6 Hz), 2.94 (1H, d,J=4.8 Hz), 3.22 (1H,d,J=4.8 Hz), 5.37 (1H,q,J=6.6 Hz), 6.75–6.98 (2H,m), 7.38–7.52 (1H,m), 7.68 (1H,s), 7.70 (2H,d,J=8.4 Hz), 7.85 (2H,d,J=8.4 Hz).

IRγ$_{max}^{neat}$ cm$^{-1}$: 3050, 1618, 1599, 1558, 1540.

REFERENCE EXAMPLE 15

In the same manner as in Reference Example 5, starting from 1.36 g of (1S)-1-[(2R)-2-(2,4-difluorophenyl)-2-oxiranyl]ethanol and 1.33 g of 4-(4-trifluoromethoxyphenyl)-3(2H,4H)-1,2,4-triazolone, 2-[(1R,2S)-2-(2,4-difluorophenyl)-2,3-epoxy-1-methylpropyl]-4-(4-trifluoromethoxyphenyl)-3(2H,4H)-1,2,4-triazolone (1.45 g) was obtained as colorless prisms.

m.p. 103°–106° C.

$^1$H-NMR (CDCl$_3$) δ: 1.48 (3H,d,J=7 Hz), 2.88 (1H,d,J= 4.8 Hz), 3.16 (1H,d,J=4.8 Hz), 4.94 (1H,q,J=7 Hz), 6.72–6.92 (2H,m), 7.25–7.45 (3H,m), 7.56 (2H,d,J=9.2 Hz), 7.66 (1H,s).

IRγ$_{max}^{KBR}$ cm$^{-1}$: 3136, 3082, 1697, 1620, 1562, 1514, 1430, 1392, 1257, 1222.

REFERENCE EXAMPLE 16

In the same manner as in Reference Example 5, starting from 0.83 g of (1S)-1-[(2R)-2-(2,4-difluorophenyl)-2-oxiranyl]ethanol and 0.83 g of 1-(4-isopropylphenyl)-2(1H,3H)-imidazolone, 1-[(1R,2S)-2-(2,4-difluorophenyl)-2,3-epoxy-1-methylpropyl]-3-(4-isopropylphenyl)-2(1H,3H)-imidazolone (0.25 g) and 0.22 g of (2R)-2-(2,4-difluorophenyl)-2-[(1R)-1-[1-(4-isopropylphenyl)-2-imidazolyloxy]ethyl] oxiran were obtained.

1-[(1R,2S)-2-(2,4-Difluorophenyl)-2,3-epoxy-1-methylpropyl]-3-(4-isopropylphenyl)-2(1H,3H)-imidazolone, colorless crystals.

m.p. 119°–120° C.

$^1$H-NMR (CDCl$_3$) δ:1.25 (6H,d,J=7.0 Hz), 1.36 (3H,d,J= 7.4 Hz), 2.70 (1H,d,J=5 Hz), 2.81 (1H,d,J=5 Hz), 2.92 (1H, quintet,J=7.0 Hz), 5.08 (1H,q,J=7.4 Hz), 6.42 (1H,d,J=3.2 Hz), 6.54 (1H,d,J=3.2 Hz), 6.80–6.93 (2H,m), 7.27 (2H,d, J=8.6 Hz), 7.35–7.48 (1H,m), 7.52 (2H,d,J=8.6 Hz).

IRγ$_{max}^{KBr}$cm$^{-1}$: 2950, 1680, 1515, 1495, 1420.

(2R)-2-(2,4-Difluorophenyl)-2-[(1R)-1-[1-(4-isopropylphenyl)-2-imidazolyloxy]ethyl]oxirane, colorless oil.

$^1$H-NMR (CDCl$_3$) δ:1.30 (6H,d,J=7 Hz), 1.43 (3H,d,J= 6.6 Hz), 2.88 (1H,d,J=5.0 Hz), 2.97 (1H,q,J=7.0 Hz), 3.15 (1H, d,J=5.0 Hz), 5.14 (1H,q,J=6.6 Hz), 6.67–6.82 (4H,m), 7.26 (4H, s), 7.22–7.35 (1H,m).

REFERENCE EXAMPLE 17

In the same manner as in Reference Example 5, starting from 1.36 g of (1S)-1-[(2R)-2-(2,4-difluorophenyl)-2-oxiranyl]ethanol and 1.07 g of 4-(2,4-difluorophenyl)-3(2H,4H)-1,2,4-triazolone, 2-[(1R,2S)-2-(2,4-difluorophenyl)-2,3-epoxy-1-methylpropyl]-4-(2,4-difluorophenyl)-3(2H, 4H)-1,2,4-triazolone (1.20 g) was obtained as a colorless oil.

$^1$H-NMR (CDCl$_3$) δ: 1.48 (3H,d,J=7.2 Hz), 2.89 (1H,d,J= 4.6 Hz), 3.18 (1H,d,J=4.6 Hz), 4.94 (1H,q,J=7.2 Hz), 6.76–6.94 (2H,m), 6.95–7.10 (2H,m), 7.28–7.42 (1H,m), 7.50–7.65 (1H, m), 7.58 (1H,d,J=2.2 Hz).

IRγhd max$^{neat}$ cm$^{-1}$: 1716, 1616, 1558, 1519, 1427, 1403, 1270.

REFERENCE EXAMPLE 18

In the same manner as in Reference Example 5, starting from 2.27 g of (1S)-1-[(2R)-2-(2,4-difluorophenyl)-2-oxiranyl]ethanol and 1.80 g of 2-(4-fluorophenyl)-3(2H,4H)-1,2,4-triazolone, 4-[(1R,2S)-2-(2,4-difluorophenyl)-2,3-epoxy-1-methylpropyl]-2-(4-fluorophenyl)-3(2H,4H)-1,2,4-triazolone (848 mg) and 446 mg of (2R)-2-(2,4-difluorophenyl)-2-(1R)-1-[1-(4-fluorophenyl)-1H-1,2,4-triazol-5-yloxy]ethyl]oxirane were obtained.

4-[(1R,2S)-2-(2,4-Difluorophenyl)-2,3-epoxy-1-methylpropyl]-2-(4-fluorophenyl)-3(2H,4H)-1,2,4-triazolone, colorless prisms.

m.p. 163°–164° C.

$^1$H-NMR (CDCl$_3$) δ: 1.43 (3H,d,J=7.2 Hz), 2.73 (1H,d, J=4.2 Hz), 2.77 (1H,d,J=4.2 Hz), 5.01 (1H,q,J=7.2 Hz), 6.82–7.01 (2H,m), 7.12 (2H,t,J=8.8 Hz), 7.35–7.50 (1H,m), 7.60 (1H,s), 7.96 (2H,dd,J=8.8, 4.6 Hz).

IRγ$_{max}^{KBr}$ cm$^{-1}$: 3060, 1714, 1620, 1603, 1562, 1512.

Elemental analysis for C$_{18}$H$_{14}$F$_3$N$_3$O$_2$ Calcd: C 59.84, H 3.91, N 11.63 Found: C 59.51, H 3.83, N 11.83

(2R)-2-(2,4-Difluorophenyl)-2-[(1R)-1-[1-(4-fluorophenyl)-1H-1,2,4-triazol-5-yloxy]ethyl]oxirane, colorless oil.

$^1$H-NMR (CDCl$_3$) δ:1.50 (3H,dd,J=6.6, 1.6 Hz), 2.93 (1H, d, J=4.8 Hz), 3.20 (1H,d,J=4.8 Hz), 5.27 (1H,q,J=6.6 Hz), 6.76–6.98 (2H,m), 7.13 (2H,t,J=8.2 Hz), 7.30–7.49 (1H,m), 7.63 (2H,dd,J=4.6, 8.2 Hz), 7.64 (1H,s).

IRγ$_{max}^{neat}$ cm$^{-1}$: 3077, 2995, 1618, 1601, 1543.

REFERENCE EXAMPLE 19

In the same manner as in Reference Example 5, starting from 681 mg of (1S)-1-[(2R)-2-(2,4-difluorophenyl)-2-oxiranyl]ethanol and 1.0 g of 4-[4-(4-benzyl-1-piperazinyl)phenyl]-3(2H,4H)-1,2,4-triazolone, 2-[(1R,2S)-2-(2,4-difluorophenyl)-2,3-epoxy-1-methylpropyl]-4-[4-(4-benzyl-1-piperazinyl)phenyl]-3(2H,4H)-1,2,4-triazolone (293 mg) was obtained as a colorless powder.

$^1$H-NMR (CDCl$_3$) δ:1.45 (3H,d,J=7 Hz), 2.61 (4H,t,J=4.8 Hz), 2.87 (1H, d, J=4.8 Hz 3.16 (1H,d,J=4.8 Hz), 3.22 (4H, t, J=4.8 Hz), 3.57 (2H,s), 4.96 (1H,q,J=7 Hz), 6.72–6.91 (2H, m), 6.94 (2H,d,J=9 Hz), 7.21–7.45 (8H,m), 7.57 (1H,s).

REFERENCE EXAMPLE 20

In the same manner as in Reference Example 5, starting from 1.72 g of (1S)-1-[(2R)-2-(2,4-difluorophenyl)-2-oxiranyl]ethanol and 1.68 g of 4-(4-isopropylphenyl)-3(2H,4H)-1,2,4-triazolone, an about 1:1 mixture (0.89 g) of 2-[(1R, 2S)-2-(2,4-difluorophenyl)-2,3-epoxy-1-methylpropyl]-4-(4-isopropylphenyl)-3 (2H, 4H)-1,2,4-triazolone and (1R)-1-[(2R)-2-(2,4-difluorophenyl)-2-oxiranyl]ethanol was obtained.

¹H-NMR (CDCl₃) δ:1.16 (dd,J=6.6, 1.0 Hz), 1.25 (d,J= 6.8 Hz), 1.46 (d,J=7 Hz), 1.78 (d, J=8 Hz), 2.79 (d, J=5 Hz), 2.88 (d,J=5 Hz), 2.94 (q,J=6.8 Hz), 3.16 (d,J=5 Hz), 3.30 (d,J=5 Hz), 4.02–4.17 (m), 4.96 (q,J=7 Hz), 6.73–6.92 (m), 7.27–7.45 (m), 7.62 (s).

REFERENCE EXAMPLE 21

In the same manner as in Reference Example 5, starting from 1.41 g of (1S)-1-[(2R)-2-(2,4-difluorophenyl)-2-oxiranyl]ethanol and 1.30 g of 1-(4-trifluoromethylphenyl)-5(1H, 4H)-tetrazolone, 1-[(1R,2S)-2-(2,4-difluorophenyl)-2,3-epoxy-1-methylpropyl]-4-(4-trifluoromethylphenyl)-5-(1H, 4H)-tetrazolone (1.38 g) and 0.168 g of (2R)-2-(2,4-difluorophenyl)-2-[(1R)-1-[1-(4-trifluoromethylphenyl)-1H-tetrazol-5-yloxy]ethyl]oxirane were obtained.

1-[(1R,2S)-2-(2,4-Difluorophenyl)-2,3-epoxy-1-methylpropyl]-4-(4-trifluoromethylphenyl)-5-(1H,4H)tetrazolone, colorless oil.

¹H-NMR (CDCl₃) δ1.61 (3H,d,J=7.2 Hz), 2.93 (1H,d,J= 4.6 Hz), 3.16 (1H, d, J=4.6 Hz), 4.97 (1H,q,J=7.2 Hz), 6.72–6.94 (2H,m), 7.23–7.40 (1H,m), 7.75 (2H,d,J=8.4 Hz), 8.13 (2H,d,J=8.4 Hz)

IRγ$_{max}^{neat}$ cm⁻¹: 3100, 1734, 1618, 1522, 1508, 1429.

SIMS (m/z): 413 (M+H)⁺

(2R)-2-(2,4-Difluorophenyl)-2-[(IR)-1-[1-(4-trifluoromethylphenyl)- 1H-tetrazol-5-yloxy]ethyl]oxirane, colorless oil.

¹H-NMR (CDCl₃) δ:1.59 (3H,dd,J=6.6, 1.6 Hz), 2.98 (1H, d,J=4.6 Hz), 3.23 (1H,d,J=4.6 Hz), 5.39 (1H,q,J=6.6 Hz), 6.75–6.98 (2H,m), 7.32–7.49 (1H,m), 7.80 (2H,d,J=9 Hz), 7.82 (2H, d,J=9 Hz).

SIMS (m/z): 413 (M+H)⁺

REFERENCE EXAMPLE 22

In the same manner as in Reference Example 5, starting from 0.50 g of (1S)-1-[(2R)-2-(2,4-difluorophenyl)-2-oxiranyl]ethanol and 0.72 g of 1-[4-(2,2,3,3-tetrafluoropropoxy)phenyl]-2(1H, 3H)-imidazolone, 1-[(1R,2S)-2-(2,4-difluorophenyl)-2,3-epoxy-1-methylpropyl]-3-[4-(2,2,3,3-tetrafluoropropoxy)phenyl]-2(1H,3H)-imidazolone (0.21 g) and 0.14 g of (2R)-2-(2,4-difluorophenyl)-2-[(1R)-1-[1-(4-(2,2,3,3-tetrafluoropropoxy)phenyl]-2-imidazolyloxy]ethyl] oxirane were obtained.

1-[(1R,2S)-2-(2,4-Difluorophenyl)-2,3-epoxy-1-methylpropyl]-3-[4-(2,2,3,3-tetrafluoropropoxy)phenyl]-2(1H, 3H)-imidazolone.

¹H-NMR (CDCl₃) γ:1.36 (3H,d,J=7.2 Hz), 2.70 (1H,d,J= 4.7 Hz), 2.81 (1H,d,J=4.7 Hz), 4.36 (2H,t,J=12 Hz), 5.07 (1H, q,J=7.2 Hz), 6.06 (1H,tt,J=4.8, 53 Hz), 6.43 (1H,d,J=3 Hz), 6.51 (1H,d,J=3 Hz), 6.79–7.02 (4H,m), 7.26–7.47 (1H, m), 7.52–7.60 (2H,m).

(2R)-2-(2,4-Difluorophenyl)-2-[(1R)-1-[1-[4-(2,2,3,3-tetrafluoropropoxy)phenyl]-2-imidazolyloxy]ethyl]oxirane.

¹H-NMR (CDCl₃) δ: 1.43 (3H,d,J=6.6 Hz), 2.86 (1H,d, J=5.2 Hz), 3.14 (1H,d,J=5.2 Hz), 4.32–4.47 (2H,m), 5.19 (1H,q,J=6.6 Hz), 6.09 (1H,tt,J=4.8, 53 Hz), 6.72–6.83 (4H, m), 6.90–7.02 (2H,m), 7.24–7.47 (3H,m).

REFERENCE EXAMPLE 23

In the same manner as in Reference Example 5, starting from 543 mg of (1S)-1-[(2R)-2-(2,4-difluorophenyl)-2-oxiranyl]ethanol and 809 mg of 4-[4-[4-(4-methoxyphenyl)-1-piperazinyl]phenyl]-3(2H,4H)-1,2,4-triazolone prepared by a method described in Journal of Medicinal Chemistry, vol. 27, page 894 (1984), 2-[(1R,2S)-2-(2,4-difluorophenyl)-2, 3-epoxy-1-methylpropyl]-4-[4-[4-(4-methoxyphenyl)-1-piperazinyl]phenyl]-3(2H,4H)-1,2,4-triazolone (373 mg) was obtained as colorless prisms.

m.p. 175°–176° C.

¹H-NMR (CDCl₃) δ: 1.46 (3H,d,J=7.2 Hz), 2.88 (1H,d, J=4.8 Hz), 3.16 (1H,d,J=4.8 Hz), 3.17–3.30 (8H,m), 3.79 (3H,s), 4.96 (1H,q,J=7.2 Hz), 6.73–6.96 (2H,m), 6.87 (2H, d,J=9.2 Hz), 6.96 (2H,d,J=9.2 Hz), 7.01 (2H,d,J=8.8 Hz), 7.34 (2H,d,J=8.8 Hz), 7.24–7.41 (1H,m), 7.58 (1H,s).

Elemental analysis for $C_{29}H_{29}F_2N_5O_3$ Calcd: C 65.28, H 5.48, N 13.13 Found: C 65.30, H 5.50, N 13.03

REFERENCE EXAMPLE 24

In the same manner as in Reference Example 5, starting from 1.2 g of (1S)-1-[(2R)-2-(2,4-difluorophenyl)-2-oxiranyl]ethanol and 1.1 g of 4-(3-trifluoromethylphenyl)- 3(2H, 4H)-1,2,4-triazolone, 2-[(1R,2S)-2-(2,4-difluorophenyl)-2, 3-epoxy-1-methylpropyl]-4-(3-trifluoromethylphenyl)-3(2H,4H)-1,2,4-triazolone (0.85 g) was obtained as a colorless powder.

¹H-NMR (CDCl₃) δ:1.47 (3H,d,J=7 Hz), 2.89 (1H,d,J= 4.6 Hz), 3.16 (1H,d,J=4.6 Hz), 4.95 (1H,q,J=7 Hz), 6.75–6.90 (3H,m), 7.28–7.45 (2H,m), 7.73 (1H,s), 7.71–7.82 (2H,m).

REFERENCE EXAMPLE 25

In the same manner as in Reference Example 5, starting from 1.43 g of (1S)-1-[(2R)-2-(2,4-difluorophenyl)-2-oxiranyl]ethanol and 1.03 g of 1-(4-fluorophenyl)-5(1H,4H)-tetrazolone, 1-[(1R,2S)-2-(2,4-difluorophenyl)-2,3-epoxy-1-methylpropyl]-4-(4-fluorophenyl)-5(1H,4H)-tetrazolone (1.22 g) and 205 mg of (2R)-2-(2,4-difluorophenyl)-2-[(1R)-1-[1-(4-fluorophenyl)-1H-tetrazol-5-yloxy]ethyl]oxirane were obtained.

1-[(1R,2S)-2-(2,4-Difluorophenyl)-2,3-epoxy-1-methylpropyl]-4-(4-fluorophenyl)-5(1H,4H)-tetrazolone, colorless oil.

¹H-NMR (CDCl₃) δ: 1.60 (3H,d,J=7.2H), 2.93 (1H,d,J= 4.4 Hz), 3.17 (1H,d,J=4.4 Hz), 4.93 (1H,q,J=7.2 Hz), 6.75–6.92 (2H,m), 7.10–7.40 (3H,m), 7.82–7.99 (2H,m).

SIMS (m/z): 363 (M+H)⁺

(2R)-2-(2,4-Difluorophenyl)-2-[(1R)-1-[1-(4-fluorophenyl)-1H-tetrazol-5-yloxy]ethyl]oxirane, colorless oil, ¹H-NMR (CDCl₃) δ: 1.56 (3H,dd,J=6.6, 1.6 Hz), 2.96 (1H, d,J=4 6 Hz), 3.20 (1H,d,J=4.6 Hz), 5.31 (1H,q,J=6.6 Hz), 6.74–6.96 (2H,m), 7.23 (2H,t,J=9 Hz), 7.30–7.49 (1H, m), 7.65 (2H,dd,J=9, 4.6 Hz).

SIMS (m/z): 363 (M+H)⁺

REFERENCE EXAMPLE 26

In the same manner as in Reference Example 5, starting from 1.42 g of (1S)-1-[(2R)-2-(2,4-difluorophenyl)-2-oxiranyl]ethanol and 0.92 g of 4-(4-pyridyl)-3(2H,4H)-1,2,4-triazolone, 2-[(1R,2S)-2-(2,4-difluorophenyl)-2,3-epoxy-1-methylpropyl]-4-(4-pyridyl)-3(2H,4H)-1,2,4-triazolone (0.66 g) was obtained as colorless prisms.

m.p. 96°–97° C.

¹H-NMR (CDCl₃) δ: 1.47 (3H,d,J=7 Hz), 2.88 (1H,d,J= 4.6 Hz), 3.15 (1H,d,J=4.6 Hz), 4.93 (1H,q,J=7 Hz), 6.72–6.91 (2H,m), 7.26–7.40 (1H,m), 7.62 (2H,dd,J=4.8, 1.6 Hz), 7.83 (1H,s), 8.70 (2H,dd,J=4.8, 1.6 Hz).

Elemental analysis for $C_{17}H_{14}F_2N_4O_2$ Calcd: C 59.30, H 4.10, N 16.27 Found: C 59.23, H 4.12, N 16.36.

REFERENCE EXAMPLE 27

In the same manner as in Reference Example 5, starting from 536 mg of (1S)-1-[(2R)-2-(2,4-difluorophenyl)-2-oxiranyl]ethanol and 305 mg of 4-(4-pyrimidinyl)-3(2H,4H)-1,2,4-triazolone, 2-[(1R,2S)-2-(2,4-difluorophenyl)-2,3-epoxy-1methylpropyl]-4-(4-pyrimidinyl)-3(2H,4H)-1,2,4-triazolone (199 mg) was obtained as a colorless oil.

$^1$H-NMR (CDCl$_3$) δ: 1.47 (3H,d,J=7.2 Hz), 2.90 (1H,d, J=4.6 Hz), 3.16 (1H,d,J=4.6 Hz), 4.90 (1H,q,J=7.2 Hz), 6.72–6.90 (2H,m), 7.25–7.40 (1H,m), 8.34 (1H,dd,J=5.6, 1.2 Hz), 8.46 (1H,s), 8.80 (1H,d,J=5.6 Hz), 9.03 (1H,d,J=1.2 Hz). SIMS (m/z): 346 (M+H)$^+$.

REFERENCE EXAMPLE 28

In the same manner as in Reference Example 5, starting from 1.36 g of (1S)-1-[(2R)-2-(2,4-difluorophenyl)-2-oxiranyl]ethanol and 0.91 g of 4-(2,2,2-trifluoroethyl)-3(2H,4H)-1,2,4-triazolone, 2-[(1R,2S)-2-(2,4-difluorophenyl)2,3-epoxy-1-methylpropyl]-4-(2,2,2-trifluoroethyl)-3(2H,4H)-1,2,4-triazolone (1.25 g) was obtained as a colorless oil.

IRγcm$^{-1}$ (film): 1716, 1704, 1652,1616, 1558, 1508.

$^1$H-NMR (CDCl$_3$) δ: 1.43 (3H,d,J=7 Hz), 2.86 (1H,d,J= 4.6 Hz), 3.11 (1H,d,J=4.6 Hz), 4.05–4.35 (2H,m), 4.87 (1H,q,J=7 Hz), 6.70–6.90 (2H,m), 7.20–7.25 (1H,m), 7.46 (1H,s).

REFERENCE EXAMPLE 29

In the same manner as in Reference Example 5, starting from 1.0 g of (1S)-1-[(2R)-2-(2,4-difluorophenyl)-2-oxiranyl]ethanol and 1.16-g of 4-[4-(2,2,3,3-tetrafluoropropoxy)phenyl]-3(2H,4H)-1,2,4-triazolone, 2-[(1R,2S)-2-(2,4-difluorophenyl)-2,3-epoxy-1-methylpropyl]-4-[4-(2,2,3,3-tetrafluoropropoxy)phenyl]-3(2H,4H)-1,2,4-triazolone (1.34 g) was obtained as a colorless oil.

IRγcm$^{-1}$ (film): 1716, 1705, 1616, 1558, 1516, 1257, 1108.

$^1$H-NMR (CDCl$_3$) δ:1.47 (3H,d,J=7 Hz), 2.88 (1H,d,J= 4.8 Hz), 3.16 (1H,d,J=4.8 Hz), 4.38 (2H,t,J=11.8 Hz), 4.94 (1H,q, J=7 Hz), 6.07 (1H,tt,J=53 Hz,J=4.8 Hz), 6.75–6.90 (2H,m), 6.95–7.12 (2H,m), 7.28–7.55 (3H,m), 7.63 (1H,s).

REFERENCE EXAMPLE 30

In the same manner as in Reference Example 5, starting from 1.0 g of (1S)-1-[(2R)-2-(2,4-difluorophenyl)-2-oxiranyl]ethanol and 1.1 g of 4-(2-trifluoromethylphenyl)-3(2H,4H)-1,2,4-triazolone, 2-[(1R,2S)-2-(2,4-difluorophenyl)-2,3-epoxy-1-methylpropyl]-4-(2-trifluoromethylphenyl)-3(2H,4H)-1,2,4-triazolone (0.4 g) was obtained as a colorless powder.

$^1$H-NMR (CDCl$_3$) δ:1.48 3H,d,J=7.2 Hz), 2.91 (1H,d,J= 4.4 Hz), 3.19 (1H,d,J=4.4 Hz), 4.97 (1H,q,J=7.2 Hz), 6.75–6.90 (2H,m), 7.29–7.45 (3H,m), 7.56–7.84 (3H,m).

REFERENCE EXAMPLE 31

In the same manner as in Reference Example 5, starting from 1.43 g of (1S)-1-[(2R)-2-(2,4-difluorophenyl)-2-oxiranyl]ethanol and 0.94 g of 4-(4-isopropoxyphenyl)-3(2H,4H)-1,2,4-triazolone, 2-[(1R,2S)-2-(2,4-difluorophenyl)-2,3-epoxy-1-methylpropyl]-4-(4-isopropoxyphenyl)-3(2H,4H)-1,2,4-triazolone (0.84 g) was obtained as a colorless oil.

$^1$H-NMR (CDCl$_3$) δ:1.34 (6H,d,J=6.2 Hz), 1.46 (3H,d,J= 7.2 Hz), 2.88 (1H,d,J=4.6 Hz), 3.17 (1H,d,J=4.6 Hz), 4.56 (1H, septet, J=6.2 Hz), 4.96 (1H,q,J=7.2 Hz), 6.72–6.91 (2H,m), 6.94 (2H,d,J=8.4 Hz), 7.28–7.40 (1H,m), 7.34 (2H, d,J=8.4 Hz), 7.58 (1H,s).

SIMS (m/z): 402 (M+H)$^+$.

REFERENCE EXAMPLE 32

In the same menner as in Reference Example 5, starting from 1.38 g of (1S)-1-[(2R)-2-(2,4-difluorophenyl)-2-oxiranyl]ethanol and 1.21 g of 4-(3-methylbutyl)-3(2H,4H)-1,2,4-triazolone, 2-[(1R, 2S)-2-(2,4-Difluorophenyl)-2,3-epoxy-1-methylpropyl]-4-(3-methylbutyl)-3 (2H, 4H)-1,2,4-triazolone (1.15 g) was obtained as a colorless oil.

$^1$H-NMR (CDCl$_3$) δ: 0.94 (6H,dd,J=6.2, 1.8 Hz), 1.41 (3H,d, J=7.2 Hz), 1.40–1.70 (3H,m), 2.85 (1H,d,J=4.6 Hz), 3.10 (1H, d,J=4.6 Hz), 3.59 (2H,t,J=6.2 Hz), 4.91 (1H,q,J= 7.2 Hz), 6.67–6.79 (2H,m), 7.33 (1H,s), 7.72–7.39 (1H,m).

SIMS (m/z): 338 (M+H)$^+$.

REFERENCE EXAMPLE 33

In the same manner as in Reference Example 5, starting from 1.0 g of (1S)-1-[(2R)-2-(2,4-difluorophenyl)-2-oxiranyl]ethanol and 1.11 g of 4-[4-(1,1,2,2-tetrafluoroethoxy)phenyl]-3(2H,4H)-1,2,4-triazolone, 2-[(1R,2S)-2-(2,4-difluorophenyl)-2,3-epoxy-1-methylpropyl]-4-[4-(1,1,2,2-tetrafluoroethoxy)phenyl]-3(2H,4H)-1,2,4-triazolone (0.99 g) was obtained as a colorless oil.

IR γcm$^{-1}$ (film): 1699, 1619, 1600, 1554, 1510, 1400.

$^1$H-NMR (CDCl$_3$) δ:1.47 (3H,d,J=7.2H), 2.89 (1H,d,J= 4.6 Hz), 3.16 (1H,d,J=4.6 Hz), 4.95 (1H,q,J=7.2 Hz), 5.93 (1H, tt,J=53 Hz,J=2.8 Hz), 6.74–6.90 (2H,m), 7.25–7.45 (3H,m), 7.55 (2H,dt,J=9 Hz,J=2.2 Hz), 7.67 (1H,s).

REFERENCE EXAMPLE 34

In the same manner as in Reference Example 5, starting from 1.34 g of (1S)-1-[(2R)-2-(2,4-difluorophenyl)-2-oxiranyl-] ethanol and 1.15 g of 2-(4-chlorophenyl)-3(2H,4H)-1, 2,4-triazolone, 2-(4-chlorophenyl)-4-[(1R,2S)-2-(2,4-difluorophenyl)-2,3-epoxy-1-methylpropyl]-3(2H,4H)-1,2,4-triazolone (519 mg) and 424 mg of (2R)-2-[(1R)-1-[1-(4-chlorophenyl)-1H-1,2,4-triazol-5-yloxy]ethyl]-2-(2,4-difluorophenyl)oxirane were obtained.

2-(4-Chlorophenyl)-4-[(1R,2S)-2-(2,4-difluorophenyl)-2,3-epoxy-1-methylpropyl]-3(2H,4H)-1,2,4-triazolone, colorless prisms.

m.p. 172°–173° C.

$^1$H-NMR (CDCl$_3$) δ:1.42 (3H,d,J=7.4 Hz), 2.73 (1H,d,J= 4.4 Hz), 2.77 (1H,d,J=4.4z), 5.00 (1H,q,J=7.4 Hz), 6.81–6.99 (2H,m), 7.32–7.48 (1H,m), 7.39 (2H,d,J=9 Hz), 7.60 (1H,s), 7.96 (2H,d,J=9 Hz).

Elemental analysis for $C_{18}H_{14}ClF_2N_3O_2 \cdot 0.5H_2O$ Calcd: C 55.90, H 3.91, N 10.86 Found: C 56.20, H 3.69, N 10.93

(2R)-[(1R)-1-[l=(4-Chlorophenyl)-1H-1,2,4-triazol-5-yloxy]ethyl]-2-(2,4-difluorophenyl)oxirane, colorless oil.

$^1$H-NMR (CDCl$_3$) δ:1.51 (3H,dd,J=6.6, 1.6 Hz), 2.93 (1H, d,J=4.6 Hz), 3.20 (1H,d,J=4.6 Hz), 5.30 (1H,q,J=6.6 Hz), 6.78–6.96 (2H,m), 7.31–7.46 (1H,m), 7.40 (2H,d,J=9 Hz), 7.62 (2H, d,J=9 Hz), 7.64 (1H,s).

SIMS (m/z): 378 (M+H)$^+$.

REFERENCE EXAMPLE 35

In the same manner as in Reference Example 5, starting from 1.53 g of (1S)-1-[(2R)-2-(2,4-difluorophenyl)-2-oxiranyl] ethanol and 1.50 g of 2-(4-trifluoromethoxyphenyl)-3(2H,4H)-1,2,4-triazolone, 4-[(1R,2S)-2-(2,4-difluorophenyl)-2,3-epoxy-1-methylpropyl]-2-(4-trifluoromethoxyphenyl)-3(2H,4H)-1,2,4-triazolone (829 mg) and 778 mg of (2R)-2-(2,4-difluorophenyl)-2-[(1R)-1-[1-(4-trifluoromethoxyphenyl)-1H-1,2,4-triazol-5-yloxy] ethyl]oxirane were obtained.

4-[(1R,2S)-2-(2,4-Difluorophenyl)-2,3-epoxy-1methylpropyl]-2-(4-trifluoromethoxyphenyl)-3(2H,4H)-1,2,4-triazolone, colorless prisms.

m.p. 116°–117 ° C.

$^1$H-NMR (CDCl$_3$) δ:1.43 (3H,d,J=7.2 Hz), 2.74 (1H,d, J=4 Hz), 2.77 (1H,d,J=4 Hz), 5.01 (1H,q,J=7.2 Hz), 6.80–7.00 (2H, m), 7.28 (2H,d,J=9.2 Hz), 7.33–7.50 (1H,m), 7.61 (1H,s), 8.05 (2H,d,J=9.2 Hz).

Elemental analysis for C$_{19}$H$_{14}$F$_5$N$_3$O$_3$ Calcd: C 53.40, H 3.30, N 9.83 Found: C 53.09, H 3.23, N 9.83.

(2R)-2-(2,4-Difluorophenyl)-2-[(1R)-1-[1-(4-trifluoromethoxyphenyl)-1H-1,2,4-triazol-5-yloxy]ethyl]oxirane, colorless oil.

$^1$H-NMR (CDCl$_3$) δ:1.51 (3H,d,J=6.6 Hz), 2.94 (1H,d,J= 4.8 Hz), 3.20 (1H,d,J=4.8 Hz), 5.31 (1H,q,J=6.6 Hz), 6.78–6.98 (2H,m), 7.29 (2H,d,J=9 Hz), 7.35–7.50 (1H,m), 7.65 (1H,s), 7.71 (2H,d,J=9 Hz).

SIMS (m/z): 428 (M+H)$^+$

REFERENCE EXAMPLE 36

In the same manner as in Reference Example 5, starting from 1.54 g of (1S)-1-[(2R)-2-(2,4-difluorophenyl)-2-oxiranyl]ethanol and 1.52 g of 1-(4-trifluoromethoxyphenyl)-5(1H,4H)-tetrazolone, 1.76 g of 1-[(1R,2S)-2-(2,4-difluorophenyl)-2,3-epoxy-1-methylpropyl]-4-(4-trifluoromethoxyphenyl)-5(1H,4H)-tetrazolone was obtained as a colorless oil.

$^1$H-NMR (CDCl$_3$) δ:1.60 (3H,d,J=7.4 Hz), 2.93 (1H,d,J= 4.4 Hz), 3.17 (1H,d,J=4.4 Hz), 4.93 (1H,q,J=7.4 Hz), 6.75–6.96 (2H,m), 7.24–7.43 (1H,m), 7.35 (2H,d,J=9.2 Hz), 8.00 (2H,d,J=9.2 Hz).

IR γ$_{max}^{neat}$ cm$^{-1}$: 2980, 1732, 1620, 1601, 1514, 1427.

SIMS (m/z): 429(M+H)$^+$

REFERENCE EXAMPLE 37

In the same manner as in Reference Example 5, starting from 1.39 g of (1S)-1-[(2R)-2-(2,4-difluorophenyl)-2-oxiranyl]ethanol and 1.63-g of 1-[4-(2,2,3,3-tetrafluoropropoxy)phenyl]-5(1H,4H)-tetrazolone, 1.27 g of 1-[(1R,2S)-2-(2,4-difluorophenyl)-2,3-epoxy-1-methylpropyl]-4-[4-(2,2,3,3-tetrafluoropropoxy)phenyl]-5(1H,4H)-tetrazolone was obtained as a colorless oil.

$^1$H-NMR (CDCl$_3$) δ:1.60 (3H,d,J=7.2 Hz), 2.93 (1H,d,J= 4.4 Hz), 3.17 (1H,d,J=4.4 Hz), 4.40 (2H,t,J=11.8Hz), 4.93 (1H, q,J=7.2 Hz), 6.08 (1H,tt,J=53.2, 4.6 Hz), 6.73–6.94 (2H,m), 7.05 (2H,d,J=9 Hz), 7.23–7.41 (1H,m), 7.86 (2H, d,J=9 Hz).

IR γ$_{max}^{neat}$ cm$^{-1}$: 3000, 1745, 1622, 1601, 1522, 1431.

SIMS (m/z): 475 (M+H)$^+$

REFERENCE EXAMPLE 38

In the same manner as in Reference Example 5, starting from 1.38 g of (1S)-1-[(2R)-2-(2,4-difluorophenyl)-2-oxiranyl]ethanol and 1.09 g of 1-(4-chlorophenyl)-5(1H,4H)-tetrazolone, 1.27 g of 1-(4-chlorophenyl)-4-[(1R,2S)-2-(2,4-difluorophenyl)-2,3-epoxy-1-methylpropyl]-5(1H,4H)-tetrazolone was obtained as a cololess oil.

$^1$H-NMR (CDCl$_3$) δ:1.60 (3H,d,J=7.2 Hz), 2.92 (1H,d,J= 4.4 Hz), 3.16 (1H,d,J=4.4 Hz), 4.92 (1H,q,J=7.2 Hz), 6.75–6.96 (2H,m), 7.25–7.41 (1H,m), 7.45 (2H,d,J=9 Hz), 7.90 (2H,d,J=9 Hz).

IR γ$_{max}^{neat}$ cm$^{-1}$: 3018, 1732, 1620, 1506, 1425.

SIMS (m/z): 379 (M+H)$^+$

REFERENCE EXAMPLE 39

In the same manner as in Reference Example 5, starting from 1.01 g of (1S)-1-[(2R)-(2,4-difluorophenyl)-2oxiranyl] ethanol and 1.15 g of 1-[4-(1,1,2,2tetrafluoroethoxy)phenyl]-2(1H,3H)-imidazolone, 0.36 g of 1-[(1R,2S)-2-(2,4-difluorophenyl)-2,3-epoxy-1-methylpropyl]-3-[4-(1,1,2,2-tetrafluoroethoxy)phenyl]-2(1H,3H)-imidazolone was obtained as colorless needles.

m.p. 117°–118° C.

$^1$H-NMR (CDCl$_3$) δ:1.37 (3H,d,J=7.2 Hz), 2.71 (1H,d, J=5 Hz), 2.81 (1H,d,J=5 Hz), 5.08 (1H,q,J=7.2 Hz), 5.93 (1H,tt,J= 53, 2.8 Hz), 6.46 (1H,d,J=3 Hz), 6.57 (1H,d,J=3 Hz), 6.80–6.95 (2H,m), 7.28 (2H,d,J=9 Hz), 7.36–7.48 (1H, m), 7.67 (2H,d,J=9 Hz).

REFERENCE EXAMPLE 40

In the same manner as in Reference Example 5, starting from 0.80 g of (1S)-1-[(2R)-2-(2,4-difluorophenyl)-2-oxiranyl]ethanol and 0.78 g of 1-(4-chlorophenyl)-2(1H,3H)-imidazolone, 0.18 g of 1-(4-chlorophenyl)-3-[(1R,2S)-2-(2,4-difluorophenyl)-2,3-epoxy-1-methylpropyl]- 2(1H,3H)-imidazolone was obtained as a colorless viscous oil.

$^1$H-NMR (CDCl$_3$) δ:1.36 (3H,d,J=7 Hz), 2.70 (1H,d,J=5 Hz), 2.80 (1H,d,J=5 Hz), 5.07 (1H,q,J=7 Hz), 6.45 (1H,d, J=3.2 Hz), 6.55 (1H,d,J=3.2 Hz), 6.79–6.94 (2H,m), 7.34–7.46 (1H,m), 7.38 (2H,d,J=9 Hz), 7.59 (2H,d,J=9 Hz).

REFERENCE EXAMPLE 41

In the same manner as in Reference Example 5, starting from 0.66 g of (1S)-1-[(2R)-2-(2,4-difluorophenyl)-2-oxiranyl]ethanol and 0.65 g of 4-(4-chlorophenyl)-3(2H,4H)-1,2,4-triazolone, 0.23 g of 4-(4-chlorophenyl)-2-[(1R,2S)-2-(2,4-difluorophenyl)-2,3-epoxy-1-methylpropyl]-3(2H,4H)-1,2,4-triazolone was obtained as a colorless viscous oil.

$^1$H-NMR (CDCl$_3$) δ:1.46 (3H,d,J=7 Hz), 2.88 (1H,d,J=5 Hz), 3.15 (1H,d,J=5 Hz), 4.94 (1H,q,J=7 Hz), 6.76–6.88 (2H, m), 7.26–7.50 (1H,m), 7.46 (4H,s), 7.66 (1H,s).

REFERENCE EXAMPLE 42

In the same manner as in Reference Example 5, starting from 0.83 g of (1S)-1-[(2R)-2-(2,4-difluorophenyl)-2-oxiranyl]ethanol and 1.56 g of 1-[4-(2,2,3,3,4,4,5,5-octafluoropentoxy)phenyl]-2(1H,3H)-imidazolone, 0.30 g of 1-[(1R, 2S)-2-(2,4-difluorophenyl)-2,3-epoxy-1-methylpropyl]-3-(4-(2,2,3,3,4,4,5,5-octafluoropentoxy)phenyl]-2(1H,3H)-imidazolone was obtained as a colorless viscous oil.

$^1$H-NMR (CDCl$_3$) δ:1.36 (3H,d,J=7.2 Hz), 2.70 (1H,d,J= 4.8 Hz), 2.80 (1H,d,J=4.8 Hz), 4.48 (2H,t,J=13 Hz), 5.07 (1H, q,J=7.2 Hz), 6.09 (1H,tt,J=52, 5.6 Hz), 6.43 (1H,d,J= 3.2 Hz), 6.51 (1H,d,J=3.2 Hz), 6.79–6.96 (2H,m), 7.00 (2H,d,J=9 Hz), 7.34–7.47 (1H,m), 7.57 (2H,d,J=9 Hz).

REFERENCE EXAMPLE 43

In the same manner as in Reference Example 5, starting from 0.68 g of (1S)-1-[(2R)-(2,4-difluorophenyl)-2oxiranyl] ethanol and 0.70 g of 1-[4-(2,2,2-trifluoroethoxy)phenyl]-2(1H,3H)-imidazolone, 0.30 g of 1-(1R,2S)-2-(2,4-difluorophenyl)-2,3-epoxy-1-methylpropyl]-3-[4-(2,2,2-trifluoroethoxy)phenyl]-2(1H,3H)-imidazolone was obtained as colorless needles.

$^1$H-NMR (CDCl$_3$) δ:1.36 (3H,d,J=7.2 Hz), 2.71 (1H,d,J=4.8 Hz), 2.81(1H,d,J=4.8 Hz), 4.37 (2H,q,J=8 Hz), 5.07 (1H,q,J=7.2 Hz), 6.52 (1H,d,J=3.2 Hz), 6.43 (1H,q,J=3.2 Hz), 6.80–6.95 (2H,m), 7.00 (2H,d,J=9.2 Hz), 7.35–7.48 (1H,m), 7.57 (2H,d,J=9.2 Hz).

REFERENCE EXAMPLE 44

In the same manner as in Reference Example 5, starting from 1.0 g of (1S)-1-[(2R)-(2,4-difluorophenyl)-2-oxiranyl] ethanol and 1.23 g of 1-[4-(2,2,3,3,3-pentafluoropropoxy)phenyl]-2(1H,3H)-imidazolone, 0.43 g of 1-[(1R,2S)-2-(2,4-difluorophenyl)-2,3-epoxy-1-methylpropyl]-3-[4-(2,2,3,3,3-pentafluoropropoxy)phenyl]-2(1H,3H)-imidazolone was obtained as colorless plates.

$^1$H-NMR (CDCl$_3$) δ:1.36 (3H,d,J=7.2 Hz), 2.71 (1H,d,J=4.8 Hz), 2.81 (1H,d,J=4.8 Hz), 4.44 (2H,t,J=12 Hz), 5.08 (1H, q,J=7.2 Hz), 6.44 (1H,d,J=3.2 Hz), 6 52 (1H,d,J=3.2 Hz),6.78–6.95 (2H,m), 7.00 (2H,d,J=9.2 Hz), 7.35–7.48 (1H,m), 7.57 (2H, d, J =9.2 Hz).

REFERENCE EXAMPLE 45

In the same manner as in Reference Example 5, starting from 0.73 g of (1S)-1-[(2R)-(2,4-difluorophenyl)-2oxiranyl] ethanol and 0.75 g of 4-[4-(2,2,2-trifluoroethoxy)phenyl-3(2H,4H)-1,2,4-triazolone, 0.74 g of 2-[(1R,2S)-2-(2,4-difluorophenyl)-2,3-epoxy-1-methylpropyl]-4-[4-(2,2,2-trifluoroethoxy)phenyl]-3(2H,4H)-1,2,4-triazolone was obtained as a colorless oil.

$^1$H-NMR (CDCl$_3$) δ:1.46 (3H,d,J=7 Hz), 2.88 (1H,d,J=4.6 Hz), 3.15 (1H,d,J=4.6 Hz), 4.38 (2H,q,J=8 Hz), 4.94 (1H,q, J=7 Hz), 6.74–6.90 (2H, m), 7.02 (2H,d,J=9.2 Hz), 7.36–7.50 (1H,m), 7.44 (2H,d,J=9.2 Hz), 7.62 (1H,s).

REFERENCE EXAMPLE 46

In the same manner as in Reference Example 5, starting from 0.94 g of (1S)-1-[(2R)-(2,4-difluorophenyl)-2-oxiranyl]ethanol and 1.16 g of 4-[4-(2,2,3,3,3-pentafluoropropoxy)phenyl]-3(2H,4H)-1,2,4-triazolone, 0.68 g of 2-[(1R,2S)-2-(2,4-difluorophenyl)-2,3-epoxy-1-methylpropyl]-4-[4-(2,2,3,3,3-pentafluoropropoxy)phenyl]-3(2H,4H)-1,2,4-triazolone was obtained as a colorless oil.

$^1$H-NMR (CDCl$_3$) δ:1.46 (3H,d,J=7 Hz), 2.88 (1H,d,J=4.6 Hz), 3.15 (1H,d,J=4.6 Hz), 4.44 (2H,t,J=12 Hz), 4.94 (1H,q,J=7 Hz), 6.72–6.92 (2H,m), 7.02 (2H,dt,J=9.2 Hz, J=2.2 Hz), 7.30–7.50 (1H,m), 7.44 (2H,d,J=9.2 Hz, J=2.2 Hz), 7.62 (1H,s).

REFERENCE EXAMPLE 47

In the same manner as in Reference Example 5, starting from 0.70 g of (1S)-[(2R)-(2,4-difluorophenyl)-2-oxiranyl] ethanol and 1.17 g of 4-[4-(2,2,3,3,4,4,5,5-octafluoropentoxy)phenyl]-3(2H,4H)-1,2,4-triazolone, 0.18 g of 2-[(1R,2S)-2-(2,4-difluorophenyl)-2,3-epoxy-1-methylpropyl]-4-[4-(2,2,3,3,4,4,5,5-octafluoropropoxy)phenyl]-3(2H,4H)-1,2,4-triazolone was obtained as a colorless viscous oil.

$^1$H-NMR (CDCl$_3$) δ:1.47 (3H,d,J=7 Hz), 2.88 (1H,d,J=5 Hz), 3.16 (1H,d,J=5 Hz), 4.49 (2H,t,J=13 Hz), 4.95 (1H,q, J=7 Hz), 6.10 (1H,tt,J=52, 5.4 Hz), 6.75–6.90 (2H,m), 7.04 (2H,d,J=9.0 Hz), 7.25–7.42 (1H,m), 7.45 (2H,d,J=9.0 Hz), 7.62 (1H,s).

REFERENCE EXAMPLE 48

In the same manner as in Reference Example 5, starting from 0.971 g of (1S)-[(2R)-(2,4-difluorophenyl)-2-oxiranyl] ethanol and 1.0 g of 2-[4-(2,2,2-trifluoroethoxy) phenyl]-3(2H,4H)-1,2,4-triazolone, 0.825 g of 4-[(1R,2S)-2-(2,4-difluorophenyl)-2,3-epoxy-1-methylpropyl]-2-[4-(2,2,2-trifluoroethoxy)phenyl]-3(2H,4H)-1,2,4-triazolone was obtained as colorless prisms.

m.p. 118°–119 ° C.

$^1$H-NMR (CDCl$_3$) δ:1.42 (3H,d,J=7.2 Hz), 2.73 (1H,d,J=4.2 Hz), 2.77 (1H,d,J=4.2 Hz), 4.37 (2H,q,J=8.2 Hz), 5.00 (1H,q,J=7.2 Hz), 6.81–7.02 (2H,m),7.00 (2H,d,J=9.2 Hz), 7.31–7.50 (1H,m), 7.59 (1H,s), 7.93 (2H,d,J=9.2 Hz).

REFERENCE EXAMPLE 49

In the same manner as in Reference Example 5, starting from 0.98 g of (1S)-[(2R)-(2,4-difluorophenyl)-2-oxiranyl] ethanol and 1.04 g of 2-[4-(2,2,3,3,3-pentafluoropropoxy)phenyl]-3(2H,4H)-1,2,4-triazolone, 0.882 g of 4-[(1R,2S)-2-(2,4-difluorophenyl)-2,3-epoxy-1-methylpropyl]-2-[4-(2,2,3,3,3-pentafluoropropoxy)phenyl]-3(2H,4H)-1,2,4-triazolone was obtained as colorless prisms.

m.p. 128°–129 ° C.

$^1$H-NMR (CDCl$_3$) δ:1.43 (3H,d,J=7.2 Hz), 2.73 (1H,d,J=4.2 Hz), 2.77 (1H,d,J=4.2 Hz), 4.44 (2H,t,J=12.2 Hz), 5.01 (1H,q,J=7.2 Hz), 6.80–7.01 (2H,m), 7.01 (2H,d,J=9.2 Hz), 7.32–7.49 (1H,m), 7.59 (1H,s), 7.94 (2H,d,J=9.2 Hz).

REFERENCE EXAMPLE 50

In the same manner as in Reference Example 5, starting from 345 mg of (1S)-[(2R)-(2,4-difluorophenyl)-2-oxiranyl] ethanol and 410 mg of 2-[4-(2,2,3,3,4,4,5,5-octafluoropentoxy)phenyl]-3(2H,4H)-1,2,4-triazolone, 371 mg of 4-[(1R,2S)-2-(2,4-difluorophenyl)-2,3-epoxy-1-methylpropyl]-2-[4-(2,2,3,3,4,4,5,5-octafluoropentoxy)phenyl]-3(2H,4H)-1,2,4-triazolone was obtained as colorless prisms.

$^1$H-NMR (CDCl$_3$) δ:1.42 (3H,d,J=7 Hz), 2.73 (1H,d,J=4.2 Hz), 2.77 (1H,d,J=4.2 Hz), 4.49 (2H,t,J=13 Hz), 5.00 (1H,d,J=7 Hz), 6.12 (1H,tt,J=52, 5.4 Hz), 6.80–7.01 (2H,m), 7.01 (2H,d,J=9.2 Hz), 7.30–7.50 (1H,m), 7.59 (1H,s), 7.94 (2H,d,J=9.2 Hz).

REFERENCE EXAMPLE 51

In the same manner as in Reference Example 5, starting from 0.975 g of (1S)-[(2R)-(2,4-difluorophenyl)-2-oxiranyl] ethanol and 1.13 g of 2-[4-(2,2,3,3-tetrafluoropropoxy)phenyl]-3(2H,4H)-1,2,4-triazolone, 0.847 g of 4-[(1R,2S)-2-(2,4-difluorophenyl)-2,3-epoxy-1-methylpropyl]-2-[4-(2,2,3,3-tetrafluoropropoxy)phenyl]-3(2H, 4H)-1,2,4-triazolone was obtained as colorless prisms.

m.p. 116°–117 ° C.

$^1$H-NMR (CDCl$_3$) δ:1.42 (3H,d,J=7.2 Hz), 2.73 (1H,d,J=4.2 Hz), 2.77 (1H,d,J=4.2 Hz), 4.37 (2H,tt,J=11.8, 1.6 Hz), 5.00 (1H,q,J=7.2 Hz), 6.08 (1H,tt,J=53, 5 Hz), 6.79–7.04 (2H,m), 6.99 (2H,d,J=9.4 Hz), 7.32–7.49 (1H,m), 7.59 (1H, s), 7.93 (2H,d,J=9.4 Hz)

REFERENCE EXAMPLE 52

In the same manner as in Reference Example 5, starting from 1.15 g of (1S)-[(2R)-(2,4-difluorophenyl)-2-oxiranyl] ethanol and 1.27 g of 2-[4-(1,1,2,2-tetrafluoroethoxy)phenyl]-3(2H,4H)-1,2,4-triazolone, 1.20 g of 4-[(1R,2S)-2-(2,4-difluorophenyl)-2,3-epoxy-1-methylpropyl]-2-[4-(1,1,2,2-tetrafluoroethoxy)phenyl]-3(2H,4H)-1,2,4-triazolone was obtained as colorless needles.

m.p. 105°–106 °C.

$^1$H-NMR (CDCl$_3$) δ:1.43 (3H,d,J=7.2 Hz), 2.74 (1H,d,J=4.4 Hz), 2.77 (1H,d,J=4.4 Hz), 5.01 (1H,q,J=7.2 Hz), 5.92 (1H,tt,J=53, 2.8 Hz), 6.81–7.01 (2H,m), 7.28 (2H,d,J=9.2 Hz), 7.30–7.49 (1H,m), 7.61 (1H,s), 8.04 (2H,d,J=9.2 Hz).

REFERENCE EXAMPLE 53

2,4-difluoroaniline (25g) and 25.2 g of pyridine were dissolved in 200 ml of dichloromethane to which was added dropwise 33.3 g of phenyl chloroformate with ice cooling. After stirring for 30 minutes with ice cooling, the reaction solution was washed with water and dried followed by distilling the solvent to give a mixture of phenyl 2,4-difluorophenylcarbamate and pyridine. To the mixture was added 30.7 g of 2-(di-ethoxy)ethylamine and the mixture was stirred at room temperature. The crystals separated out were filtered and washed with petroleum ether to give 37.8 g of N-(2,2-diethoxyethyl)-N'-(2,4-difluorophenyl)urea as colorless crystals.

This urea (37.5 g) was dissolved in a mixture of 560 ml of methanol and 280 ml of water, and 300 ml of 0.48M hydrochloric acid was added thereto and the resulting mixture was stirred for three days at room temperature. The reaction solution was concentrated under reduced pressure. The crystals thus separated out were washed with a mixture of water and methanol (5:1) to give 22.8 g of 1-(2,4-difluorophenyl)-2(1H,3H)-imidazolone as a colorless powder.

m.p. 192°–194 °C.

Elemental analysis for C$_9$H$_6$F$_2$N$_2$O Calcd: C 55.11, H, 3.08, N, 14.28 Found: C 55.14, H, 3.29, N, 14.18

REFERENCE EXAMPLE 54–63

Imidazolone derivates shown in the following tables 1 and 2 were obtained in the same manner as in Reference Example 53.

TABLE 1

| Reference Example | —R | m.p. (°C.) |
|---|---|---|
| 54 | —C$_6$H$_4$—OCH$_3$ | 155–157 |
| 55 | —C$_6$H$_4$—OCF$_3$ | 145–146 |
| 56 | —C$_6$H$_4$—CH(CH$_3$)$_2$ | 167–168 |
| 57 | —C$_6$H$_4$—OCH$_2$CF$_2$CF$_2$H | 157–159 |
| 58 | —C$_6$H$_4$—OCH$_2$CF$_3$ | 145–151 |
| 59 | —C$_6$H$_4$—OCH$_2$CF$_2$CF$_3$ | 147–150 |

TABLE 2

| Reference Example | —R | m.p. (°C.) |
|---|---|---|
| 60 | —C$_6$H$_4$—OCH$_2$(CF$_2$)$_4$H | 127–128 |
| 61 | —C$_6$H$_4$—Cl | 176–178 |
| 62 | —C$_6$H$_4$—OCF$_2$CF$_2$H | 161–163 |

TABLE 2-continued

| Reference Example | —R | m.p. (°C.) |
|---|---|---|
| 63 | —C₆H₄—N(piperazine)N—C₆H₄—OCH₂CF₂CF₂H | >300 |

REFERENCE EXAMPLE 64

To aminoacetoaldehyde diethylacetal (7.8 ml, 53.6 mmol) was added dropwise 10 g (53.4 mmol) of 4-trifluoromethylphenylisocyanate at 0° C. during five minutes. The reaction solution was stirred for one hour at room temperature. The crystals thus produced was collected by filtration and washed with hexane to give 16.2 g of 1-(2,2-diethoxyethyl)-3-(4-trifluoromethylphenyl)urea (95%) as a colorless powder.

1-(2,2-Diethoxyethyl)-3-(4-trifluoromethylphenyl)urea (9.2 g, 28.7 mmol) was dissolved in a mixture of 113 ml of methanol and 57 ml of water. To the reaction solution was added 67.5 ml of 0.48N hydrochloric acid and the mixture was stirred for 48 hours at room temperature. To the reaction solution was added 1N sodium hydroxide to adjust pH to 7, followed by being concentrated under reduced pressure. The residue was extracted with ethyl acetate (100 ml×4). The extracts were combined, washed with water and saturated aqueous solution of sodium chloride successively, dried over magnesium sulfate and distilled off. The crystals thus separated out were recrystallized from ethyl acetate-isopropylether to give 4.87 g of 1-(4-trifluoromethylphenyl)-2(1H, 3H)-imidazolone (74%) as colorless prisms.

m.p. 170°–171° C.

REFERENCE EXAMPLE 65

4-Trifluoromethoxyaniline (20 g) and 9.8 g of pyridine were dissolved in 150 ml of ethyl acetate, and 19.5 g of phenyl chloroformate was added thereto with ice cooling. After stirring for 15 minutes with ice cooling, the reaction solution was washed with water, dried and distilled off under reduced pressure. The crystals separated out were washed with hexane to give 34.1 g of phenyl 4-trifluoromethoxycarbamate as colorless crystals.

This carbamate (15.0 g) and 6 ml of hydrazine hydrate were stirred in 50 ml of ethanol for 2 hours. The reaction solution was concentrated under reduced pressure and the residue was washed with cold ethyl acetate to give 11.7 g of 4-(4-trifluoromethoxyphenyl)semicarbazide as colorless crystals.

After stirring 7.0 g of this semicarbazide and 15.5 g of formamidine acetate in 150 ml of dimethyl formamide at room temperature for 30 minutes, 8.9 g of acetic acid was added and the mixture was heated for 6 hours at 80° C. The solvent was distilled off under reduced pressure. To the residue were added ethyl acetate and saturated aqueous solution of sodium chloride. The organic layer was dried and concentrated, and the residue was recrystallized from ethyl acetate-hexane to give 3.44 g of 4-(4-tifluoromethoxyphenyl)-3(2H,4H)-1,2,4-triazolone as colorless crystals.

m.p. 193°–195° C.

$^1$H-NMR(CDCl₃)δ:7.37 (2H,d,J=9 Hz), 7.63 (2H,dt,J=9 Hz, J=2 Hz), 7.73 (1H,d,J=1.4 Hz), 10.23 (1H,br)

REFERENCE EXAMPLES 66–84

In the same manner as in Reference Example 65, triazolone derivatives shown in the following tables 3 to 5 were obtained.

TABLE 3

| Reference Example | —R | m.p. (°C.) |
|---|---|---|
| 66 | —C₆H₄—F | 214 |
| 67 | —C₆H₄—OCH₃ | 195–196 |
| 68 | —C₆H₄—CF₃ | 225–226 |

TABLE 3-continued
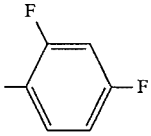
| Reference Example | —R | m.p. (°C.) |
|---|---|---|
| 69 | 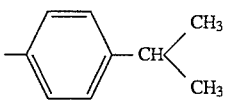 | 149–150 |
| 70 | 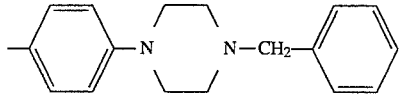 | 191–192 |
| 71 | 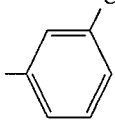 | 255–256 |
TABLE 4
| Reference Example | —R | m.p. (°C.) |
|---|---|---|
| 72 | 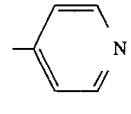 | 151–152 |
| 73 | 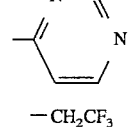 | 278 |
| 74 | 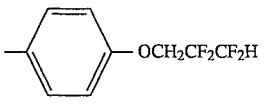 | 234–235 |
| 75 | —CH$_2$CF$_3$ | 100–104 |
TABLE 4-continued
| Reference Example | —R | m.p. (°C.) |
|---|---|---|
| 76 | 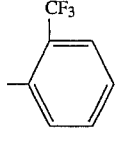 | 163–165 |
| 77 | 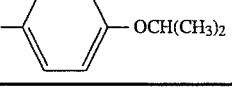 | 178–180 |
| 78 | 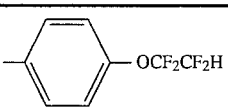 | 208–209 |
TABLE 5
| Reference Example | —R | m.p. (°C.) |
|---|---|---|
| 79 | 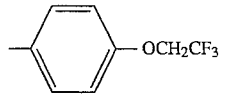 | 216–217 |
| 80 | —⟨C$_6$H$_4$⟩—OCH$_2$CF$_3$ | 177–178 |

TABLE 5-continued

| Reference Example | —R | m.p. (°C.) |
|---|---|---|
| 81 | 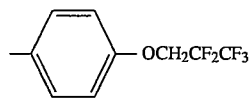 —⟨phenyl⟩—OCH₂CF₂CF₃ | 187–188 |
| 82 | 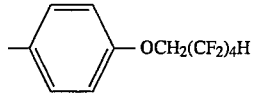 —⟨phenyl⟩—OCH₂(CF₂)₄H | 153–155 |
| 83 |  —⟨phenyl⟩—Cl | 200–201 |
| 84 | 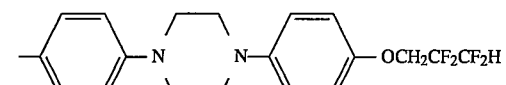 —⟨phenyl⟩—N(piperazine)N—⟨phenyl⟩—OCH₂CF₂CF₂H | 267–269 |

REFERENCE EXAMPLE 85

To a solution of 3-methylbutylamine (20 g, 229 mmol) in 840 ml of dichloromethane were added 35.6 ml triethylamine (255 mmol) and 28.8 ml of phenyl chloroformate (230 mmol) at 0° C. The mixture was stirred for three hours at room temperature. After distilling off the solvent under reduced pressure, 200 ml of ethyl acetate and 200 ml of water were added to the residue. The organic layers were separated and water layer was extracted with ethyl acetate (100 ml×3). The organic layers were combined, washed with water and saturated sodium chloride solution successively and dried over magnesium sulfate. The solvent was distilled off and the crystals separated out were collected by filtration, and washed with petroleum ether to give 39.5 g of phenyl 3-methylbutylcarbamate (83%) as colorless crystals.

To a solution of phenyl 3-methylbutylcarbamate (18.5 g, 8.9 mmol) in 210 ml of dioxane was added 22 ml of hydrazinehydrate, and the mixture was heated under reflux for three hours. After cooling, the solvent was distilled off under reduced pressure. The residue was dissolved in 200 ml of ethyl acetate. To the solution was added 4N hydrogen chloride-ethyl acetate solution (22 ml) and the mixture was stirred for one hour at room temperature. The precipitates were collected by filtration, washed with ethyl acetate (50 ml×2) and dried to give 14.8 g of 4-(3-methylbutyl) semicarbazide hydrochloride (91%) as a white powder.

A mixture of 13.0 g of 4-(3-methylbutyl)semicarbazidehydrochloride (71.6 mmol) and 60 ml of ethyl orthoformate was stirred at 110° C. for two hours. After cooling, the mixture was subjected to column chromatography using silica-gel (eluate; ethyl acetate:hexane=1:2 to 2:1 to ethyl acetate to ethyl acetate:methanol=10:1). The desired fraction was concentrated. The crystals thus given was recrystallized from ethyl acetate-petroleum ether to give 7.0g of 4-(3-methylbutyl)-3(2H,4H)-1,2,4-triazolone (63%) as colorless needles.

m.p. 78°–79° C.

$^1$H-NMR (CDCl$_3$) δ: 0.96 (6H,d,J=6.4 Hz), 1.53–1.72 (3H,m), 3.66 (2H,t,J=7.4 Hz), 7.39 (1H,s) Elemental analysis for C$_7$H$_{13}$N$_3$O Calcd; C,54.17; H,8.44; N,27.07 Found; C,54.14: H,8.47; N, 27.14

REFERENCE EXAMPLE 86

To a mixture of 5.0 g of 4-(trifluoromethyl)phenylhydrazine (28.4 mmol), 31 ml of water and 3.1 ml of concentrated hydrochloric acid was added 2.9 g of glyoxylic acid-hydrate (31.4 mmol), and the mixture was stirred for one hour at room temperature. The precipitates thus separated out was collected by filtration, washed with water and dried over phosphorus pentoxide to give 6.26 g of 4-(trifluoromethyl)phenylhydrazonoacetic acid (95%) as a pale yellow powder.

4-(trifluoromethyl)phenylhydrazonoacetic acid (6.26 g, 27 mmol) was suspended in 176 ml of toluene, and 4.0 ml of triethylamine (28.7 mmol) and 6.1 ml of diphenylphosphorylazide (28.3 mmol) were added and the resulting mixture was stirred for one hour at 120° C. After cooling, the reaction solution was extracted with 200 ml of an aqueous solution of pottasium hydroxide (10%). The aqueous extract was acidified with concentrated hydrochloric acid to adjust pH to 1, and the crystals thus separated out were washed with water and hexane successively and dried over phosphorus pentoxide to give 4.48 g of 2-(4-trifluoromethylphenyl)-3(2H,4H)-1,2,4-triazolone (72%) as a colorless powder.

m.p. 221° C.

REFERENCE EXAMPLES 87–94

In the same manner as in Reference Example 86, triazolone derivatives shown in the following table 6 were obtained.

TABLE 6

| Reference Example | —R | m.p. (°C.) |
|---|---|---|
| 87 | 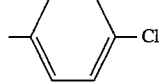 | 206 |
| 88 | 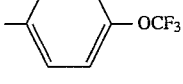 | 258–260 |
| 89 | 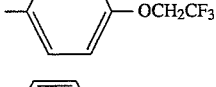 | 174–175 |
| 90 | 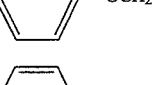 | 179–180 |
| 91 | 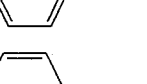 | 180–181 |
| 92 | 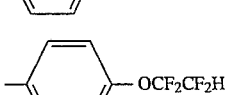 | 161–162 |
| 93 | 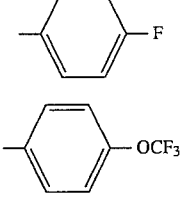 | 186–187 |
| 94 | 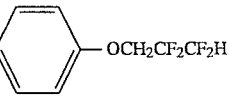 | 192–193 |

REFERENCE EXAMPLE 95

In the same manner as in Reference Example 64, 1-(4-fluorophenyl)-2(1H,3H)-imidazolone was obtained.

m.p. 166°–167° C.

REFERENCE EXAMPLE 96

To 4-trifluoromethylphenyl isocyanate (2.89 ml, 20.2. mmol) was added 5.36 ml of azidotrimethylsilane (39.9 mmol), and the mixture was stirred at 110° C. for twenty-four hours. After cooling, the mixture was subjected to column chromatography using silicagel (eluate; ethyl acetate:hexane=1;1 to 2:1 to ethyl acetate) to collect a desired fraction to be concentrated. The crystals obtained were recrystallized from ethyl acetate-hexane to give 3.64 g of 1-(4-trifluoromethylphenyl)-5(1H,4H)-tetrazolone (78%) as colorless needles.

m.p. 191°–192° C.

REFERENCE EXAMPLES 97–104

In the same manner as in Reference Example 96, tetrazolone derivatives shown in the following table 7 were obtained.

TABLE 7

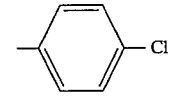

| Reference Example | —R | m.p. (°C.) |
|---|---|---|
| 97 | 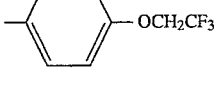 | 195–196 |
| 98 | 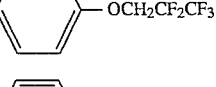 | 152–153 |
| 99 | 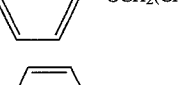 | 156–157 |
| 100 | 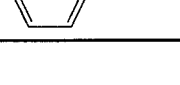 | 207–208 |
| 101 |  | 148–151 |
| 102 |  | 151–152 |
| 103 |  | 129–130 |
| 104 |  | 164–165 |

REFERENCE EXAMPLE 105

4-[4-(1,1,2,2-Tetrafluoroethoxy)phenyl]semicarbazide (6.0 g) and 10.6 g of acetamidine hydrochloride were dissolved in 100 ml of dimethylformamide. The solution was stirred for one hour at room temperature. After adding 6.6 g of acetic acid, the reaction solution was heated at 80° C. for seven hours and concentrated under reduced pressure. The residue was dissolved in a mixture of 200 ml of ethyl acetate and 40 ml of water. The separated organic layer was washed with water and saturated sodium chloride solution, dried and distilled off to remove the solvent. The residue was recrystallized from ethyl acetate to give 3.6 g of 5-methyl-4-[4-(1,1,2,2-tetrafluoroethoxy)phenyl]-3(2H,4H)-1,2,4-triazolone as colorless needles.

m.p. 204°–205° C.

$^1$H-NMR (DMSO-$d_6$) δ: 2.08 (3H,s), 6.84 (1H,tt,J=51.8 Hz,J=3.2 Hz), 7.43 (2H,d,J=8.8 Hz), 7.55 (2H,d,J=8.8 Hz), 11.57 (1H,s)

REFERENCE EXAMPLE 106

In the same manner as in Reference Example 105, 5-methyl-4-[4-(2,2,3,3-tetrafluoropropoxy)phenyl]-3(2H,4H)-1,2,4-triazolone was obtained.

m.p. 206°–207° C.

REFERENCE EXAMPLE 107

4-Chlorophenylhydrazine hydrochloride (5.0 g) and 3.4 g of sodium acetate were dissolved in a mixture of 50 ml of water and 25 ml of ethanol, to which 1.69 g of 80% acetaldhyde aqueous solution were added dropwise at room temperature, and the resulting mixture was stirred for 30 minutes at room temperature. After adding 50 ml of water, the reaction mixture was extracted with ethyl acetate. The organic layer was washed with water and saturated sodium chloride solution, dried and distilled off to give acetaldehyde 4-chlorophenylhydrazone as an oil.

This hydrazone was dissolved in 15 ml of acetic acid, to which an aguenous suspension of 1.82 g of sodium cyanate were added, and the mixture was stirred for one hour at room temperature. The separated crystals were collected by filtration and washed with water to give 4.8 g of 2-(4-chlorophenyl)-5-methyl-1,2,4-triazolizin-3-one as a reddish brown powder.

A mixture of 1.0 g of 2-(4-chlorophenyl)-5-methyl-1,2,4-triazolizin-3-one, 50% aqueous solution of 2.28 g of sodium hydroxide and 0.11 g of tributylammonium bromide in 25 ml of toluene was stirred for four hours at 60° C. After cooling, the reaction mixture was diluted with 25 ml of water. The separated aqueous layer was acidified with concentrated hydrochloric acid. The separated crystals were collected by filtration and recrystallized from ethyl acetate-diisopropyl ether to give 0.56 g of 2-(4-chlorophenyl)-5-methyl-3(2H,4H)-1,2,4-triazolone as colorless needles.

m.p. 218°–219° C.

$^1$H-NMR (CDCl$_3$) δ: 2.34 (3H,s), 7.40 (2H, tt,J=2.2 Hz, J=2.2 Hz), 7.91 (2H,tt,J=9.2 Hz,J=2.2 Hz), 11.65 (1H,br)

REFERENCE EXAMPLE 108

In the same manner as in Reference Example 107, 5-methyl-2-(4-trifluoromethoxyphenyl)-3(2H,4H)-1,2,4-triazolone was obtained.

m.p. 213°–214° C.

REFERENCE EXAMPLE 109

In the same manner as in Reference Example 5, starting from 0.44 g of (1S)-1-[(2R)-(2,4-difluorophenyl)-2-oxiranyl]ethanol and 0.48 g of 1-[4-[4-[4-(2,2,3,3-tetrafluoropropoxy)phenyl]-1-piperazinyl]phenyl]-2(1H,3H)imidazolone, 0.11 g of 1-[(1R,2S)-2-(2,4-difluorophenyl)-2,3-epoxy-1-methylpropyl]-3-[4-[4-[4-(2,2,3,3-tetrafluoropropoxy)phenyl]-1-piperazinyl]phenyl]-2(1H,3H)-imidazolone was obtained as a colorless powder.

$^1$H-NMR (CDCl$_3$) δ: 1.36 (3H,d,J=7.2 Hz), 2.70 (1H,d, J=4.8 Hz), 2.81 (1H,d,J=4.8 Hz), 3.22–3.40 (8H, m), 4.31 (2H,t,J=12 Hz), 5.07 (1H,q,J=7.2 Hz), 6.07 (1H,tt,J=53, 5.2 Hz), 6.40 (1H,d,J=3.2 Hz), 6.50 (1H,d,J=3.2 Hz), 6.70–7.03 (8H,m), 7.22–7.51 (3H,m).

REFERENCE EXAMPLE 110

In the same manner as in Reference Example 5, starting from 0.31 g of (1S)-1-[(2R)-(2,4-difluorophenyl)-2-oxiranyl]ethanol and 0.50 g of 4-[4-[4-[4-(2,2,3,3-tetrafluoropropoxy)phenyl]-1-piperazinyl]phenyl]-3(2H,4H)-1,2,4-triazolone, 0.15 g of 2-[(1R,2S)-2-(2,4-difluorophenyl)-2,3-epoxy-1-methylpropyl]-4-[4-[4-[4-(2,2,3,3-tetrafluoropropoxy)phenyl]-1-piperazinyl]phenyl]-3(2H, 4H)-1,2,4-triazolone was obtained as a colorless powder.

$^1$H-NMR (CDCl$_3$) δ:1.46 (3H,d,J=7.0 Hz), 2.88 (1H,d, J=5 Hz), 3.16 (1H,d,J=5 Hz), 3.22–3.39 (8H,m), 4.31 (2H, t,J=12.2 Hz), 4.96 (1H,q,J=7.0 Hz), 6.07 (1H,tt,J=53, 5.0 Hz), 6.75–7.03 (8H,m), 7.23–7.40 (3H,m), 7.59 (1H,s).

REFERENCE EXAMPLE 111

In the same manner as in Reference Example 5, starting from 0.35 g of (1S)-1-[(2R)-(2,4-difluorophenyl)-2-oxiranyl]ethanol and 0.31 g of 1-[4-(2,2,2-trifluoroethoxy)phenyl]-5(1H,4H)-tetrazolone, a mixture (3:2, 0.22 g) of 1-[(1R,2S)-2-(2,4-difluorophenyl)-2,3-epoxy-1-methylpropyl]-4-[4-(2,2,2-trifluoroethoxy)phenyl]-5(1H,4H)-tetrazolone and (2R)-2-(2,4-difluorophenyl)-2-[(1R)-1-[1-[4-(2,2,2-trifluoroethoxy)phenyl]-1H-tetrazol-5-yloxy]ethyl]oxirane was obtained as a colorless oil.

$^1$H-NMR (CDCl$_3$) δ: 1.55 (d,J=7 Hz), 1.60 (d,J=8 Hz), 2.93 (d,J=4.5 Hz), 2.96 (d,J=4.8 Hz), 3.17 (d,J=4.5 Hz), 3.20 (d,J=4.8 Hz), 4.40 (q,J=8 Hz), 4.44 (q,J=8 Hz), 4.93 (g,J=8 Hz), 5.31 (q,J=7 Hz), 6.77–6.95 (m), 7.06 (d,J=9.2 Hz), 7.09 (d,J=9.2 Hz), 7.27–7.45 (m), 7.61 (d,J=9.2 Hz), 7.86 (d,J=9.2 Hz).

REFERENCE EXAMPLE 112

In the same manner as in Reference Example 5, starting from 1.049 g of (1S)-1-[(2R)-(2,4-difluorophenyl)-2-oxiranyl]ethanol and 1.17 g of 1-[4-(1,1,2,2-tetrafluoroethoxy)phenyl]- 5(1H,4H)-tetrazolone, 1.28 g of 1-[(1R, 2S)-2-(2,4-difluorophenyl)-2,3-epoxy-1-methylpropyl ]-4-[4-(1,1,2,2-tetrafluoroethoxy)phenyl]-5(1H,4H)-tetrazolone was obtained as a colorless oil.

$^1$H-NMR (CDCl$_3$) δ:1.61 (3H,d,J=7 Hz), 2.93 (1H,d,J= 4.4 Hz), 3.17 (1H,d,J=4.4 Hz), 4.93 (1H,q,J=7 Hz), 5.94 (1H,tt,J=52.8, 2.6 Hz), 6.75–6.94 (2H,m), 7.24–7.40 (1H, m), 7.34 (2H,d,J=9 Hz), 7.98 (2H,d,J=9 Hz).

IRγ$_{max}^{neat}$ cm$^{-1}$: 3060, 1734, 1618, 1599, 1510, 1427.

REFERENCE EXAMPLE 113

In the same manner as in Reference Example 5, starting from 0.962 g of (1S)-1-[(2R)-(2,4-difluorophenyl)-2-oxiranyl]ethanol and 1.19 g of 1-[4-(2,2,3,3,3-pentafluoropropoxy)phenyl]-5(1H,4H)-tetrazolone, 1.31 g of 1-[(1R,2S)-2-(2,4-difluorophenyl)-2,3-epoxy-1-methylpropyl]-4-[4-(2,2,3,3,3-pentafluoropropoxy)phenyl]-5(1H,4H)-tetrazolone was obtained as a colorless oil.

$^1$H-NMR (CDCl$_3$) δ: 1.60 (3H,d,J=7 Hz), 2.92 (1H,d,J= 4.4 Hz), 3.16 (1H,d,J=4.4 Hz), 4.46 (2H,dt,J=12, 1 Hz), 4.92 (1H,q,J=7 Hz), 6.75–6.93 (2H,m), 7.05 (2H,d,J=9.2 Hz), 7.20–7.38 (1H,m), 7.86 (2H,d,J=7 Hz).

IRδ$_{max}^{neat}$cm$^{-1}$: 3060, 1732, 1618, 1601, 1558, 1516, 1427.

REFERENCE EXAMPLE 114

In the same manner as in Reference Example 5, starting from 0.988 g of (1S)-[(2R)-(2,4-difluorophenyl)-2-oxiranyl] ethanol and 1.55 g of 1-[4-(2,2,3,3,4,4,5,5-octafluoropenthoxy)phenyl]-5(1H,4H)-tetrazolone, a mixture 7:3, 1.72 g) of 1-[(1R,2S)-2-(2,4-difluorophenyl)-2,3-epoxy-1-methylpropyl]-4-[4-(2,2,3,3,4,4,5,5-octafluoropenthoxy) phenyl]

-5(1H,4H)-tetrazolone and (2R)-2-(2,4-difluorophenyl)-2-[(1R)-1-[1-[4-(2,2,3,3,4,4,5,5-octafluoropenthoxy)phenyl]-1H-tetrazol-5-yloxy]ethyl]oxirane was obtained as a colorless oil.

$^1$H-NMR (CDCl$_3$) δ: 1.55 (dd,J=6.6, 1.5 Hz), 1.60 (d,J=7.2 Hz), 2.93 (d,J=4.5 Hz), 2.95 (d,J=4.8 Hz), 3.17 (d,J=4.5 Hz), 3.20 (d,J=4.8 Hz), 4.51 (t,J=12.9 Hz), 4.55 (t,J=12.8 Hz), 4.93 (q,J=7.2 Hz), 5.31 (q,J=7.2 Hz), 6.10 (tt,J=52, 5.5 Hz), 6.11 (tt,J=52, 5.3 Hz), 6.74–6.94 (m), 7.06 (d,J=9 Hz), 7.09 (d,J=9 Hz), 7.28–7.45 (m), 7.61 (d,J=9 Hz), 7.86 (d,J=9 Hz).

REFERENCE EXAMPLE 115

In the same manner as in Reference Example 5, starting from 0.50 g of (1S)-L-[(2R)-(2,4-difluorophenyl)-2-oxiranyl]ethanol and 0.61 g of 5-methyl-4-[4-(2,2,3,3-tetrafluoropropoxy)phenyl]-3(2H,4H)-1,2,4-triazolone, 0.45 g of 2-[(1R,2S)-2-(2,4-difluorophenyl)-2,3-epoxy-1-methylpropyl]-5-methyl-4-[4-(2,2,3,3-tetrafluoropropoxy)phenyl]-3(2H,4H)-1,2,4-triazolone was obtained as a colorless oil.

$^1$H-NMR (CDCl$_3$) δ:1.44 (3H,d,J=7.2 Hz), 2.11 (3H,s), 2.87 (1H,d,J=4.8 Hz), 3.17 (1H,d,J=4.8 Hz), 4.38 (2H,t,J=11.8 Hz), 4.94 (1H,q,J=7.2 Hz), 5.06 (1H,tt,J=53 Hz,J=4.7 Hz), 6.74–6.90 (2H,m), 7.02 (2H,dt,J=9.2 Hz,J=2.6 Hz), 7.18 (2H,dt,J=9.2 Hz,J=2.6 Hz), 7.28–7.43 (1H,m).

REFERENCE EXAMPLE 116

In the same manner as in Reference Example 5, starting from 0.50 g of (1S)-1-[(2R)-(2,4-difluorophenyl)-2-oxiranyl]ethanol and 0.58 g of 5-methyl-4-[4-(1,1,2,2-tetrafluoroethoxy)phenyl]-3(2H,4H)-1,2,4-triazolone, 0.46 g of 2-[(1R,2S)-2-(2,4-difluorophenyl)-2,3-epoxy-1-methylpropyl]-5-methyl-4-[4-(1,1,2,2-tetrafluoroethoxy)phenyl]-3(2H,4H)-1,2,4-triazolone was obtained as a colorless oil.

$^1$H-NMR (CDCl$_3$) δ: 1.45 (3H,d,J=7 Hz), 2.15 (3H,s), 2.87 (1H,d,J=4.6 Hz), 3.18 (1H,d,J=4.6 Hz), 4.94 (1H,q,J=7 Hz), 5.94 (1H,tt,J=53 Hz,J=2.6 Hz), 6.74–6.90 (2H,m), 7.25–7.42 (5H,m).

REFERENCE EXAMPLE 117

In the same manner as in Reference Example 5, starting from 0.70 g of (1S)-1-[(2R)-(2,4-difluorophenyl)-2-oxiranyl]ethanol and 0.62 g of 2-(4-chlorophenyl)-5-methyl-3(2H,4H)-1,2,4-triazolone, 0.28 g of 2-(4-chlorophenyl)-4-[(1R,2S)-2-(2,4-difluorophenyl)-2,3-epoxy-1-methylpropyl]-3(2H,4H)-1,2,4-triazolone was obtained as a colorless oil.

$^1$H-NMR (CDCl$_3$) δ: 1.55 (3H,d,J=7.2 Hz), 2.24 (3H,s), 2.94 (1H,d,J=4.2 Hz), 3.16 (1H,d,J=4.2 Hz), 4.81 (1H,q, J=7.2 Hz), 6.78–6.93 (2H,m), 7.30–7.46 (1H,m), 7.36 (2H, d,J=9 Hz), 7.90 (2H,d,J=9 Hz).

REFERENCE EXAMPLE 118

In the same manner as in Reference Example 5, starting from 0.50 g of (1S)-1-[(2R)-(2,4-difluorophenyl)-2-oxiranyl] ethanol and 0.52 g of 5-methyl-2-(4-trifluoromethoxyphenyl)-3(2H,4H)-1,2,4-triazolone, 0.13 g of 4-[(1R,2S)-2-(2,4-difluorophenyl)-2,3-epoxy-1-methylpropyl]-5-methyl-2-(4-trifluoromethoxyphenyl)-3(2H,4H)-1,2,4-triazolone was obtained as a colorless viscous oil.

$^1$H-NMR (CDCl$_3$) δ: 1.55 (3H,d,J=7 Hz), 2.24 (3H,s), 2.92 (1H,d,J=4 Hz), 3.16 (1H,d,J=4 Hz), 4.81 (1H,q,J=7 Hz), 6.78–6.91 (2H,m), 7.25 (2H,d,J=9 Hz), 7.33–7.44 (1H, m), 7.97 (2H,d,J=9 Hz).

WORKING EXAMPLE 1

A mixture of 300 mg of (2R,3S)-2-(2,4-difluorophenyl)-3-methyl-2-[(1H-1,2,4-triazol-1-yl)methyl]oxirane and 2.77 g of 1-phenyl-2-trimethylsilyloxyimidazole was stirred in an argon atmosphere at 180° C. for 4 hours. After cooling, 50 ml of chloroform and 50 ml of water were added to the reaction solution. The separated aqueous layer was further extracted with 10 ml of chloroform. The organic extracts were combined, washed with water and with saturated aqueous solution of sodium chloride successively and dried over magnesium sulfate. The solvent was distilled off under reduced pressure and the residue was purified by silica gel chromatography (eluate; ethyl acetate:hexane=1:2 to 1:1) to give 16 mg of 1-[(1R,2R)-2-(2,4-difluorophenyl)-1-methyl-3-(1H-1,2,4-triazol-1-yl)-2-trimethylsilyloxypropyl]-3-phenyl-2(1H,3H)-imidazolone.

$^1$H-NMR (CDCl$_3$) δ: 0.28 (9H,s), 1.09 (3H,d,J=7 Hz), 4.35 (1H,d,J=15 Hz), 5.06 (1H,q,J=7 Hz), 5.28 (1H,dd,J=15, 2 Hz), 6.62 (1H, d,J=3.2 Hz), 6.71 (1H,d,J=3.2 Hz), 6.75–6.91 (2H,m), 7.25–7.65 (6H,m), 7.67 (1H,s), 7.89 (1H,s).

To a solution of 118 mg of the above compound in 6 ml of tetrahydrofuran was added 77 mg of tetrabutylammonium fluoride trihydrate and the mixture was stirred at room temperature for 30 minutes. The reaction solution was concentrated under reduced pressure. The residue was purified by silica gel chromatography (eluate; ethyl acetate:hexane=1:1 to 2:1) to give 83 mg of 1-[(1R,2R)-2-( 2,4-difluorophenyl)-2-hydroxy-1-methyl-3-(1H-1,2,4-triazol-1-yl)propyl]-3-phenyl-2(1H,3H)-imidazolone (Compound 1) as a white powder.

$^1$H-NMR (CDCl$_3$) δ: 1.21 (3H,d,J=7 Hz), 4.20 (1H,d,J=14.4 Hz), 4.95 (1H,q,J=7 Hz), 5.11 (1H,d,J=14.4 Hz), 5.64 (1H, s), 6.66 (1H,d,J=3.2 Hz), 6.73 (1H,d,J=3.2 Hz), 6.75–6.87 (2H, m), 7.40–7.69 (6H,m), 7.72 (1H,s), 7.86 (1H,s).

IRγ$_{max}^{KBr}$cm$^{-1}$: 1684, 1616, 1558, 1522, 1498, 1320.

SIMS (m/z): 412 (M+H)$^+$.

WORKING EXAMPLE 2

1-[(1R,2R)-2-(2,4-Difluorophenyl)-2-hydroxy-1-methyl-3-(1H-1,2,4-triazol-1-yl)propyl]-3-(4-trifluoromethylphenyl)-2(1H,3H)-imidazolone (Compound 2).

60% Sodium hydride in oil (65 mg) was dispersed in 4 ml of dimethylformamide, to which 118 mg of 1,2,4-triazole was added with ice cooling. The mixture was stirred at room temperature for 10 minutes. A solution of 362 mg of 1-[(1R,2S)-2-(2,4-difluorophenyl)-2,3-epoxy-1-methylpropyl]-3-(4-trifluoromethylphenyl)-2(1H,3H)-imidazolone prepared in Reference Example 5 in 2 ml of dimethylformamide was added and the resulting mixture was heated at 50° C. for 5 hours. After cooling, the reaction solution was fractionated after adding 8 ml of cold water and 40 ml of ethyl acetate and the separated aqueous layer was extracted with ethyl acetate twice. The ethyl acetate layers were combined, washed with water and saturated aqueous solution of sodium chloride successively, dried over magnesium sulfate and distilled off under reduced pressure. The residue was purified by silica gel chromatography (eluate; ethyl acetate:hexane=1:1 to 2:1 to ethyl acetate) to give 350 mg of the compound 2 as a white powder.

$^1$H-NMR (CDCl$_3$) δ: 1.21 (3H,d,J=7.2 Hz), 4.19 (1H,d, J=14.2 Hz), 5.00 (1H,q,J=7.2 Hz), 5. 11 (1H,d,J=14.2 Hz), 5.46 (1H, s), 6.71 (1H,d,J=3.2 Hz), 6.83 (1H,d,J=3.2 Hz), 6.72–6.90 (2H,m), 7.40–7.56 (1H,m), 7.72 (2H,d,J=8.4 Hz), 7.75 (1H,s), 7.83 (2H,d,J=8.4 Hz), 7.84 (1H,s).

IR$\gamma_{max}^{KBr}$ cm$^{-1}$: 3404, 3383, 3000, 1693, 1618, 1599, 1524, 1500, 1429, 1327.

Elemental analysis for $C_{22}H_{18}F_5N_5O_2$ Calcd: C 55.12, H 3.78, N 14.61 Found: C 54.81, H 3.97, N 14.39

WORKING EXAMPLE 3–19

The following compounds were obtained in accordance with the same manner as in working Example 2.

WORKING EXAMPLE 3

1-[(1R,2R)-2-(2,4-Difluorophenyl)-2-hydroxy-1-methyl-3-(1H-1,2,4-triazol-1-yl)propyl]-3-methyl-2(1H,3H)-imidazolone (Compound 3), colorless oil.

Yield: 88 mg (69%).

$^1$H-NMR (CDCl$_3$) δ: 1.19 (3H,d,J=6.8 Hz), 3.45 (3H,s), 4.69 (1H,d,J=14.4 Hz), 5.05 (1H,dd,J=14.4, 1.4 Hz), 5.34 (1H, q,J=6.8 Hz), 5.60 (1H,s), 6.55 (1H,d,J=1.6 Hz), 6.64 (1H,d,J=1.6 Hz), 6.70–6.88 (2H,m), 7.45–7.62 (1H,m), 7.70 (1H,s), 8.06 (1H,s).

IR$\gamma_{max}^{neat}$ cm$^{-1}$: 3113, 1660, 1618, 1597, 1535.

SIMS (m/z): 350 (M+H)$^+$

WORKING EXAMPLE 4

1-[(1R, 2R)-2-(2,4-Difluorophenyl)-2-hydroxy-1-methyl-3-(1H-1,2,4-triazol-1-yl)propyl ]-3-(4-fluorophenyl)-2(1H, 3H)-imidazolone (Compound 4), colorless powder.

Yield: 971 mg (74%).

$^1$H-NMR (CDCl$_3$) δ: 1.20 (3H,d,J=7 Hz), 4.20 (1H,d,J=14.2 Hz), 4.95 (1H,q,J=7 Hz), 5.10 (1H,d,J=14.2 Hz), 5.58 (1H, br), 6.60 (1H,d,J=3.2 Hz), 6.74 (1H,d,J=3.2 Hz), 6.70–6.88 (2H,m), 7.05–7.20 (2H,m), 7.40–7.65 (3H,m), 7.73 (1H,s), 7.85 (1H,s).

IR$\gamma_{max}^{KBr}$ cm$^{-1}$: 3147, 3126, 1687, 1618, 1599, 1513.

SIMS (m/z): 430 (M+H)$^+$ $[α]_D^{20}$ –24.8° (c=0.4, methanol)

WORKING EXAMPLE 5

1-[(1R,2R)-2-(2,4-Difluorophenyl)-2-hydroxy-1-methyl-(3-(1H-1,2,4-triazol-1-yl)propyl]-3-(2,4-difluorophenyl)-2-(1H,3H)-imidazolone (Compound 5) colorless powdery crystals.

Yield: 416 mg (66%), m.p. 134°–136° C.

$^1$H-NMR (CDCl$_3$) δ: 1.21 (3H,d,J=7 Hz), 4.19 (1H,d,J=14.4 Hz), 4.95 (1H,q,J=7 Hz), 5.11 (1H,d,J=14.4 Hz), 5.52 (1H, br), 6.52 (1H,t,J=2.6 Hz), 6.70–6.86 (3H,m), 6.92–7.06 (2H,m), 7.40–7.68 (2H,m), 7.74 (1H,s), 7.85 (1H,s).

IR$\gamma_{max}^{KBr}$ cm$^{-1}$: 1693, 1614, 1515, 1428, 1269, 1248.

WORKING EXAMPLE 6

2-[(1R, 2R)-2-(2,4-Difluorophenyl)-2-hydroxy-1-methyl-3-(1H-1,2,4-triazol-1-yl)propyl]-4-(4-fluorophenyl)-3(2H, 4H)-triazolone (Compound 6), colorless powder.

Yield: 532 mg (53%).

$^1$H-NMR (CDCl$_3$) δ:1.30 (3H,d,J=7 Hz), 4.36 (1H,d,J=14.2 Hz), 5.01 (1H,d,J=14.2 Hz), 5.08 (1H,q,J=7 Hz), 5.44 (1H, s), 6.72–6.90 (2H,m), 7.12–7.31 (2H,m), 7.48–7.65 (3H,m), 7.69 (1H,s), 7.76 (1H,s), 7.94 (1H,s).

IR$\gamma_{max}^{KBr}$ cm$^{-1}$: 3420, 3130, 3000, 1703, 1620, 1599.

SIMS (m/z): 431 (M+H) $^+$

Elemental analysis for $C_{20}H_{17}F_3N_6O_2.H_2O$ Calcd: C 53.57, H 4.27, N 18.74 Found: C 53.95, H 4.14, N 18.45

WORKING EXAMPLE 7

1-[(1R,2R)-2-(2,4-Difluorophenyl)-2-hydroxy-1-methyl-3-(1H-1,2,4-triazol-1-yl)propyl]-3-(4-methoxyphenyl)-2(1H,3H)-imidazolone (Compound 7), colorless powder.

Yield: 663 mg (90%).

$^1$H-NMR (CDCl$_3$) δ: 1.21 (3H,d,J=7.2 Hz), 3.83 (3H,s), 4.21 (1H,d,J=14.2 Hz), 4.92 1H,q,J=7.2 Hz), 5.09 (1H,d,J=14.2 Hz), 5.71 (1H,br), 6.58 (1H,d,J=3.2 Hz), 6.68 (1H,d,J=3.2 Hz), 6.70–6.88 (2H,m), 6.97 (2H,d,J=9 Hz), 7.40–7.60 (1H, m), 7.50 (2H,d,J=9 Hz), 7.72 (1H,s), 7.88 (1H,s).

IR$\gamma_{max}^{KBr}$ cm$^{-1}$: 3500, 3120, 3000, 1680, 1614, 1516.

SIMS (m/z): 442 (M+H) $^+$

WORKING EXAMPLE 8

2-[(1R, 2R)-2-(2,4-Difluorophenyl)-2-hydroxy-1-methyl-3-(1H-1,2,4-triazol-1-yl) propyl ]-4-(4-methoxyphenyl)-3-(2H, 4H)-1,2,4-triazolone (Compound 8), colorless powder.

Yield: 672 mg (65% ).

$^1$H-NMR (CDCl$_3$) δ: 1.29 (3H,d,J=7 Hz), 3.85 (3H,s), 4.35 (1H,d,J=14.4 Hz), 5.02 (1H,d,J=14.4 Hz), 5.08 (1H,q, J=7 Hz), 5.56 (1H,s), 6.71–6.89 (2H,m), 7.01 (2H,d,J=9 Hz), 7.45 (2H, d,J=9 Hz), 7.50–7.64 (1H,m), 7.67 (1H,s), 7.73 (1H,s), 7.96 (1H,s).

IR$\gamma_{max}^{KBr}$ cm$^{-1}$: 3500, 3120, 3080, 1693, 1620, 1562, 1516.

SIMS (m/z): 443 (M+H)$^+$

Elemental analysis for $C_{21}H_{20}F_2N_6O_3.H_2O$ Calcd: C 54.78, H 4.82, N 18.25 Found: C 54.86, H 4.64, N 18.06

WORKING EXAMPLE 9

1-[(1R,2R)-2-(2,4-Difluorophenyl)-2-hydroxy-1-methyl-3-(1H-1,2,4-triazol-1-yl)propyl]-3-(4-trifluoromethoxyphenyl)-2(1H,3H)-imidazolone (Compound 9), colorless powder.

Yield: 500 mg, 71%.

$^1$H-NMR (CDCl$_3$) δ: 1.20 (3H,d,J=7 Hz), 4.19 (1H,d,J=14.4 Hz), 4.97 (1H,q,J=7 Hz), 5.10 (1H,d,J=14.4 Hz), 5.51 (1H, br), 6.39 (1H,d,J=3.2 Hz), 6.64 (1H,d,J=3.2 Hz), 6.70–6.86 (2H,m), 7.31 (2H,d,J=9 Hz), 7.38–7.54 (1H,m), 7.69 (2H,d,J=9 Hz), 7.74 (1H,s), 7.84 (1H,s).

IR$\gamma_{max}^{KBr}$ cm$^{-1}$: 1691, 1620, 1599, 1514, 1427, 1252.

WORKING EXAMPLE 10

2-[(1R,2R)-2-(2,4-Difluorophenyl)-2-hydroxy-1-methyl-3-(1H-1,2,4-triazol-1-yl)propyl]-4-(4-trifluoromethylphenyl)-(2H,4H)-1,2,4-triazolone (Compound 10), colorless powder.

Yield: 420 mg (42%).

$^1$H-NMR (CDCl$_3$) δ:1.31 (3H,d,J=7.0 Hz), 4.38 (1H,d,J= 15 Hz), 5.03 (1H,d,J=15 Hz), 5.09 (1H,q,J=7.0 Hz), 5.35 (1H,br), 6.76–6.86 (2H,m), 7.50–7.62 (1H,m), 7.66–7.84 (5H, m), 7.87 (1H,s), 7.94 (1H,s).

WORKING EXAMPLE 11

4-[(1R,2R)-2-(2,4-Difluorophenyl)-2-hydroxy-1-methyl-3-(1H-1,2,4-triazol-1-yl)propyl]-2-(4-trifluoromethylphenyl)-3(2H,4H)-1,2,4-triazolone (Compound 11), white powder.

Yield: 304 mg (24%).

$^1$H-NMR (CDCl$_3$) δ: 1.24 (3H,d,J=7.2 Hz), 4.15 (1H, d,J=14 Hz), 4.97 (1H,dq,J=7.2, 1.4 Hz), 5.08 (1H,q,J=14 Hz), 5.56 (1H,d,J=1.4 Hz), 6.76–6.91 (2H,m), 7.38–7.59 (1H,m), 7.72 (2H,d,J=8.6 Hz), 7.77 (1H,s), 7.80 (1H,s), 8.00 (1H,s), 8.20 (2H,d,J=8.6 Hz).

IRγ$_{max}^{KBr}$ cm$^{-1}$: 3106, 1701, 1618, 1597, 1568, 1520.

WORKING EXAMPLE 12

2-[(1R, 2R)-2-(2,4-Difluorophenyl)-2-hydroxy-1-methyl-3-(1H-1, 2,4-triazol-1-yl)propyl]-4-(4-trifluoromethoxyphenyl)-3(2H,4H)-1,2,4-triazolone (Compound 12), colorless powder.

Yield: 790 mg (47%).

$^1$H-NMR (CDCl$_3$) δ:1.31 (3H,d,J=7 Hz), 4.37 (1H,d,J=14.2 Hz), 5.03 (1H,d,J=14.2 Hz), 5.09 (1H,q,J=7 Hz), 5.41 (1H, s), 6.76–6.90 (2H,m), 7.38 (2H,d,J=9 Hz), 7.51–7.64 (1H,m), 7.65 (2H,d,J=9 Hz), 7.70 (1H,s), 7.81 (1H,s), 7.94 (1H,s).

IRγ$_{max}^{KBr}$ cm$^{-1}$: 1711, 1620, 1562, 1516, 1500, 1427, 1259, 1209.

WORKING EXAMPLE 13

1-[(1R,2R)-2-(2,4-Difluorophenyl)-2-hydroxy-1-methyl-3-(1H-1,2,4-triazol-1-yl)propyl]-3-(4-isopropylphenyl)-(2)1H,3H)-imidazolone (Compound 13), colorless powder.

Yield: 200 mg (84%).

$^1$H-NMR (CDCl$_3$) δ:1.21 (3H,d,J=7 Hz), 1.26 (6H,d,J=6.8 Hz), 2.94 (1H,q,6.8 Hz), 4.19 (1H,d,J=14 Hz), 4.92 (1H,m), 5.09 (1H,d,J=14 Hz), 5.6–5.8(1H,br), 5.62 (1H,d, J=3.2 Hz), 6.69 (1H,d,J=3.2 Hz), 6.7–6.9 (2H,m), 7.30 (2H, d, J=8.6 Hz), 7.4–7.5 (1H,m), 7.52 (2H,d,J=8.4 Hz), 7.71 (1H,s), 7.87 (1H, s).

WORKING EXAMPLE 14

2-[(1R,2R)-2-(2,4-Difluorophenyl)-2-hydroxy-1-methyl-3-(1H-1,2,4-triazol-1-yl)propyl]-4-(2,4-difluorophenyl)-(2H,4H)-1,2,4-triazolone (Compound 14), colorless crystals.

m.p. 111°–113° C.

Yield: 660 mg (47%).

$^1$H-NMR (CDCl$_3$) δ1.32 (3H,d,J=7 Hz), 4.36 (1H,d,J=14.4 Hz), 5.04 (1H,d,J=14.4 Hz), 5.07 (1H,g,J=7 Hz), 5.73 (1H, s), 6.74–6.88 (2H,m), 7.00–7.14 (2H,m), 7.50–7.75 (2H,m), 7.71 (1H,s), 7.73 (1H,d,J=2.4 Hz), 7.95 (1H,s).

IRγ$_{max}^{KBr}$ cm$^{-1}$: 1711, 1614, 1554, 1515, 1500, 1439, 1333, 1273.

WORKING EXAMPLE 15

4-[(1R,2R)-2-(2,4-Difluorophenyl)-2-hydroxy-1-methyl-3-(1H-1,2,4-triazol-1-yl)propyl]-2-(4-fluorophenyl)-3(2H, 4H)-1,2,4-triazolone (Compound 15), colorless powder.

Yield: 545 mg (55%).

$^1$H-NMR (CDCl$_3$) δ:1.23 (3H,d,J=7.2 Hz), 4.15 (1H,d,J=14.2 Hz), 4.95 (1H,dq,J=7.2, 1.6 Hz), 5.08 (1H,d,J=14.2 Hz), 5.56 (1H,d,J=1.6 Hz), 6.78–6.91 (2H,m), 7.14 (2H,t,J=9.4 Hz), 7.39–7.62 (1H,m), 7.77 (1H,s), 7.80 (1H,s), 7.95 (1H,s), 7.99 (2H,dd,J=9.4, 4.8 Hz).

IRγ$_{max}^{KBr}$ cm$^{-1}$: 3093, 1691, 1620, 1599, 1566, 1512.

WORKING EXAMPLE 16

In the same manner as in Working Example 2, reaction was conducted using an about 1:1 mixture of 2-[(1R,2S)-2-(2,4-difluorophenyl)-2,3-epoxy-1-methylpropyl]-4-(4-isopropylphenyl)-3(2H,4H)-1,2,4-triazolone and (1R)-1-[(2R)-2-(2,4-difluorophenyl)-2-oxiranyl ethanol obtained in Reference Example 20 to give 2-[(1R,2R)-2-(2,4-difluorophenyl)-2-hydroxy-1-methyl-3-(1H-1,2,4-triazol-1-yl)propyl]-4-(4-isopropylphenyl)-3 (2H, 4H)-1,2,4-triazolone (Compound 17) as a colorless powder.

$^1$H-NMR (CDCl$_3$) δ: 1.28 (6H,d,J=6.8 Hz), 1.30 (3H,d, J=7 Hz), 2.97 (1H,q,J=6.8 Hz), 4.35 (1H,d,J=14 Hz), 5.03 (1H,d,J=14 Hz), 5.10 (1H,q,J=7 Hz), 5.55 (1H,s), 6.76–6.87 (2H,m), 7.37 (2H,d,J=8.8 Hz), 7.47 (2H,d,J=8.8 Hz), 7.50–7.62 (1H,m), 7.68 (1H,s), 7.77 (1H,s), 7.96 (1H,s).

Elemental analysis for C$_{23}$H$_{24}$F$_2$N$_6$O$_2$ Calcd: C 60.78, H 5.32, H 18.49 Found: C 60.48, H 5.49, N 18.32

WORKING EXAMPLE 17

1-[(1R,2R)-2-(2,4-Difluorophenyl)-2-hydroxy-1-methyl-3-(1H-1,2,4-triazol-1-yl)propyl]-4-(4-trifluoromethylphenyl)-5(1H,4H)-tetrazolone (Compound 18), colorless powder.

Yield: 21%

$^1$H-NMR (CDCl$_3$) δ: 1.47 (3H,d,J=7.2 Hz), 4.36 (1H,d, J=14.2 Hz), 5.08 (1H,d,J=14.2 Hz), 5.10 (1H,q,J=7.2 Hz), 5.47 (1H,s), 6.74–6.91 (2H,m), 7.50–7.68 (1H,m), 7.73 (1H,s), 7.80 (2H,d,J=8.8 Hz), 7.91 (1H,s), 8.18 (2H,d,J=8.8 Hz).

Elemental analysis for C$_{20}$H$_{16}$F$_5$N$_7$O$_2$ Calcd: C 49.90, H 3.35, N 20–37 Found: C 49.64, H 3.35, N 20.22

WORKING EXAMPLE 18

1-[(1R,2R)-2-(2,4-Difluorophenyl)-2-hydroxy-1-methyl-3-(1H-1,2,4-triazol-1-yl)propyl]-3-[4-(2,2,3,3-tetrafluoropropoxy)phenyl]-2(1H,3H)-imidazolone (Compound 19), colorless powder.

Yield: 79%.

$^1$H-NMR (CDCl$_3$) δ:1.20 (3H,d,J=7 Hz), 4.20 (1H,d,J=14 Hz), 4.37 (2H,t,J=12 Hz), 4.94 (1H,q,J=7 Hz), 5.09 (1H,d, J=14 Hz), 5.55–5.74 (1H,br), 6.06 (1H,tt,J=5, 53 Hz), 6.59 (1H,d,J=3 Hz), 6.72 (1H,d,J=3 Hz), 6.74–6.85 (2H,m), 7.01 (2H,d,J=9 Hz), 7.42–7.55 (1H,m), 7.58 (2H,d,J=9 Hz), 7.73 (1H,s), 7.86 (1H,s).

m.p. 124.5°–125.5° C.

Elemental analysis for C$_{24}$H$_{21}$F$_6$N$_5$O$_3$ Calcd: C 53.24, H 3.91, N 12.93 Found: C 53.12, H 4.19, N 12.76

[α]$_D^{20}$ −17.9° (c=0.3, methanol)

WORKING EXAMPLE 19

2-[(1R,2R)-2-(2,4-Difluorophenyl)-2-hydroxy-1-methyl-3-(1H-1,2,4-triazol-1-yl)propyl]-4-[4-(4-benzyl-1-piperazinyl)phenyl]-3(2H,4H)-1,2,4-triazolone (Compound 21), colorless powder.

Yield: 59%.

$^1$H-NMR (CDCl$_3$) δ:1.28 (3H,d,J=7 Hz), 2.62 (4H,t,J=4.8 Hz), 3.25 (4H,t,J=4.8 Hz), 3.58 (2H,s), 4.33 (1H,d,J=14.2 Hz), 5.01 (1H,d,J=14.2 Hz), 5.08 (1H,q,J=7 Hz), 5.60 (1H, s), 6.72–6.91 (2H,m), 6.98 (2H,d,J=9 Hz), 7.23–7.45 (7H, m), 7.45–7.62 (1H,m), 7.66 (1H,s), 7.71 (1H,s), 7.96 (1H,s).

Elemental analysis for C$_{31}$H$_{32}$F$_2$N$_8$O$_2$·0.5H$_2$O Calcd: C 62.51, H 5.58, N 18.81 Found: C 62.28, H 5.44, N 18.56

WORKING EXAMPLE 20

4-[4-(4-Acetyl-1-piperazinyl)phenyl]-2-[(1R,2R)-2-(2,4-difluorophenyl)-2-hydroxy-1-methyl-3-(1H-1,2,4-triazol-1-yl)propyl]-3(2H,4H)-1,2,4-triazolone (Compound 23).

To a solution of 170 mg of compound 21 in 20 ml of ethanol was added 20 mg of 10% Pd-C and the mixture was stirred at room temperature in a hydrogen stream for 9 hours. The catalyst was filtered off and washed with 5 ml of ethanol. The filtrate and the washing were combined and concentrated under reduced pressure to give 144 mg of 2-[(1R,2R)-2-(2,4-difluorophenyl)-2-hydroxy-1-methyl-3-(1H-1,2,4-triazol-1-yl)propyl]-4-[4-(1-piperazinyl)phenyl]-3(2H,4H)-1,2,4-triazolone (Compound 22) as a pale yellow oil.

To a solution of 144 mg of the compound 22. in 20 ml of methylene chloride were added 0.044 ml of triethylamine at 0° C. and then 0.030 ml of acetic anhydride and the resulting mixture was stirred for 1 hour. The reaction solution was washed with water and saturated aqueous solution of sodium chloride successively, dried over anhydrous magnesium sulfate and concentrated under reduced pressure. The concentrate was purified by silica gel chromatography (eluate; ethyl acetate to ethyl acetate:methanol=10:1) to give 80 mg of the compound 23 as a pale yellow powder.

$^1$H-NMR (CDCl$_3$) δ:1.29 (3H,d,J=7 Hz), 2.16 (3H,s), 3.15–3.35 (4H,m), 3.59–3.88 (4H,m), 4.35 (1H,d,J=14.4 Hz), 5.01 (1H,d,J=14.4 Hz), 5.08 (1H,q,J=7 Hz), 5.57 (1H, s), 6.75–6.90 (2H,m), 7.01 (2H,d,J=9 Hz), 7.44 (2H,d,J=9 Hz), 7.49–7.67 (1H,m), 7.68 (1H,s), 7.73 (1H,s), 7.98 (1H, s).

Elemental analysis for C$_{26}$H$_{28}$F$_2$N$_8$O$_3$.1.5H$_2$O Calcd: C 55.20, H 5.52, N 19.81 Found: C 55.55, H 5.22, N 19.77

WORKING EXAMPLES 21–50

The following compounds were obtained in accordance with the same manner as in Working Example 2.

WORKING EXAMPLE 21

2-[(1R,2R)-2-(2,4-Difluorophenyl)-2-hydroxy-1-methyl-3-(1H-1,2,4-triazol-1-yl)propyl]-4-[4-[4-(4-methoxyphenyl)-1-piperazinyl]phenyl]-3(2H,4H)-1,2,4-triazolone (Compound 24), colorless prisms.

m.p. 204°–205° C.

Yield 97%.

$^1$H-NMR (CDCl$_3$) δ: 1.29 (3H,d,J=7 Hz), 3.18–3.30 (4H, m), 3.30–3.46 (4H,m), 3.79 (3H,s), 4.35 (1H,d,J=14.4 Hz), 5.01 (1H,d,J=14.4 Hz), 5.09 (1H,q,J=7 Hz), 5.59 (1H,s), 6.72–6.90 (2H,m), 6.87 (2H,d,J=9.2 Hz), 6.97 (2H,d,J=9.2 Hz), 7.06 (2H, d,J=9.2 Hz), 7.43 (2H,d,J=9.2 Hz), 7.50–7.66 (1H,m), 7.68 (1H, s), 7.73 (1H,s), 7.97 (1H,s).

Elemental analysis for C$_{31}$H$_{32}$F$_2$N$_8$O$_3$ Calcd: C 61.78, H 5.35, N 18.59 Found: C 61.45, H 5.37, N 18.29

WORKING EXAMPLE 22

2-[(1R,2R)-2-(2,4-Difluorophenyl)-2-hydroxy-1-methyl-3-(1H-1,2,4-triazol-1-yl)propyl]-4-(3-trifluoromethylphenyl)-3(2H,4H)-1,2,4-triazolone (Compound 25), colorless powder.

Yield 30%.

$^1$H-NMR (CDCl$_3$) δ:1.32 (3H,d,J=7.0 Hz), 4.36 (1H,d,J=14.6 Hz), 5.04 (1H,d,J=14.6 Hz), 5.09 (1H,q,J=7.0 Hz), 5.36 (1H, s), 6.76–6.86 (2H,m), 7.5–7.7 (4H,m), 7.78–7.90 (2H, m), 7.86 (1H,s), 7.93 (1H,s).

Elemental analysis for C$_{21}$H$_{17}$F$_5$N$_6$O$_2$ Calcd: C 52.50, H 3.57, N 17.49 Found: C 52.64, H 3.72, N 17.15

WORKING EXAMPLE 23

1-[(1R,2R)-2-(2,4-Difluorophenyl)-2-hydroxy-1-methyl-3-(1H-1,2,4-triazol-1-yl)propyl]-4-(4-fluorophenyl)-5(1H, 4H)-tetrazolone (Compound 26.), colorless powder.

Yield 51%.

$^1$H-NMR (CDCl$_3$) δ:1.46 (3H,d,J=7.2 Hz), 4.35 (1H,d,J=14.4 Hz), 5.08 (1H,d,J=14.4 Hz), 5.10 (1H,q,J=7.2 Hz), 5.50 (1H,s), 6.72–6.90 (2H,m), 7.15–7.30 (2H,m), 7.50–7.68 (1H, m), 7.72 (1H,s), 7.91 (1H,s), 7.89–8.01 (2H,m).

Elemental analysis for C$_{19}$H$_{16}$F$_3$N$_7$O$_2$.H$_2$O Calcd: C 50.78, H 4.04, N 21.82 Found: C 50.83, H 3.71, N 21.68

WORKING EXAMPLE 24

2-[(1R,2R)-2-(2,4-Difluorophenyl)-2-hydroxy-1-methyl-3-(1H-1,2,4-triazol-1-yl)propyl]-4-(4-pyridyl)3-(2H,4H)-1,2,4-triazolone (Compound 27), colorless powder.

Yield 41%.

$^1$H-NMR (CDCl$_3$) δ:1.36 (3H,d,J=7.2 Hz), 4.37 (1H,d,J=14.2 Hz), 5.01 (1H,d,J=14.2 Hz), 5.07 (1H,q,J=7.2 Hz), 5.31 (1H, s), 6.74–6.90 (2H,m), 7.50–7.65 (1H,m), 7.67 (1H,s), 7.69 (1H,s), 7.70(1H,s), 7.93 (2H,d,J=5.8 Hz), 8.75 (2H,d, J=5.8 Hz).

Elemental analysis for C$_{19}$H$_{17}$F$_2$N$_7$O$_2$.1.5H$_2$O Calcd: C 51.82, H 4.58, N 22.25 Found: C 51.47, H 4.24, N 22.48

WORKING EXAMPLE 25

2-[(1R,2R)-2-(2,4-Difluorophenyl)-2-hydroxy-1-methyl-3-(1H-1,2,4-triazol-1-yl)propyl]-4-(4-pyrinlidinyl)-3(2H, 4H)-1,2,4-triazolone (Compound 28), colorless powder.

Yield 10%.

$^1$H-NMR (CDCl$_3$) δ:1.41 (3H,d,J=6.6 Hz), 4.32 (1H,d,J=11.6 Hz), 4.78 (1H,q,J=6.6 Hz), 4.90 (1H,d,J=11.6 Hz), 5.41 (1H,s), 6.70–6.92 (2H,m), 7.44 (1H,s), 7.89 (1H,dd,J=5.6 Hz, 1.2 Hz), 7.85–8.06 (1H,m), 8.15 (1H,s), 8.90 (1H,d,J=5.6 Hz), 9.10 (1H,d,J=1.2 Hz), 9.26 (1H,s).

Elemental analysis for C$_{18}$H$_{16}$F$_2$N$_8$O$_2$.0.5H$_2$O Calcd: C 51.06, H 4.05, N 25.47 Found: C 50.70, H 3.71, N 25.62

WORKING EXAMPLE 26

2-[(1R,2R)-2-(2,4-Difluorophenyl)-2-hydroxy-1-methyl-3-(1H-1,2,4-triazol-t-yl)propyl]-4-(2,2,2-trifluoroethyl)-3-(2H,4H)-1,2,4-triazolone (Compound 29), colorless powder.

Yield 53%

$^1$H-NMR (CDCl$_3$) δ: 1.28 (3H,d,J=7.2 Hz), 4.25 (1H,d, J=14.5 Hz), 4.32 (2H,dq,J=1.6 Hz,J=8.6 Hz), 5.00 (1H,q,J= 7.2 Hz), 5.02 (1H,d,J=14.5 Hz), 5.29 (1H,s), 6.72–6.88 (2H,m), 7.48–7.60 (1H,m), 7.63 (1H,s), 7.70 (1H,s), 7.93 (1H,s).

The above compound was treated with 4N hydrochloric acid-ethyl acetate solution to give the hydrochloride as a colorless powder.

IRγcm$^{-1}$ (KBr): 1716, 1700, 1689, 1652, 1618, 1560, 1506.

WORKING EXAMPLE 27

2-[(1R,2R)-2-(2,4-Difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone (Compound. 30), colorless crystalline powder.

Yield 63% m.p. 150°–151° C (isopropyl ether).

IR$\gamma_{max}^{KBr}$ cm$^{-1}$: 1716, 1697, 1618, 1558, 1517, 1506.

$^1$H-NMR (CDCl$_3$) δ: 1.30 (3H,d,J=7 Hz), 4.37 (1H,d,J=15 Hz), 4.40 (2H,tt,J=11.8 Hz,1.4 Hz), 5.02 (1H,d,J=15 Hz), 5.47 (1H,s), 5.09 (1H,q,J=7 Hz), 6.07 (1H,tt,J=53 Hz,J=4.8 Hz), 6.75–6.88 (2H,m), 7.07 (2H,dt,J=9 Hz,J=2.2 Hz), 7.53 (2H,dt,J=9 Hz, J=2.2 Hz), 7.50–7.64 (1H,m), 7.69 (1H,s), 7.75 7.95 (1H,s).

Elemental analysis for C$_{23}$H$_{20}$F$_6$N$_6$O$_3$ Calcd: C 50.93, H 3.72, N 15.49 Found: C 50.91, H 3.84, N 15.47

WORKING EXAMPLE 28

2-[(1R,2R)-2-(2,4-Difluorophenyl)-2-hydroxy-1-methyl-3-(1H-1,2,4-triazol-1-yl)propyl]-4-(2-trifluoromethylphenyl)-3(2H,4H)-1,2,4-triazolone (Compound 31), colorless powder.

Yield 28%.

$^1$H-NMR (CDCl$_3$) δ:1.32 (3H,d,J=7 Hz), 4.29 (1H,d,J=14.2 Hz), 5.06 (1H,d,J=14.2 Hz), 5.07 (1H,q,J=7 Hz), 5.41 (1H, s), 6.74–6.86 (2H,m), 7.48–7.60 (3H,m), 7.6.3–7.90 (3H,m), 7.70 (1H,s), 7.97 (1H,s).

Elemental analysis for C$_{21}$H$_{17}$F$_5$N$_6$O$_2$ Calcd: C 52.50, H 3.57, N 17.49 Found: C 52.32, H 3.76, N 17.35 SIMS (m/z): 481 (M+H)$^+$.

WORKING EXAMPLE 29

2-[(1R,2R)-2-(2,4-Difluorophenyl)-2-hydroxy-1-methyl-3-(1H-1,2,4-triazol-1-yl)propyl]-4-(4-isopropoxyphenyl)-3(2H,4H)-1,2,4-triazolone (Compound 32), colorless powder.

Yield 80%.

$^1$H-NMR (CDCl$_3$) δ:1.29 (3H,d,J=7.0 Hz), 1.36 (6H,d, J=6 Hz), 4.35 (1H,d,J=14.2 Hz), 4.58 (1H,septet,J=6 Hz), 5.02 (1H,d,J=14.2 Hz), 5.08 (1H,q,J=7 Hz), 5.57 (1H,s), 6.72–6.89 (2H,m), 6.99 (2H,d,J=9 Hz), 7.42 (2H,d,J=9 Hz), 7.47–7.63 (1H,m), 7.67 (1H,s), 7.72 (1H,s), 7.96 (1H,s).

Elemental analysis for C$_{23}$H$_{24}$F$_2$N$_6$O$_3$·H$_2$O Calcd: C 56.55, H 5.36, N 17.20 Found: C 56.36, H 5.15, N 17.26

WORKING EXAMPLE 30

2-[(1R,2R)-2-(2,4-Difluorophenyl)-2-hydroxy-1-methyl-3-(1H-1,2,4-triazol-1-yl)propyl]-4-(3-methylbutyl)-3(2H, 4H)-1,2,4-triazolone (Compound 33), colorless oil.

Yield 53%.

$^1$H-NMR (CDCl$_3$) δ: 0.99 (6H,d,J=6.2 Hz), 1.23 (3H,d, J=6.8 Hz), 1.56–1.80 (3H,m), 3.72 (2H,t,J=7.2 Hz), 4.20 (1H,d,J=14.2 Hz), 4.97 (.1H,d,J=14.2 Hz), 5.02 (1H,q,J=6.8 Hz), 5.63 (1H,s), 6.72–6.90 (2H,m), 7.45–7.62 (1H,m), 7.50 (1H,s), 7.67 (1H,s), 7.96 (1H,s).

SIMS (m/z): 407 (M+H)$^+$

WORKING EXAMPLE 31

2-[(1R,2R)-2-(2,4-Difluorophenyl)-2-hydroxy-1-methyl-3-(1H-1,2,4-triazol-1-yl)propyl]-4-[4-(1,1,2,2-tetrafluoroethoxy)phenyl]-3(2H,4H)-1,2,4-triazolone (Compound 34), colorless powder.

Yield 65%.

IR$\gamma$cm$^{-1}$ (KBr): 1710, 1691, 1620, 1564, 1511, 1276.

$^1$H-NMR (CDCl$_3$) δ: 1.31 (3H,d,J=7 Hz), 4.37 (1H,d,J=14.2 Hz), 5.02 (1H,d,J=14.2 Hz), 5.09 (1H,q,J=7 Hz), 5.41 (1H, s), 5.94 (1H,tt,J=53 Hz,J=2.8 Hz), 6.75–6.90 (2H,m), 7.38 (2H, d,J=9 Hz), 7.50–7.70 (1H,m), 7.63 (2H,d,J=9 Hz), 7.70 (1H,s), 7.80 (1H,s), 7.94 (1H,s).

WORKING EXAMPLE 32

2-(4-Chlorophenyl)-4-[(1R,2R)-2-(2,4-difluorophenyl)-2-hydroxy-1-methyl-3-(1H-1,2,4-triazol-1-yl)propyl]-3(2H, 4H)-1,2,4-triazolone (Compound 35), colorless prisms.

Yield 66%.

$^1$H-NMR (CDCl$_3$) δ: 1.23 (3H,d,J=7.2 Hz), 4.14 (1H,d, J=14.2 Hz), 4.95 (1H,dq,J=7.2 Hz, 1.6 Hz), 5.07 (1H,d,J=14.2 Hz), 5.54 (1H,d,J=1.6 Hz), 6.73–6.89 (2H,m), 7.37–7.50 (1H,m), 7.41 (2H,d,J=9 Hz), 7.77 (1H,s), 7.93 (1H,s), 7.96 (1H,s), 7.98 (2H,d,J=9 Hz).

Elemental analysis for C$_{20}$H$_{17}$C$_1$F$_2$N$_6$O$_2$ Calcd: C 53.76, H 3.83, N 18.81 Found: C 53.93, H 4.00, N 18.44

WORKING EXAMPLE 33

4-[(1R,2R)-2-(2,4-Difluorophenyl)-2-hydroxy-1-methyl-3-(1H-1,2,4-triazol-1-yl)propyl]-2-(4-trifluoromethoxyphenyl)-3(2H,4H)-1,2,4-triazolone (Compound 36), colorless powder.

Yield 68%.

$^1$H-NMR (CDCl$_3$) δ: 1.24-(3H,d,J=7.2 Hz), 4.14 (H,d,J=14.4 Hz), 4.96 (1H,dq,J=7.2, 1.6 Hz), 5.08 (1H,d,J=14.4 Hz), 5.56 (1H,d,J=1.6 Hz), 6.75–6.90 (2H,m), 7.31 (2H,d, J=9.2 Hz), 7.48–7.52 (1H,m), 7.77 (1H,s), 7.80 (1H,s), 7.97 (1H,s), 8.08 (2H,d,J=9.2 Hz).

WORKING EXAMPLE 34

1-[(1R,2R)-2-(2,4-Difluorophenyl)-2-hydroxy-1-methyl-3-(1H-1,2,4-triazol-1-yl)propyl]-4-(4-trifluoromethoxyphenyl)-5(1H,4H)-tetrazolone (Compound 37): colorless powder.

Yield: 43%

$^1$H-NMR (CDCl$_3$) δ: 1.46 (3H,d,J=7.2 Hz), 4.35 (1H,d, J=13.8 Hz), 5.08 (1H,d,J=13.8 Hz), 5.10 (1H,q,J=7.2 Hz), 5.51 (1H,s), 6.71–6.90 (2H,m), 7.38 (2H,d,J=9.2 Hz), 7.48–7.63 (1H,m), 7.72 (1H,s), 7.91 (1H,s), 8.04 (2H,d,J=9.2 Hz).

IR$\gamma_{max}^{KBr}$ cm$^{-1}$: 3400, 3010, 1722, 1684, 1618, 1599, 1510.

$[\alpha]_D^{20}$ –5.7° (c=1, methanol)

WORKING EXAMPLE 35

1-[(1R,2R)-2-(2,4-Difluorophenyl)-2-hydroxy-1-methyl-3-(1H-1,2,4-triazol-1-yl)propyl]-4-[(4-(2,2,3,3-tetrafluoropropoxy)phenyl]-5(1H,4H)-tetrazolone (Compound 38 ), colorless powder.

Yield: 57%

$^1$H-NMR (CDCl$_3$) δ: 1.45 (3H,d,J=7.2 Hz), 4.35 (1H,d, J=14.2 Hz), 4.41 (2H,t,J=11.8 Hz), 5.08 (1H,d,J=14.2 Hz), 5.11 (1H,q,J=7.2 Hz), 5.53 (1H,s), 6.09 (1H,tt,J=53.2, 4.8 Hz), 6.75–6.90 (2H,m), 7.08 (2H,d,J=9 Hz), 7.50–7.68 (1H, m), 7.72 (1H,s), 7.90 (2H,d,J=9 Hz), 7.92 (1H,s).

IR$\gamma_{max}^{KBr}$ cm$^{-1}$: 3400, 3050, 1726, 1618, 1599, 1516, 1423.

$[\alpha]_D^{20}$ –2.3° (c=0.4, methanol)

WORKING EXAMPLES 36

1-(4-Chlorophenyl)-4-[(1R, 2R)-2-(2,4-difluorophenyl)-2-hydroxy-1-methyl-3-(1H-1,2,4-triazol-1-yl)propyl]-5(1H, 4H)-tetrazolone (Compound 39), colorless powder.

Yield: 46%

$^1$H-NMR (CDCl$_3$) δ:1.46 (3H,d,J=7 Hz), 4.35 (1H,d,J=14.4 Hz), 5.08 (1H,d,J=14.4 Hz), 5.10 (1H,g,J=7 Hz), 5.49 (1H,s), 6.72–6.91 (2H,m), 7.42–7.61 (1H,m), 7.50 (2H,d, J=9 Hz), 7.72 (1H,s), 7.92 (1H,s), 7.94 (2H,d,J=9 Hz).

IRγ$_{max}^{KBr}$ cm$^{-1}$: 3450, 3090, 1726, 1618, 1599, 1497.

Elemental analysis for C$_{19}$H$_{16}$ClF$_2$N$_7$O$_2$.0.5 H$_2$O Calcd: C 49.95, H 3.75, N 21.46 Found: C 50.08, H 3.74, N 21.52

[α]$_D^{20}$ −3.2° (c=0.5, methanol)

WORKING EXAMPLE 37

1-[(1R,2R)-2-(2,4-Difluorophenyl)-2-hydroxy-1-methyl-3-(1H-1,2,4-triazol-1-yl)propyl]-3-[4-(1,1,2,2-tetrafluoroethoxy)phenyl]-2(1H,3H)-imidazolone (Compound 40), colorless powder.

Yield: 66%.

$^1$H-NMR (CDCl$_3$) δ:1.21 (3H,d,J=7 Hz), 4.18 (1H,d,J=14 Hz), 4.97 (1H,q,J=7 Hz), 5.10 (1H,d,J=14 Hz), 5.4–5.6 (1H,br), 5.93 (1H,tt,J=53, 2.8 Hz), 6.64 (1H,d,J=3 Hz), 6.77 (1H,d,J=3 Hz), 6.74–6.84 (2H,m), 7.30 (2H,d,J=9 Hz), 7.40–7.55 (1H,m), 7.67 (2H,d,J=9 Hz), 7.74 (1H,s), 7.84 (1H,s).

Elemental analysis for C$_{23}$H$_{19}$F$_6$N$_5$O$_3$ Calcd: C 52.38, H 3.63, N 13.28 Found: C 52.22, H 3.83, N 13.08 [α]$_D^{20}$ −18.4° (c=0.6, methanol)

WORKING EXAMPLE 38

1-(4-Chlorophenyl)-3-[(1R,2R)-2-(2,4-difluorophenyl)-2-hydroxy-1-methyl-3-(1H-1,2,4-triazol-1-yl)propyl]-2(1H, 3H)-imidazolone (Compound 41), colorless powder.

Yield: 54%

$^1$H-NMR (CDCl$_3$) δ: 1.20 (3H,d,J=7 Hz), 4.19 (1H,d,J=14 Hz), 4.97 (1H,q,J=7 Hz), 5.10 (1H,d,J=14 Hz), 5.42–5.65 (1H,br), 6.63 (1H,d,J=3.2 Hz), 6.75 (1H,d,J=3.2 Hz), 6.78–6.85 (2H,m), 7.42 (2H,d,J=9 Hz), 7.40–7.55 (1H,m), 7.61 (2H,d,J=9 Hz), 7.74 (1H,s), 7.85 (1H,s)

WORKING EXAMPLE 39

4-(4-Chlorophenyl)-2-[(1R,2R)-2-(2,4-difluorophenyl)-2-hydroxy-1-methyl-3-(1H-1,2,4-triazol-1-yl)propyl]-3(2H, 4H)-1,2,4-triazolone (Compound 42), colorless powder.

Yield: 42%

$^1$H-NMR (CDCl$_3$) δ: 1.30 (3H,d,J=7.0 Hz), 4.36 (1H,d, J=14 Hz), 5.02 (1H,d,J=14 Hz), 5.08 (1H,q,J=7.0 Hz), 5.41 (1H,s), 6.75–6.86 (2H,m), 7.47–7.63 (5H,m), 7.70 (1H,s), 7.79 (1H,s), 7.94 (1H,s)

WORKING EXAMPLE 40

1-[(1R, 2R)-2-(2,4-Difluorophenyl)-2-hydroxy-1-methyl-3-(1H-1, 2,4-triazol-1-yl)propyl ]-3-[4-(2,2,3,3,4,4,5,5-octafluoropentoxy)phenyl]-2 (1H, 3H)-imidazolone (Compound 43), colorless powder.

Yield: 74%

$^1$H-NMR (CDCl$_3$) δ: 1.20 (3H,d,J=7.0 Hz), 4.20 (1H,d, J=14.3 Hz), 4.49 (2H,t,J=13 Hz), 4.94 (1H,q,J=7.0 Hz), 5.09 (1H,d,J=14.3 Hz), 5.5–5.7 (1H,br), 5.09 (1H,tt,J=52, 5.4 Hz), 6.59 (1H,d,J=3.2 Hz), 6.72 (1H,d,J=3.2 Hz), 6.75–6.85 (2H,m), 7.03 (2H,d,J=9.0 Hz), 7.42–7.54 (1H,m), 7.58 (2H, d,J=9.0 Hz), 7.73 (1H,s), 7.85 (1H,s)

WORKING EXAMPLE 41

1-[(1R, 2R)-2-(2,4-Difluorophenyl)-2-hydroxy-1-methyl-3-(1H-1,2,4-triazol-1-yl)propyl]-3-[4-(2,2,2-trifluoroethoxy)phenyl]-2(1H,3H)-imidazolone (Compound 44), colorless powdery crystals.

Yield: 70%

$^1$H-NMR (CDCl$_3$) δ: 1.21 (3H,d,J=6.8 Hz), 4.20 (1H,d, J=14.2 Hz), 4.38 (2H,q,J=8 Hz), 4.95 (1H,q,J=6.8 Hz), 5.10 (1H,d,J=14.2 Hz), 5.60 (1H,br), 6.60 (1H,d,J=3 Hz), 6.73 (1H,d,J=3 Hz), 6.70–6.88 (2H,m), 7.03 (2H,d,J=9 Hz), 7.40–7.55 (1H,m), 7.58 (2H,d,J=9 Hz), 7.73 (1H,s), 7.86 (1H,s)

WORKING EXAMPLE 42

1-[(1R,2R)-2-(2,4-Difluorophenyl)-2-hydroxy-1-methyl-3-(1H-1,2,4-triazol-1-yl)propyl]-3-[4-(2,2,3,3,3-pentafluoropropoxy)phenyl]-2(1H,3H)-imidazolone (Compound 45), colorless powdery crystals.

Yield: 79%

$^1$H-NMR (CDCl$_3$) δ:1.21 (3H,d,J=7 Hz), 4.20 (1H,d,J=14.2 Hz), 4.45 (2H,t,J=12 Hz), 4.95 (1H,q,J=7 Hz), 5.10 (1H,d,J=14.2 Hz), 5.60 (1H,br), 6.60 (1H,d,J=3 Hz), 6.74 (1H,d,J=3 Hz), 6.65–6.85 (2H,m), 7.03 (2H,d,J=8.8 Hz), 7.40–7.55 (1H,m), 7.59 (2H,d,J=8.8 Hz), 7.74 (1H,s), 7.86 (1H,s)

WORKING EXAMPLE 43

2-[(1R,2R)-2-(2,4-Difluorophenyl)-2-hydroxy-1-methyl-3-(1H-1,2,4-triazol-1-yl)propyl]-4-[4-(2,2,2-trifluoroethoxy)phenyl]-3(2H,4H)-1,2,4-triazolone (Compound 46), colorless needles Yield: 59%

$^1$H-NMR (CDCl$_3$) δ: 1.30 (3H,d,J=7 Hz), 4.36 (1H,d,J=14.8 Hz), 4.41 (2H,q,J=8 Hz), 5.02 (1H,d,J=14.8 Hz), 5.09 (1H,q,J=7 Hz), 5.48 (1H,s), 6.74–6.90 (2H,m), 7.09 (2H,d, J=9 Hz), 7.48–7.65 (1H,m), 7.53 (2H,d,J=9 Hz), 7.69 (1H,s), 7.76 (1H,s), 7.95 (1H,s)

WORKING EXAMPLE 44

2-[(1R,2R)-2-(2,4-Difluorophenyl)-2-hydroxy-1-methyl-3-(1H-1,2,4-triazol-1-yl)propyl]-4-[4-(2,2,3,3,3-pentafluoropropoxy)phenyl]-3(2H,4H)-1,2,4-triazolone (Compound 47), colorless needles Yield: 46%

$^1$H-NMR (CDCl$_3$) δ: 1.30 (3H,d,J=7 Hz), 4.36 (1H,d,J=14.8 Hz), 4.48 (2H,t,J=12 Hz), 5.02 (1H,d,J=14.8 Hz), 5.09 (1H,q,J=7 Hz), 5.48 (1H,s), 6.75–6.90 (2H,m), 7.09 (1H, d,J=9 Hz), 7.48–7.64 (1H,m), 7.54 (2H,d,J=9 Hz), 7.70 (1H,s), 7.76 (1H,s), 7.95 (1H,s)

WORKING EXAMPLE 45

2-[(1R, 2R)-2-(2,4-Difluorophenyl)-2-hydroxy-1-methyl-3-( 1H-1,2,4-triazol-1-yl)propyl]-4-[4-(2,2,3,3,4,4,5,5-octafluoropentoxy)phenyl]-3(2H,4H)-1,2,4-triazolone (Compound 48), colorless powder.

Yield: 54%.

$^1$H-NMR (CDCl$_3$) δ:1.30 (3H,d,J=7.0 Hz), 4.36 (1H,d,J=14 Hz), 4.52 (2H,t,J=13 Hz), 5.01 (1H,t,J=14 Hz), 5.09 (1H,q,J=7.0 Hz), 5.48 (1H,s), 6.10 (1H,tt,J=52, 5.4 Hz), 6.77–6.87 (2H,m), 7.09 (2H,d,J=9.0 Hz), 7.51–7.62 (1H,m), 7.54 (2H,d,J=9.0 Hz), 7.70 (1H, s), 7.76 (1H,s), 7.95 (1H,s)

6.71–6.90 (2H,m), 7.30 (2H,d,J=9.2 Hz), 7.34–7.51 (1H,m), 7.77 (1H,s), 7.80 (1H,s), 7.96 (1H,s), 8.06 (2H,d,J=9.2 Hz)

WORKING EXAMPLE 46

4-[(1R,2R)-2-(2,4-Difluorophenyl)-2-hydroxy-1-methyl-3-(1H-1,2,4-triazol-1-yl)propyl]-2-[4-(2,2,2-trifluoroethoxy)phenyl]-3(2H,4H)-1,2,4-triazolone (Compound 49), colorless powder.

Yield: 68%.

$^1$H-NMR (CDCl$_3$) δ: 1.24 (3H,d,J=7.2 Hz), 4.15 (1H,d, J=14.2 Hz), 4.39 (2H,q,J=8.2 Hz), 4.95 (1H,dq,J=7.2, 1.6 Hz), 5.09 (1H,d,J=14.2 Hz), 5.56 (1H,d,J=1.6 Hz), 6.70–6.90 (2H,m), 7.03 (2H,d,J=9.2 Hz), 7.34–7.53 (1H, m), 7.77 (1H,s), 7.81 (1H,s), 7.94 (1H,s), 7.96 (2H,d,J=9.2 Hz)

WORKING EXAMPLE 47

4-[(1R,2R)-2-(2,4-Difluorophenyl)-2-hydroxy-1-methyl-3-(1H-1,2,4-triazol-1-yl)propyl]-2-[4-(2,2,3,3,3-pentafluoropropoxy)phenyl]-3(2H,4H)-1,2,4-triazolone (Compound 50), colorless powder.

Yield: 53%.

$^1$H-NMR (CDCl$_3$) δ:1.24 (3H,d,J=7.2 Hz), 4.14 (1H,d,J= 14.4 Hz), 4.45 (2H,t,J=12.2 Hz), 4.95 (1H,dq,J=7.2, 1.6 Hz), 5.08 (1H,d,J=14.4 Hz), 5.54 (1H,d,J=1.6 Hz), 6.71–6.89 (2H,m), 7.03 (2H,d,J=9 Hz), 7.34–7.52 (1H,m), 7.77 (1H,s), 7.80 (1H,s), 7.93 (1H,s), 7.96 (2H,d,J=9 Hz)

WORKING EXAMPLE 48

4-[(1R,2R)-2-(2,4-Difluorophenyl)-2-hydroxy-1-methyl-3-(1H-1,2,4-triazol-1-yl)propyl]-2-[4-(2,2,3,3,4,4,5,5-octafluoropentoxy)phenyl]-3(2H,4H)-1,2,4-triazolone (Compound 51), colorless powder.

Yield: 37%.

$^1$H-NMR (CDCl$_3$) δ:1.24 (3H,d,J=7 Hz)., 4.14 (1H,d,J= 14.4 Hz), 4.49 (2H,t,J=13 Hz), 4.94 (1H,dq,J=7, 1.6 Hz), 5.08 (1H,d,J=14.4 Hz), 5.54 (1H,d,J=1.6 Hz), 6.10 (1H,tt, J=52 Hz, 5.4 Hz), 6.71–6.89 (2H,m), 7.03 (2H,d,J=9–2 Hz), 7.34–7.51 (1H,m), 7.77 (1H,s), 7.80 (1H,s), 7.93 (1H,s), 7.95 (2H,d,J=9.2 Hz)

WORKING EXAMPLE 49

4-[(1R,2R)-2-(2,4-Difluorophenyl)-2-hydroxy-1-methyl-3-(1H-1,2,4-triazol-1-yl)propyl]-2-[4-(2,2,3,3-tetrafluoropoxy)phenyl]-3(2H,4H)-1,2,4-triazolone (Compound 52), colorless powder.

Yield: 81%

$^1$H-NMR (CDCl$_3$) δ:1.23 (3H,d,J=7 Hz), 4.14 (1H,d,J= 14.4 Hz), 4.49 (2H,t,J=13 Hz), 4.94 (1H,dq,J=7, 1.6 Hz), 5.08 (1H,d,J=14.4 Hz), 5.54 (1H,d,J=1.6 Hz), 6.10 (1H,tt,J= 52, 5.4 Hz), 6.71–6.89 (2H,m), 7.03 (2H,d,J=9.2 Hz), 7.34–7.51 (1H,m), 7.77 (1H,s), 7.80 (1H,s), 7.93 (1H,s), 7.95 (2H, d. J=9.2 Hz)

WORKING EXAMPLE 50

4-[(1R, 2R)-2-(2,4-Difluorophenyl)-2-hydroxy-1-methyl-3-(1H-1,2,4-triazol-1-yl)propyl]-2-[4-(1,1,2,2-tetrafluoroethoxy)phenyl]-3(2H, 4H)-1,2,4-triazolone (Compound 53), colorless powder Yield: 57%

$^1$H-NMR (CDCl$_3$) δ: 1.24 (3H,d,J=7.2 Hz), 4.14 (1H,d, J=14.2 Hz), 4.95 (1H,dq,J=7.2, 1.6 Hz), 5.08 (1H,d,J=14.2 Hz), 5.55 (1H,d,J=1.6 Hz), 5.93 (1H,tt,J=53, 2.8 Hz),

WORKING EXAMPLE 51

60% Sodium hydride in oil (80 mg) was dispersed in 5 ml of dimethylformamide, and 582 mg of 4-[4-(2,2,3,3-tetrafluoropropoxy)phenyl]-3(2H,4H)-1,2,4-triazolone was added with ice cooling. The mixture was stirred at room temperature for 10 minutes. To the mixture was added 474 mg of (2RS)-2-(2,4-difluorophenyl)-2-(1H-1,2,4-triazol-1-yl)methyloxyrane (synthesized by the method under Japanese Patent Laid-Open Sho 58-32868) and the resulting mixture was heated at 60° C. for 15 minutes. After cooling, the reaction solution was fractionated after adding 20 ml of cold water and 40 ml of ethyl acetate and the separated aqueous layer was extracted with ethyl acetate twice. The ethyl acetate layers were combined, washed with water and saturated aqueous solution of sodium chloride successively, dried over magnesium sulfate and distilled off under reduced pressure. The residue was purified by silica gel chromatography (eluate; dichloromethane:acetone=2:1) to give 510 mg of 2-[(2RS)-2-(2,4-difluorophenyl)-2-hydroxy-3-(1H-1,2,4-triazol-1-yl)propyl]-4-[4-(2,2,3,3-tetrafluoropropoxy)phenyl]-3(2H,4H)-1,2,4-triazolone (Compound 54) as a white powder.

$^1$H-NMR (CDCl$_3$) δ: 4.18 (1H,d,J=15 Hz), 4.40 (2H,t,J= 12 Hz), 4.61 (1H,d,J=15 Hz), 4.71 (2H,s), 5.80 (1H,s), 6.05 (1H,tt,J=5.2, 54 Hz), 6.77–6.87 (2H,m), 7.01 (2H,d,J=8.6 Hz), 7.37 (2H,d,J=8.6 Hz), 7.53 (1H,s), 7.56–7.64 (1H,m), 7.84 (1H,s), 8.15 (1H,s).

m.p. 79°614 80° C.

WORKING EXAMPLE 52

60% Sodium hydride in oil (40 mg) was dispersed in 4 ml of dimethylformamide, and 250 mg of 2-(4-trifluoromethoryphenyl)-3(2H,4H)-1,2,4-triazolone was added with ice cooling. The resulting mixture was stirred at room temperature for 10 minutes.

To the mixture was added 237 mg of (2RS)-2-(2,4-difluorophenyl)-2-(1H-1,2,4-triazol-1-yl)methyloxyrane and the resulting mixture was stirred at room temperature for 22 hours. The reaction solution was fractionated after adding 15 ml of cold water and 30 ml of ethyl acetate and the separated aqueous layer was extracted with ethyl acetate twice. The ethyl acetate layers were combined, washed with water and saturated aqueous solution of sodium chloride successively, dried over magnesium sulfate and distilled off under reduced pressure. The residue was purified by silica gel chromatography (eluate; ethyl acetate:hexane=3:1 to ethyl acetate) to give 92 mg of 4-[(2RS)-2-(2,4-difluorophenyl)-2-hydroxy-3-(1H-1,2,4-triazol-1-yl)propyl]-2-(4-trifluoromethoxyphenyl)-3(2H,4H)-1,2,4-triazolone (Compound 55) as a white powder.

$^1$H-NMR (CDCl$_3$) δ:4.20 (2H,s), 4.51 (1H,d,J=14.4 Hz), 4.80 (1H,d,J=14.4 Hz), 5.93 (1H,s), 6.80–6.89 (2H,m), 7.31 (2H,d,J=9.2 Hz), 7.51–7.59 (1H,m), 7.61 (1H,s), 7.87 (1H, s), 7.92 (2H,d,J=9.2 Hz), 8.05 (1H,s).

m.p. 128°–130 ° C.

WORKING EXAMPLE 53

In the same manner as in working Example 51, starting from 0.19 g of (2RS)-2-(2,4-difluorophenyl)-2-(1-imidazolyl) methyloxirane and 0.23 g of 4-[4-(2,2,3,3-tetrafluoropropoxy)phenyl]-3(2H,4H)-1,2,4-triazolone, 2-[(2RS)-2-

(2,4-difluorophenyl)-2-hydroxy-3-(1-imidazolyl)propyl]-4-[4-(2,2,3,3-tetrafluoropropoxy)phenyl]-3(2H,4H)-1,2,4-triazolone (Compound 56: 0.23 g) was obtained as a colorless powder.

Yield 55%

$^1$H-NMR (CDCl$_3$) δ:4.20 (1H,d,J=15 Hz), 4.37 (2H,s), 4.37 (2H,t,J=12 Hz), 4.57 (1H,d,J=15 Hz), 5.76 (1H,s), 6.04 (1H,tt,J=5.2 Hz, 54 Hz), 6.75–6.98 (2H,m), 6.92 (1H,s), 7.00 (2H,d,J=9.2 Hz), 7.26 (1H,s), 7.35 (2H,d,J=9.2 Hz), 7.43–7.60 (1H,m), 7.45 (1H,s), 7.51 (1H,s).

WORKING EXAMPLE 54

In the same manner as in Working Example 51, starting from 0.24 g of (2R)-2-(2,4-difluorophenyl)-2-(1H-1,2,4-triazol-1-yl)methyloxirane and 0.28 g of 4-[4-(1,1,2,2tetrafluoroethoxy)phenyl]-3(2H,4H)-1,2,4-triazolone, 2-[(2R)-2-(2,4-difluorophenyl)-2-hydroxy-3-(1H-1,2,4-triazol-1-yl)propyl]-4-[4-(1,1,2,2-tetrafluoroethoxy) phenyl]-3(2H, 4H)-1,2,4-triazolone (Compound 78: 0.22 g) was obtained as a colorless powder.

Yield 43%

$^1$H-NMR (CDCl$_3$) δ:4.19 (1H,d,J=15 Hz), 4.61 (1H,d,J=15 Hz), 4.72 (2H,s), 5.71 (1H,s), 5.92 (1H,tt,J=2.8 Hz, 53 Hz), 6.76–6.88 (2H,m), 7.31 (2H,d,J=10 Hz), 7.46–7.64 (1H,m), 7.49(2H,d,J=10 Hz), 7.59 (1H,s), 7.84 (1H,s), 8.14 (1H,s)

WORKING EXAMPLES 55–61

The following compounds were obtained in accordance with the same manner as that described in Working Example 54.

WORKING EXAMPLE 55

2-[(2R)-2-(2,4-Difluorophenyl)-2-hydroxy-3-(1H-1,2,4-triazol-1-yl)propyl]-4-[4-(2,2,2-trifluoroethoxy) phenyl]-3(2H,4H)-1,2,4-triazolone (Compound 90), colorless powder.

Yield 30%.

$^1$H-NMR (CDCl$_3$ ) δ:4.18 (1H,d,J=15 Hz), 4.37 (2H,q,J=8Hz), 4.60 (1H,d,J=15Hz), 4.71 (2H,s), 5.79 (1H,s), 6.77–6.98 (2H,m), 7.02 (2H,d,J=10 Hz), 7.37 (2H,d,J=10 Hz), 7.46–7.64 (1H,m), 7.53 (1H,s), 7.84 (1H,s), 8.15 (1H,s)

WORKING EXAMPLE 56

2-[(2R)-2-(2,4-Difluorophenyl)-2-hydroxy-3-(1H-1,2,4-triazol-1-yl)propyl ]-4-[4-(2,2,3,3,3-pentafluoropropoxy)phenyl]-3 (2H, 4H)-1,2,4-triazolone (Compound 94), colorless powder.

Yield 31%.

$^1$H-NMR (CDCl$_3$) δ: 4.18 (1H,d,J=15 Hz), 4.44 (2H,t,J=12 Hz), 4.60 (1H,d,J=15 Hz), 4.71 (2H,s), 5.79 (1H,s), 6.77–6.86 (2H,m), 7.02 (2H,d,J=8.8 Hz), 7.38 (2H,d,J=8.8 Hz), 7.53 (1H,s), 7.56–7.64 (1H,m), 7.84 (1H,s), 8.15 (1H,s).

$[α]_D^{20}$+13.5° (c=1.0, methanol)

WORKING EXAMPLE 57

4-[(2S)-2-(2,4-Difluorophenyl)-2-hydroxy-3-(1H-1,2,4-triazol-1-yl)propyl]-2-[4-(2,2,3,3-tetrafluoropropoxy) phenyl]-3(2H,4H)-1,2,4-triazolone (Compound 75), colorless powder.

Yield 20%.

$^1$H-NMR (CDCl$_3$) δ: 4.14 (1H,d,J=15 Hz), 4.24 (1H,d,J=15 Hz), 4.32 (2H,t,J=12 Hz), 4.51 (1H,d,J=15 Hz), 4.77 (1H,d,J=15 Hz), 6.02 (1H,s), 6.06 (1H,tt,J=4.8 Hz, 54 Hz), 6.71–6.98 (2H,m), 7.03 (2H,d,J=9.2 Hz), 7.51–7.63 (1H,m), 7.55 (1H,s), 7.79 (2H,d,J=9.2 Hz), 7.86 (1H,s), 8.06 (1H,s).

WORKING EXAMPLE 58

4-[(2S)-2-(2,4-Difluorophenyl)-2-hydroxy-3-(1H-1,2,4-triazol-I-yl)propyl]-2-[4-(1,1,2,2-tetrafluoroethoxy)phenyl]-3 (2H, 4H)-1,2,4-triazolone (Compound 79), colorless powder.

Yield 23%.

$^1$H-NMR (CDCl$_3$) δ: 4.15 (1H,d,J=14 Hz), 4.24 (1H,d,J=14 Hz), 4.50 (1H,d,J=14 Hz), 4.79 (1H,d,J=14 Hz), 5.92 (1H,tt,J=2.8 Hz, 53 Hz), 5.94 (1H,s), 6.79–6.88 (2H,m), 7.25 (2H, d,J=10 Hz), 7.50–7.62 (1H,m), 7.59 (1H,s), 7.87 (1H, s), 7.91 (2H,d,J=10 Hz), 8.05 (1H,s).

$[α]_D^{20}$ −12.4° (c=1.0, methanol)

WORKING EXAMPLE 59

4-[(2S)-2-(2,4-Difluorophenyl)-2-hydroxy-3-(1H-1,2,4-triazol-1-yl)propyl]-2-[4-(2,2,2-trifluoroethoxy)phenyl]-3(2H,4H)-1,2,4-triazolone (Compound 91), colorless powder.

Yield 22%.

$^1$H-NMR (CDCl$_3$) δ: 4.14 (1H,d,J=14 Hz), 4.24 (1H,d,J=14 Hz), 4.35 (2H,q,J=8 Hz), 4.51 (1H,d,J=14 Hz), 4.76 (1H,d,J=14 Hz), 6.02 (1H,s), 6.72–6.89 (2H,m), 6.97 (2H, d,J=9.2 Hz), 7.51–7.63 (1H,m), 7.55 (1H,s), 7.79 (2H,d,J=9.2 Hz), 7.86 (1H,s), 8.06 (1H,s).

WORKING EXAMPLE 60

2-[(2R)-2-(2,4-Difluorophenyl)-2-hydroxy-3-(1H-1,2,4-triazol-1-yl)propyl]-4-[4-(2,2,3,3-tetrafluoropropoxy)phenyl]-3(2H, 4H)-1,2,4-triazolone (Compound 74), colorless powder.

Yield 46%

$^1$H-NMR (CDCl$_3$) δ:4.18 (1H,d,J=15 Hz), 4.40 (2H,t,J=12 Hz), 4.61 (1H,d,J=15 Hz), 4.71 (2H,s), 5.80 (1H,s), 6.05 (1H, tt, J=5.2 Hz, 54 Hz), 6.77–6.87 (2H,m), 7.01 (2H,d,J=8.6 Hz), 7.37 (2H,d,J=8.6 Hz), 7.53 (1H,s), 7.56–7.64 (1H, m), 7.84 (1H,s), 8.15 (1H,s).

WORKING EXAMPLE 61

2-[(2R)-2-(2,4-Difluorophenyl)-2-hydroxy-3-(1H-1,2,4-triazol-1-yl)propyl ]-4-(4-trifluoromethoxyphenyl)-3(2H, 4H)-1,2,4-triazolone (Compound 70), colorless powder.

Yield 41%, $^1$H-NMR (CDCl$_3$) δ: 4.19 (1H,d,J=15 Hz), 4.60 (1H,d,J=15 Hz), 4.72 (2H,s), 5.69 (1H,s), 6.76–6.88 (2H,m), 7.32 (2H,d,J=9 Hz), 7.46–7.64 (1H, m), 7.50 (2H, d, J=9 Hz), 7.59 (1H,s), 7.84 (1H,s), 8.14 (1H,s).

WORKING EXAMPLE 62–71

The following compounds were obtained in accordance with the same manner as that described in working Example 2.

WORKING EXAMPLE 62

1-[(1R,2R)-2-(2,4-Difluorophenyl)-2-hydroxy-1-methyl-3-(1H-1,2,4-triazol-1-yl)propyl]-3-[4-[4-[4-(2,2,3,3-tetrafluoropropoxy)phenyl]-1-piperazinyl]phenyl]-2(1H,3H)- imidazolone (Compound 10.4), colorless powder.

Yield 62%.

$^1$H-NMR (CDCl$_3$) δ: 1.22 (3H,d,J=7 Hz), 3.23–3.38 (8H, m), 4.22 (1H,d,J=15 Hz), 4.31 (2H,t,J=12 Hz), 4.92 (1H,q, J=7 Hz), 5.10 (1H,d,J=15 Hz), 6.08 (1H,tt,J=53, 5 Hz), 6.59 (1H,d,J=3.0 Hz), 6.68 (1H,d,J=3.0 Hz), 6.73–7.06 (8H,m), 7.43–7.54 (3H,m), 7.72 (1H,s), 7.89 (1H,s).

WORKING EXAMPLE 63

2-[(1R,2R)-2-(2,4-Difluorophenyl)-2-hydroxy-1-methyl-3-(1H-1,2,4-triazol-1-yl)propyl]-4-[4-[4-(2,2,3,3-tetrafluoropropoxy)phenyl]-1-piperazinyl]phenyl]-3(2H,4H)-1,2,4-triazolone (Compound 105), colorless powder.

Yield 54%.

$^1$H-NMR (CDCl$_3$) δ: 1.29 (3H,d,J=7.0 Hz), 3.23–3.42 (8H,m), 4.31 (2H,t,J=12 Hz), 4.35 (1H,d,J=15 Hz), 5.02 (1H,d,J=15 Hz), 5.09 (1H,q,J=7.0 Hz), 5.58 (1H,s), 6.07 (1H,tt,J=53, 5.0 Hz), 6.76–7.00 (6H,m), 7.06 (2H,d,J=9 Hz), 7.43 (2H,d,J=9 Hz), 7.50–7.62 (1H,m), 7.68 (1H,s), 7.73 (1H,s), 7.96 (1H,s).

WORKING EXAMPLE 64

1-[(1R,2R)-2-(2,4-Difluorophenyl)-2-hydroxy-1-methyl-3-(1H-1,2,4-triazol-1-yl)propyl]-4-[4-(2,2,2-trifluoroethoxy)phenyl]-5(1H,4H)-tetrazolone (Compound 106), colorless powder.

Yield 27%.

$^1$H-NMR (CDCl$_3$) δ: 1.46 (3H,d,J=7 Hz), 4.35 (1H,d,J=16 Hz), 4.41 2H,q,J=8 Hz), 5.08 (1H,d,J=16 Hz), 5.10 (1H,q,J=7 Hz), 5.51 (1H,s), 6.75–6.88 (2H,m), 7.09 (2H,d, J=9 Hz), 7.51–7.63 (1H,m), 7.72 (1H,s), 7.90 (2H,d,J=9 Hz), 7.91 (1H,s).

WORKING EXAMPLE 65

1-[(1R,2R)-2-(2,4-Difluorophenyl)-2-hydroxy-1-methyl-3-(1H-1,2,4-triazol-1-yl)propyl]-4-[4-(1,1,2,2-tetrafluoroethoxy)phenyl]-5(1H,4H)-tetrazolone (Compound 107), colorless prisms.

Yield 48%.

$^1$H-NMR (CDCl$_3$) δ:1.46 (3H,d,J=7.2 Hz), 4.34 (1H,d,J= 14.4 Hz), 5.08 (1H,d,J=14.4 Hz), 5.10 (1H, q, J=7.2 Hz), 5.50 (1H,s), 5.95 (1H, tt, J=52.8, 2.8 Hz), 6.73–6.91 (2H,m), 7.38 (2H,d,J=9 Hz), 7.49–7.64 (1H,m), 7.72 (1H,s), 7.91 (1H,s), 8.01 (2H,d,J=9 Hz).

IRγ$_{max}^{KBr}$ cm$^{-1}$: 3400, 3080, 1730, 1518, 1514, 1502, 1387.

WORKING EXAMPLE 66

1-[(1R,2R)-2-(2,4-Difluorophenyl)-2-hydroxy-1-methyl-3-(1H-1,2,4-triazol-1-yl)propyl]-4-[4-(2,2,3,3,3-pentafluoropropoxy)phenyl]-5(1H,4H)-tetrazolone (Compound 108), colorless powder.

Yield 53%.

$^1$H-NMR (CDCl$_3$) δ:1.45 (3H,d,J=7.2 Hz), 4.35 (1H,d,J= 14.2 Hz), 4.47 (2H,dt,J=12.2, 1 Hz), 5.08 (1H,d,J=14.2 Hz), 5.10 (1H,q,J=7.2 Hz), 5.50 (1H,s), 5.74–6.90 (2H,m), 7.09 (2H,d,J=9.2 Hz), 7.49–7.65 (1H,m), 7.72 (1H,s), 7.90 (2H, d,J=9.2 Hz), 7.91 (1H,s).

IRγ$_{max}^{KBR}$ cm$^{-1}$: 3400, 3080, 1726, 1518, 1599, 1515, 1460.

WORKING EXAMPLE 67

1-[(1R,2R)-2-(2,4-Difluorophenyl)-2-hydroxy-1-methyl-3-(1H-1,2,4-triazol-1-yl)propyl]-4-[4-(2,2,3,3,4,4,5,5-octafluoropenthoxy)phenyl]-5(1H,4H)-tetrazolone (Compound 109), colorless powder.

Yield 42%.

$^1$H-NMR (CDCl$_3$) δ: 1.46 (3H,d,J=7.2 Hz), 4.35 (1H,d, J=14.4 Hz), 4.53 (2H,t,J=13 Hz), 5.08 (1H,d,J=14.4 Hz), 5.10 (1H,q,J=7.2 Hz)t 5.52 (1H,s), 6.11 (1H,tt,J=52, 5.4 Hz), 6.74–6.91 (2H,m), 7.10 (2H,d,J=9.2 Hz), 7.50–7.56 (1H,m), 7.73 (1H,s), 7.91 (2H, d, J=9.2 Hz), 7.92 (1H,s).

IRγ$_{max}^{KBr}$ cm$^{-1}$: 3400, 3080, 1722, 1518, 1599, 1515, 1459.

WORKING EXAMPLE 68

2-[(1R,2R)-2-(2,4-Difluorophenyl)-2-hydroxy-1-methyl-3-(1H-1,2,4-triazol-1-yl)propyl]-5-methyl-4-[4-(2,2,3,3-tetrafluoropropoxy)phenyl]-3(2H,4H)-1,2,4-triazolone (Compound 110), colorless powder.

Yield 44%.

$^1$H-NMR (CDCl$_3$) δ:1.25 (3H,d,J=7 Hz), 2.19 (3H,s), 4.40 (1H,d,J=14.8 Hz), 4.42 (2H,t,J=11.8 Hz), 4.97 (1H,d, J=14.8 Hz), 5.06 (1H,q,J=7 Hz), 5.52 (1H,s), 6.08 (1H,tt,J= 53.2 Hz,J=4.6 Hz), 6.84–6.90 (2H,m), 7.09 (2H,dt,J=9 Hz,J=2.8 Hz), 7.33 (2H,dt,J=9 Hz,J=2.8 Hz), 7.50–7.55 (1H,m), 7.70 (1H,s), 7.98 (1H,s).

WORKING EXAMPLE 69

2-[(1R,2R)-2-(2,4-Difluorophenyl)-2-hydroxy-1-methyl-3-(1H-1,2,4-triazol-1-yl)propyl]-5-methyl-4-[4-(1,1,2,2-tetrafluoroethoxy)phenyl]-3(2H,4H)-1,2,4-triazolone (Compound 111), colorless powder.

Yield 46%.

$^1$H-NMR (CDCl$_3$) δ:1.25 (3H,d,J=7 Hz), 2.24 (3H,s), 4.42 (1H,d,J=14.6 Hz), 4.98 (1H,d,J=14.8 Hz), 5.07 (1H,q, J=7 Hz), 5.55 (1H,s), 5.96 (1H,tt,J=53.2 Hz,J=2.8 Hz), 6.75–6.90 (2H,m), 7.41 (4H,s), 7.50–7.65 (1H,m), 7.71 (1H,s), 7.97 (1H,s).

WORKING EXAMPLE 70

2-(4-Chlorophenyl)-4-[(1R,2R)-2-(2,4-difluorophenyl)-2-hydroxy-1-methyl-3-(1H-1,2,4-triazol-1-yl)propyl]-5-methyl-3(2H,4H)-1,2,4-triazolone (Compound 112), colorless powder.

Yield 77%.

$^1$H-NMR (400 MHz,DMSO-d$_6$, 138° C.) δ: 1.33 (3H,d, J=7 Hz), 2.38 (3H,s), 4.49 (1H,d,J=14.2 Hz), 4.76–4.90 (1H,m), 4.89 (1H,d,J=14.2 Hz), 5.23 (1H,br), 6.88–6.95 (1H,m), 5.99–7.07 (1H,m), 7.46–7.54 (1H,m), 7.46 (2H,d, J=9 Hz), 7.55 (1H,s), 7.90 (2H,d,J=9 Hz), 8.14 (1H,s).

IRγ$_{max}^{KBr}$ cm$^{-1}$: 1712, 1702, 1680, 1650, 1519, 1502.

WORKING EXAMPLE 71

4-[(1R,2R)-2-(2,4-Difluorophenyl)-2-hydroxy-1-methyl-3-(1H-1,2,4-triazol-1-yl)propyl]-5-methyl-2-(4-trifluoromethoxyphenyl)-3(2H,4H)-1,2,4-triazolone (Compound 113), colorless powder. Yield 72%.

IRγ$_{max}^{KBr}$ cm$^{-1}$: 1700, 1678, 1510, 1508, 1256, 1220.

WORKING EXAMPLE 72

TO a mixture of 60 (w/w) % sodium hydride in oil (10 and dimethylformamide (2 ml) was added 4-(4-trifluoromethylphenyl)- 3(2H,4H)-1,2,4-triazolone (59 mg) at 0° C. The resulting mixture was stirred for 10 minutes at room temperature. To the mixture was added (2R,3S)-2-(2,4-difluorophenyl)-3-methyl-2-[(1H-1,2,4-triazol-1-yl)methyl]oxirane (63 mg). After stirring for 19 hours at 70 ° C., the mixture was diluted with water (4 ml) and extracted with ethyl acetate (4 ml×2). The extract was washed with water and saturated aqueous sodium chloride solution successively, dried over anhydrous magnesium sulfate and concentrated under reduced pressure. The residue was purified by silica gel columnchromatography (eluent; ethyl acetate:hexane=3:1 to ethyl acetate) to give 2-[(1R,2R)-2-(2,4-difluorophenyl)-2-hydroxy-1-methyl-3-(1H-1,2,4-triazol-1-yl)propyl]-4-(4-trifluoromethylphenyl)-3(2H,4H)-1,2,4-triazolone (Compound 10) as a colorless powder (10 mg).

WORKING EXAMPLE 73

In the same manner as in Working Example 72, (2R,3S)-2-(2,4-difluorophenyl)-3-methyl-2-[(1H-1,2,4-triazol-1-yl)methyl]oxirane (63 mg) was allowed to react with 2-(4-trifluoromethylphenyl)-3(2H,4H)-1,2,4-triazolone (59 mg) to give 4-[(1R,2R)-2-(2,4-difluorophenyl)-2-hydroxy-1-methyl-3-(1H-1,2,4-triazol-1-yl)propyl]-2-(4-trifluoromethylphenyl)-3(2H,4H)-1,2,4-triazolone (Compound 11) as a white powder (12 mg).

WORKING EXAMPLE 74

In the same manner as in Working Example 72, (2R,3S)-2-(2,4-difluorophenyl)-3-methyl-2-[(1H-1,2,4-triazol-1-yl)methyl]oxirane (251 mg) was allowed to react with 2-(4-fluorophenyl)-3(2H,4H)-1,2,4-triazolone (358 mg) to give 4-[(1R,2R)-2-(2,4-difluorophenyl)-2-hydroxy-1-methyl-3-(1H-1,2,4-triazol-1-yl)propyl]-2-(4-fluorophenyl)-3(2H,4H)-1,2,4-triazolone (Compound 15) as a white powder (76 mg).

WORKING EXAMPLE 75

In the same manner as in Working Example 72, (2R,3S)-2-(2,4-difluorophenyl)-3-methyl-2-[(1H-1,2,4-triazol-1-yl)methyl]oxirane (251 mg) was allowed to react with 2-(4-chlorophenyl)-3(2H,4H)-1,2,4-triazolone (392 mg) to give 2-(4-chlorophenyl)-4-[(1R,2R)-2-(2,4-difluorophenyl)-2-hydroxy-1-methyl-3-(1H-1,2,4-triazol-1-yl)propyl]-3(2H,4H)-1,2,4-triazolone (Compound 35) as colorless prisms (48 mg).

Preferred group of compounds belonging to the compound of the formula (I) of the present invention are exemplified in Table 8 to Table 27 though the present invention is not limited to the compounds given there.

TABLE 8

[Structure: triazole-N-CH₂-C(OH)(R)(2,4-difluorophenyl)-CH(R)(CH₃)-A]

| Cpd. No. | −A |
|---|---|
| 1 | −N(C=O)N(CH=CH)−phenyl |
| 2 | −N(C=O)N(CH=CH)−C₆H₄−CF₃ |
| 3 | −N(C=O)N(CH=CH)−CH₃ |
| 4 | −N(C=O)N(CH=CH)−C₆H₄−F |
| 5 | −N(C=O)N(CH=CH)−2,4-difluorophenyl |

TABLE 9

| Cpd. No. | −A |
|---|---|
| 6 | −N(C=O)N(CH=CH,N)−C₆H₄−F |
| 7 | −N(C=O)N(CH=CH)−C₆H₄−OCH₃ |
| 8 | −N(C=O)N(CH=CH,N)−C₆H₄−OCH₃ |

TABLE 9-continued
| Cpd. No. | —A |
|---|---|
| 9 | 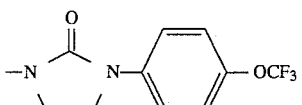 |
| 10 | 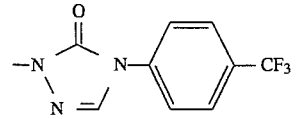 |
| 11 | 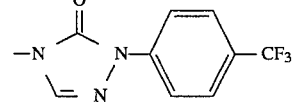 |
| 12 | 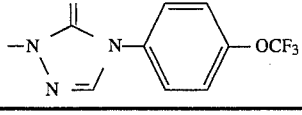 |
TABLE 10
| Cpd. No. | —A |
|---|---|
| 13 | 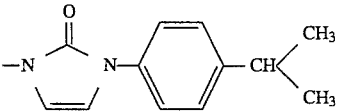 |
| 14 | 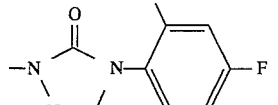 |
| 15 | 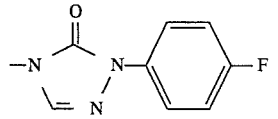 |
| 16 | 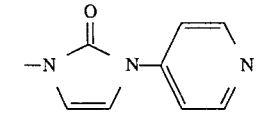 |
| 17 | 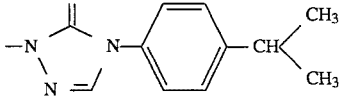 |
| 18 | 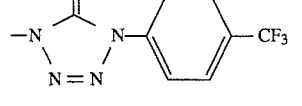 |
TABLE 10-continued
| Cpd. No. | —A |
|---|---|
| 19 | 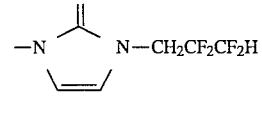 |
TABLE 11
| Cpd. No. | —A |
|---|---|
| 20 | 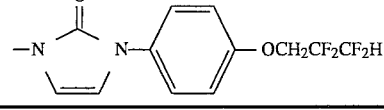 |
| 21 | 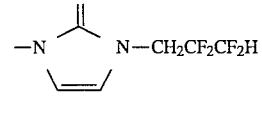 |
| 22 | 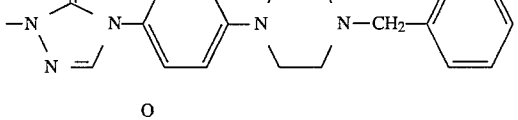 |
| 23 | 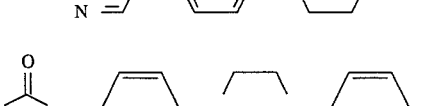 |
| 24 | 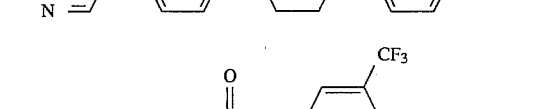 |
| 25 | 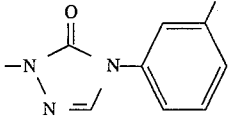 |
TABLE 12
| Cpd. No. | —A |
|---|---|
| 26 | 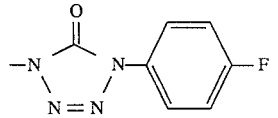 |
| 27 | 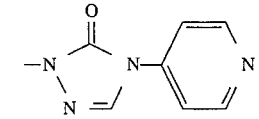 |

TABLE 12-continued

| Cpd. No. | —A |
|---|---|
| 28 | [structure: triazolone with pyrimidine] |
| 29 | [structure: triazolone with N—CH2CF3] |
| 30 | [structure: triazolone with phenyl-OCH2CF2CF2H] |
| 31 | [structure: triazolone with 2-CF3-phenyl] |
| 32 | [structure: triazolone with phenyl-OCH(CH3)2] |

TABLE 13

| Cpd. No. | —A |
|---|---|
| 33 | [structure: triazolone with N—(CH2)2CH(CH3)2] |
| 34 | [structure: triazolone with phenyl-OCF2CF2H] |
| 35 | [structure: triazolone with 4-Cl-phenyl] |
| 36 | [structure: triazolone with phenyl-OCF3] |

TABLE 14

| Cpd. No. | —A |
|---|---|
| 37 | [structure: tetrazolone with phenyl-OCF3] |
| 38 | [structure: tetrazolone with phenyl-OCH2CF2CF2H] |
| 39 | [structure: tetrazolone with 4-Cl-phenyl] |
| 40 | [structure: imidazolone with phenyl-OCF2CF2H] |
| 41 | [structure: imidazolone with 4-Cl-phenyl] |
| 42 | [structure: triazolone with 4-Cl-phenyl] |
| 43 | [structure: imidazolone with phenyl-OCH2(CF2)4H] |

TABLE 15

| Cpd. No. | —A |
|---|---|
| 44 | [structure: imidazolone with phenyl-OCH2CF3] |
| 45 | [structure: imidazolone with phenyl-OCH2CF2CF3] |
| 46 | [structure: triazolone with phenyl-OCH2CF3] |
| 47 | [structure: triazolone with phenyl-OCH2CF2CF3] |
| 48 | [structure: triazolone with phenyl-OCH2(CF2)4H] |

TABLE 15-continued

| Cpd. No. | —A |
|---|---|
| 49 | N-methyl triazinone with phenyl-OCH₂CF₃ substituent |
| 50 | N-methyl triazinone with phenyl-OCH₂CF₂CF₃ substituent |

TABLE 16

| Cpd. No. | —A |
|---|---|
| 51 | N-methyl triazinone with phenyl-OCH₂(CF₂)₄H substituent |
| 52 | N-methyl triazinone with phenyl-OCH₂CF₂CF₂H substituent |
| 53 | N-methyl triazinone with phenyl-OCF₂CF₂H substituent |

TABLE 17

| Cpd. No. | —A |
|---|---|
| 104 | N-methyl imidazolone-N-phenyl-piperazine-N-phenyl-OCH₂CF₂CF₂H |
| 105 | N-methyl triazinone-N-phenyl-piperazine-N-phenyl-OCH₂CF₂CF₂H |
| 106 | N-methyl tetrazinone with phenyl-OCH₂CF₃ substituent |
| 107 | N-methyl tetrazinone with phenyl-OCF₂CF₂H substituent |

TABLE 18

| Cpd. No. | —A |
|---|---|
| 108 | N-methyl tetrazinone with phenyl-OCH₂CF₂CF₃ substituent |
| 109 | N-methyl tetrazinone with phenyl-OCH₂(CF₂)₄H substituent |
| 110 | N-methyl-(5-methyl)triazinone with phenyl-OCH₂CF₂CF₂H substituent |
| 111 | N-methyl-(5-methyl)triazinone with phenyl-OCH₂CF₂H substituent |
| 112 | N-methyl-(5-methyl)triazinone with phenyl-Cl substituent |

TABLE 18-continued

| Cpd. No. | —A |
|---|---|
| 113 | (N-methyl-triazinone with methyl and p-OCF₃-phenyl-N substituents) |

TABLE 19

Structure: triazole-N—CH₂—C*(OH)(2,4-difluorophenyl)—CH₂—A (X in ring)

| Cpd. No. | X | Configuration C* | —A |
|---|---|---|---|
| 54 | N | (RS) | triazolinone-N-phenyl-OCH₂CF₂CF₂H |
| 55 | N | (RS) | triazinone-N-phenyl-OCF₃ |
| 56 | CH | (RS) | triazolinone-N-phenyl-OCH₂CF₂CF₂H |

TABLE 20

Structure: triazole-N—CH₂—C*(OH)(2,4-difluorophenyl)—CH₂—A

| Cpd. No. | Configuration C* | —A |
|---|---|---|
| 57 | (S) | triazolinone-N-phenyl-CF₃ |
| 58 | (R) | triazolinone-N-phenyl-CF₃ |
| 59 | (S) | triazinone-N-phenyl-CF₃ |
| 60 | (R) | tetrazolinone-N-phenyl-CF₃ |
| 61 | (S) | imidazolinone-N-phenyl-F |

TABLE 21

| Cpd. No. | Configuration C* | —A |
|---|---|---|
| 62 | (R) | triazolinone-N-phenyl-F |
| 63 | (S) | triazinone-N-phenyl-F |
| 64 | (R) | tetrazolinone-N-phenyl-F |
| 65 | (S) | triazolinone-N-(2,4-difluorophenyl) |
| 66 | (R) | triazinone-N-(2,4-difluorophenyl) |

TABLE 21-continued

| Cpd. No. | Configuration C* | —A |
|---|---|---|
| 67 | (S) | 2,4-difluorophenyl dihydrotriazinone derivative |

TABLE 22

| Cpd. No. | Configuration C* | —A |
|---|---|---|
| 68 | (R) | 2,4-difluorophenyl tetrazinone derivative |
| 69 | (S) | 4-OCF₃ phenyl dihydrotriazinone derivative |
| 70 | (R) | 4-OCF₃ phenyl dihydrotriazinone derivative |
| 71 | (S) | 4-OCF₃ phenyl dihydrotriazinone derivative |
| 72 | (R) | 4-OCF₃ phenyl tetrazinone derivative |
| 73 | (S) | 4-OCH₂CF₂CF₂H phenyl dihydroimidazolone derivative |

TABLE 23

| Cpd. No. | Configuration C* | —A |
|---|---|---|
| 74 | (R) | 4-OCH₂CF₂CF₂H phenyl dihydrotriazinone derivative |
| 75 | (S) | 4-OCH₂CF₂CF₂H phenyl dihydrotriazinone derivative |

TABLE 23-continued

| Cpd. No. | Configuration C* | —A |
|---|---|---|
| 76 | (R) | 4-OCH₂CF₂CF₂H phenyl tetrazinone derivative |
| 77 | (S) | 4-OCF₂CF₂H phenyl dihydrotriazinone derivative |
| 78 | (R) | 4-OCF₂CF₂H phenyl dihydrotriazinone derivative |
| 79 | (S) | 4-OCF₂CF₂H phenyl dihydrotriazinone derivative |

TABLE 24

| Cpd. No. | Configuration C* | —A |
|---|---|---|
| 80 | (R) | 4-OCF₂CF₂H phenyl tetrazinone derivative |
| 81 | (S) | 4-Cl phenyl dihydrotriazinone derivative |
| 82 | (R) | 4-Cl phenyl dihydrotriazinone derivative |
| 83 | (S) | 4-Cl phenyl dihydrotriazinone derivative |
| 84 | (R) | 4-Cl phenyl tetrazinone derivative |
| 85 | (S) | 4-OCH₂(CF₂)₄H phenyl dihydroimidazolone derivative |

TABLE 25
| Cpd. No. | Configuration C* | —A |
|---|---|---|
| 86 | (R) | 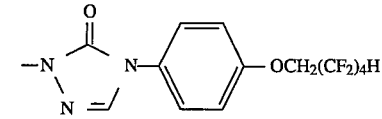 |
| 87 | (S) | 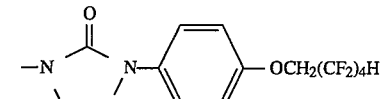 |
| 88 | (R) | 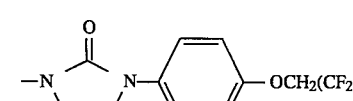 |
| 89 | (S) | 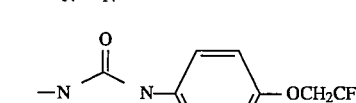 |
| 90 | (R) | 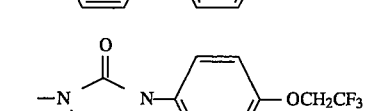 |
| 91 | (S) |  |
TABLE 26
| Cpd. No. | Configuration C* | —A |
|---|---|---|
| 92 | (R) | 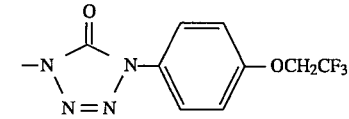 |
| 93 | (S) | 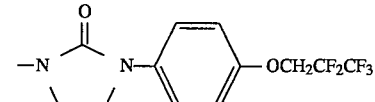 |
| 94 | (R) | 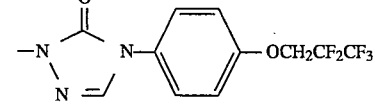 |
| 95 | (S) | 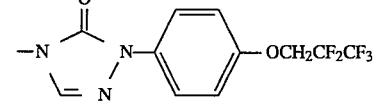 |
| 96 | (R) | 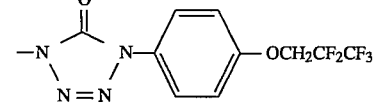 |
| 97 | (R) | 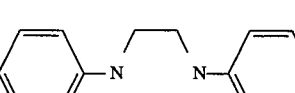 |
TABLE 27
| Cpd. No. | Configuration C* | —A |
|---|---|---|
| 98 | (R) | 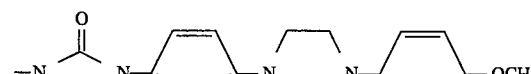 |
| 99 | (S) |  |
| 100 | (R) | 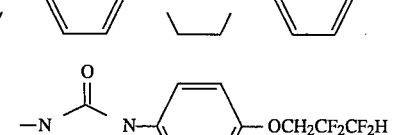 |

TABLE 27-continued

| Cpd. No. | Configuration C* | —A |
|---|---|---|
| 101 | (R) | —N-C(=O)-N(-C6H4-OCF2CF2H)-N=C(CH3)- (cyclic) |
| 102 | (S) | —N-C(=O)-N(-C6H4-Cl)-N=C(CH3)- (cyclic) |
| 103 | (S) | —N-C(=O)-N(-C6H4-OCF3)-N=C(CH3)- (cyclic) |

Preparation 1

Using the Compound 30 obtained in Working Example 27, the components stated below were mixed. The mixture was packed in gelatin capsules to obtain capsules, each of which contains the Compound 30 in an amount of 50 mg.

| | |
|---|---|
| Compound 30 (obtained in Working Example 27) | 50 mg |
| Lactose | 100 mg |
| Cornstarch | 40 mg |
| Magnesium stearate | 10 mg |
| Total | 200 mg |

Preparation 2

The Compound 35 obtained in Working Example 32 and magnesium stearate were granulated in a solution of soluble starch. The resultant product was dried, and then mixed with lactose and cornstarch. The mixture was subjected to compression molding to obtain a tablet containing the components stated below.

| | |
|---|---|
| Compound 35 (obtained in Working Example 32) | 50 mg |
| Lactose | 65 mg |
| Cornstarch | 30 mg |
| Soluble starch | 35 mg |
| Magnesium stearate | 20 mg |
| Total | 200 mg |

Evaluation of the antifungal activities of the compound of formula (I) was conducted by the following method: a sheet of filter paper disc (manufactured by Toyo Seisakusho, 8 mm in diameter) soaked in a 1000 µg/ml solution of a compound of formula (I) in methanol was placed on an agar plate containing various fungi, which was incubated at 28° C. for two days, and the diameter of the growth inhibition zone around the filter paper disc was measured. The following culture media were used:
A: yeast nitrogen base agar medium (pH 7.0)
B: peptone-yeast extract-glucose agar medium (pH 7.0)

The antifungal spectra of the compounds of formula (I) are shown in Table 28.

TABLE 28

| | | Diameter of growth inhibition zone (mm) | | |
|---|---|---|---|---|
| Test microorganism | Medium | cpd. 1 | cpd. 2 | cpd. 3 |
| Candida albicans IFO 0583 | A | 45 | 40 | 40 |
| Candida utilis IFO 0619 | A | 45 | 35 | 22 |
| Aspergillus niger IFO 4066 | A | 35 | 27 | 13 |
| Aspergillus fumigatus IFO 6344 | A | 43 | 36 | 22 |
| Cryptococcus neoformans IFO 0410 | A | 30 | 30 | 22 |
| Trichophyton rubrum IFO 6467 | B | 55 | 52 | 35 |
| Trichophyton mentagrophytes IFO 7522 | B | 55 | 50 | 20 |
| Microsporum gypseum IFO 6076 | B | 55 | 43 | 20 |

The antifungal activities of the compound of formula (I) against Candida albicans are shown in Tables 29 to 32.

TABLE 29

| | Diameter of growth-inhibition zone (mm) Candida albicans (IFO 0583) |
|---|---|
| cpd. No. | (Medium A, 28° C., two-day culture) |
| 4 | 43 |
| 5 | 47 |
| 6 | 45 |
| 7 | 50 |
| 8 | 47 |
| 9 | 44 |
| 10 | 47 |
| 11 | 38 |
| 12 | 33 |
| 13 | 42 |
| 14 | 47 |
| 15 | 46 |
| 17 | 42 |

TABLE 29-continued

| cpd. No. | Diameter of growth-inhibition zone (mm) Candida albicans (IFO 0583) (Medium A, 28° C., two-day culture) |
|---|---|
| 18 | 31 |
| 19 | 43 |

TABLE 30

| cpd. No. | Diameter of growth-inhibition zone (mm) Candida albicans (IFO 0583) (Medium A, 28° C., two-day culture) |
|---|---|
| 21 | 27 |
| 23 | 35 |
| 24 | 31 |
| 25 | 30 |
| 26 | 48 |
| 27 | 37 |
| 28 | 24 |
| 29 | 31 |
| 30 | 41 |
| 31 | 38 |
| 32 | 45 |
| 33 | 46 |
| 34 | 43 |
| 35 | 45 |
| 36 | 41 |

TABLE 31

| cpd. No. | Diameter of growth-inhibition zone (mm) Candida albicans (IFO 0583) (Medium A, 28° C., two-day culture) |
|---|---|
| 37 | 35 |
| 38 | 33 |
| 39 | 45 |
| 40 | 42 |
| 41 | 45 |
| 42 | 47 |
| 43 | 32 |
| 44 | 44 |
| 45 | 35 |
| 46 | 45 |
| 47 | 36 |
| 48 | 26 |
| 49 | 44 |
| 50 | 30 |

TABLE 32

| cpd. No. | Diameter of growth-inhibition zone (mm) Candida albicans (IFO 0583) (Medium A, 28° C., two-day culture) |
|---|---|
| 51 | 21 |
| 52 | 33 |
| 53 | 37 |
| 54 | 34 |
| 55 | 43 |
| 56 | 35 |
| 75 | 40 |
| 78 | 42 |
| 79 | 45 |
| 90 | 40 |
| 91 | 42 |
| 94 | 41 |
| 105 | 18 |

The protective effects of the compound of formula (I) against Candida albicans infection in mice are shown in the following Tables 33 and 34.

Test Method: Five-week-old Crj:CDF$_1$ mice were inoculated with the minimum lethal dose of Candida albicans intravenously. The test compound was administered orally once immediately after infection. The activity was expressed in terms of ED$_{50}$ values calculated by the Reed and Muench method from the survival rate 7 days after infection.

TABLE 33

| cpd. No. | ED$_{50}$ (mg/kg) p. o. |
|---|---|
| 2 | 0.35 |
| 3 | 11.3 |
| 4 | 8.0 |
| 6 | 0.71 |
| 8 | 0.39 |
| 9 | 2.0 |
| 10 | 0.18 |
| 11 | 0.16 |
| 12 | 0.35 |
| 14 | 0.39 |
| 15 | 8.0 |
| 18 | 2.0 |
| 21 | 8.0 |
| 24 | 8.0 |
| 25 | 2.0 |
| 26 | 2.0 |
| 27 | 8.0 |
| 29 | 1.41 |
| 30 | 0.32 | p. o.: oral administration

TABLE 34

| cpd. No. | ED$_{50}$ (mg/kg) p. o. |
|---|---|
| 34 | 0.16 |
| 35 | 0.088 |
| 36 | 0.19 |
| 37 | 2.0 |
| 38 | 2.0 |
| 39 | <1.0 |
| 40 | <0.25 |
| 41 | 2.0 |
| 42 | 0.18 |
| 44 | <1.0 |
| 45 | <1.0 |
| 46 | <0.25 |
| 47 | <1.0 |
| 49 | <0.25 |
| 50 | <1.0 |
| 52 | 0.22 |
| 53 | 0.18 | p. o.: oral administration

What we claim is;

1. A process for preparing a compound of the formula (I'):

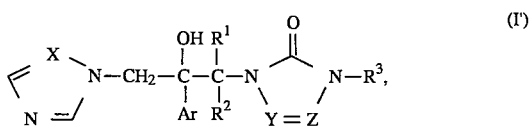

wherein Ar is a substituted phenyl group: $R^1$ and $R^2$ independently are a hydrogen atom or a lower alkyl group, or $R^1$ and $R^2$ may combine together to form a lower alkylene group; $R^3$ is an optionally substituted aliphatic or aromatic hydrocarbon residue or an optionally substituted aromatic heterocyclic group; X is a nitrogen atom or a methine group; and Y and Z independently are a nitrogen atom or a methine group which may optionally be substituted with a lower alkyl group, or a salt thereof, which is characterized by reacting a compound represented by the formula (II):

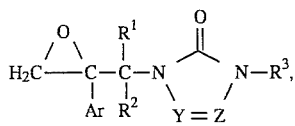
(II)

wherein the symbols have the same meanings as defined in the formula (I'), with a compound represented by the formula (III):

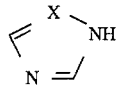
(III)

wherein the symbols have the same meanings as defined in the formula (I') in a solvent selected from the group consisting of sulfoxides, amides and ureylenes in the presence of a base selected from the group consisting of alkali metal hydrides, alkali metal carbonates and tetrabutylammonium fluoride.

2. A process for preparing a compound of formula (I'):

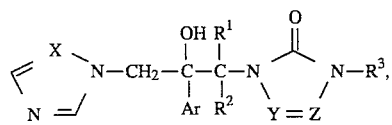
(I')

wherein Ar is a substituted phenyl group; $R^1$ and $R^2$ independently are a hydrogen atom or a lower alkyl group, or $R^1$ and $R^2$ may combine together to form a lower alkylene group; $R^3$ is an optionally substituted aliphatic or aromatic hydrocarbon residue or an optionally substituted aromatic heterocyclic group; X is a nitrogen atom or a methine group; and Y and Z independently are a nitrogen atom or a methine group which may optionally be substituted with a lower alkyl group, or a salt thereof, which is characterized by reacting a compound represented by the formula (IV):

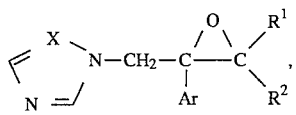
(IV)

wherein the symbols have the same meanings as defined in the formula (I'), or a salt thereof, with a compound represented by the formula (V):

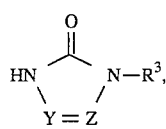
(V)

wherein the symbols have the same meanings as defined in the formula (I') in a solvent selected from the group consisting of sulfoxides, amides and ureylenes in the presence of a base selected from the group consisting of alkali metal hydrides, alkali metal carbonates and tetrabutylammonium fluoride.

* * * * *

UNITED STATES PATENT AND TRADEMARK OFFICE
CERTIFICATE OF CORRECTION

PATENT NO.  : 5,466,820
DATED       : November 14, 1995
INVENTOR(S) : Ito et al.

It is certified that error appears in the above-indentified patent and that said Letters Patent is hereby corrected as shown below:

On title page, item
[62]) was misprinted as "5,371,181" should read
--5,371,101--.

Signed and Sealed this

Twenty-fifth Day of March, 1997

Attest:

BRUCE LEHMAN

Attesting Officer

Commissioner of Patents and Trademarks